(12) United States Patent
Reeh et al.

(10) Patent No.: US 12,239,791 B2
(45) Date of Patent: *Mar. 4, 2025

(54) HYPOXIA TRAINING DEVICE

(71) Applicant: Lynntech, Inc., College Station, TX (US)

(72) Inventors: Jonathan Reeh, College Station, TX (US); Mahesh Waje, College Station, TX (US); Mehmet Kesmez, College Station, TX (US); Carlos Salinas, Bryan, TX (US); Jibi Varughese, College Station, TX (US); John Zbranek, College Station, TX (US); Seth Cocking, College Station, TX (US); Ashwin Balasubramanian, College Station, TX (US); Cory Teurman, College Station, TX (US); James Netherland, Bryan, TX (US); Geoffrey Duncan Hitchens, Allen, TX (US)

(73) Assignee: Lynntech, Inc., College Station, TX (US)

( * ) Notice: Subject to any disclaimer, the term of this patent is extended or adjusted under 35 U.S.C. 154(b) by 958 days.

This patent is subject to a terminal disclaimer.

(21) Appl. No.: 17/232,701

(22) Filed: Apr. 16, 2021

(65) Prior Publication Data

US 2021/0252246 A1 Aug. 19, 2021

Related U.S. Application Data

(63) Continuation of application No. 15/975,301, filed on May 9, 2018, now Pat. No. 11,007,339, which is a (Continued)

(51) Int. Cl.
*A61M 16/10* (2006.01)
*A61M 16/00* (2006.01)
(Continued)

(52) U.S. Cl.
CPC ........ *A61M 16/10* (2013.01); *A61M 16/0045* (2013.01); *A61M 16/101* (2014.02);
(Continued)

(58) Field of Classification Search
CPC .............. A61M 16/10; A61M 16/0045; A61M 16/101; A61M 16/202; A61M 16/22;
(Continued)

(56) References Cited

U.S. PATENT DOCUMENTS 3,489,670 A 1/1970 Maget
3,579,292 A 5/1971 Mallhaupt
(Continued)

FOREIGN PATENT DOCUMENTS

CN 101304786 A 11/2008
CN 205307712 U 6/2016
(Continued)

OTHER PUBLICATIONS

Adams, Roger, et al., "Platinum Oxide as a Catalyst in the Reduction of Organic Compounds. III. Preparation and Properties of the Oxide of Platinum Obtained by the Fusion of Chloroplatinic Acid with Sodium Nitrate," Journal of the American Chemical Society, Sep. 1923, vol. 45, pp. 2171-2179.

(Continued)

*Primary Examiner* — Samchuan C Yao
*Assistant Examiner* — Tina Zhang
(74) *Attorney, Agent, or Firm* — Edwin S. Flores; Daniel J. Chalker; Chalker Flores, LLP

(57) ABSTRACT

The present invention includes a device for hypoxia training including a breathable gas source; a mask in fluid communication with the breathable gas source; a mask-state detector that uses one or more criteria to determine if the mask is being worn by a subject, wherein the mask-state detector is capable of communicating an indication of a mask-off state (Continued)

or a mask-on state; a flowmeter in fluid communication with the mask and coupled to the mask-state detector; and a pressure regulator in fluid communication with the mask and with the breathable gas source, and coupled to the mask-state detector, wherein the pressure regulator sets a first pressure at the mask when the mask-state detector communicates an indication of a mask-off state or a second pressure at the mask when the mask-state detector communicates an indication of a mask-on state.

1 Claim, 49 Drawing Sheets

Related U.S. Application Data continuation-in-part of application No. 15/584,887, filed on May 2, 2017, now Pat. No. 11,071,840.

(60) Provisional application No. 62/336,426, filed on May 13, 2016.

(51) Int. Cl.
| | |
|---|---|
| *A61M 16/06* | (2006.01) |
| *A61M 16/12* | (2006.01) |
| *A61M 16/20* | (2006.01) |
| *A61M 16/22* | (2006.01) |
| *A62B 7/14* | (2006.01) |
| *A63B 23/18* | (2006.01) |
| *C25B 1/04* | (2021.01) |
| *C25B 9/23* | (2021.01) |
| *C25B 9/67* | (2021.01) |
| *C25B 15/02* | (2021.01) |
| *G09B 9/08* | (2006.01) |
| *G09B 9/16* | (2006.01) |
| *A61M 16/16* | (2006.01) |
| *H01M 8/04089* | (2016.01) |

(52) U.S. Cl.
CPC .......... *A61M 16/202* (2014.02); *A61M 16/22* (2013.01); *A62B 7/14* (2013.01); *A63B 23/18* (2013.01); *C25B 1/04* (2013.01); *C25B 9/23* (2021.01); *C25B 9/67* (2021.01); *C25B 15/02* (2013.01); *G09B 9/085* (2013.01); *G09B 9/165* (2013.01); *A61M 2016/0015* (2013.01); *A61M 2016/0027* (2013.01); *A61M 2016/003* (2013.01); *A61M 16/06* (2013.01); *A61M 2016/1025* (2013.01); *A61M 16/106* (2014.02); *A61M 16/1085* (2014.02); *A61M 16/12* (2013.01); *A61M 16/16* (2013.01); *A61M 16/209* (2014.02); *A61M 2202/0208* (2013.01); *A61M 2205/13* (2013.01); *A61M 2205/3344* (2013.01); *A61M 2205/502* (2013.01); *A61M 2205/52* (2013.01); *A61M 2230/10* (2013.01); *A61M 2230/205* (2013.01); *A61M 2230/42* (2013.01); *A63B 2208/05* (2013.01); *A63B 2213/006* (2013.01); *A63B 2220/56* (2013.01); *H01M 8/04089* (2013.01)

(58) Field of Classification Search
CPC ............... A61M 16/06; A61M 16/106; A61M 16/1085; A61M 16/12; A61M 16/16; A61M 16/209; A61M 2016/0015; A61M 2016/0027; A61M 2016/003; A61M 2016/1025; A61M 2202/0208; A61M 2205/13; A61M 2205/3344; A61M 2205/502; A61M 2205/52; A61M 2230/10; A61M 2230/205; A61M 2230/42; A62B 7/14; A62B 7/02; A62B 9/006; A62B 9/00; A62B 7/00; A62B 19/00; A63B 23/18; A63B 2208/05; A63B 2213/006; A63B 2220/56; A63B 2220/00; A63B 2230/425; C25B 1/04; C25B 9/23; C25B 9/67; C25B 15/02; G09B 9/085; G09B 9/165; H01M 8/04089; Y02E 60/36; Y02E 60/50; A61G 10/023
USPC .............. 434/29, 30, 37, 53, 59; 128/205.11
See application file for complete search history.

(56) References Cited

U.S. PATENT DOCUMENTS

| | | |
|---|---|---|
| 4,086,923 A | 5/1978 | Henkin |
| 4,539,086 A | 9/1985 | Fujita et al. |
| 5,338,412 A | 8/1994 | Burk et al. |
| 5,924,419 A | 7/1999 | Kotliar |
| 5,988,161 A | 11/1999 | Kroll |
| 6,165,105 A | 12/2000 | Boutellier et al. |
| 6,171,368 B1 | 1/2001 | Maget et al. |
| 6,179,986 B1 | 1/2001 | Swette et al. |
| 6,536,429 B1 | 3/2003 | Pavlov |
| 6,871,645 B2 | 3/2005 | Wartman et al. |
| 7,125,625 B2 | 10/2006 | Cisar et al. |
| 7,632,338 B2 | 12/2009 | Cipollini |
| 8,465,630 B2 | 6/2013 | Reed et al. |
| 2002/0139368 A1 | 10/2002 | Bachinski |
| 2003/0022200 A1 | 1/2003 | Mssing et al. |
| 2003/0070678 A1 | 4/2003 | Wartman et al. |
| 2004/0101723 A1 | 5/2004 | Kruppa et al. |
| 2004/0134493 A1 | 7/2004 | McCombs |
| 2004/0185235 A1 | 9/2004 | Faguy et al. |
| 2005/0136299 A1 | 6/2005 | Richey et al. |
| 2006/0225572 A1 | 10/2006 | Kutt et al. |
| 2007/0077200 A1 | 4/2007 | Baker |
| 2007/0119456 A1 | 5/2007 | Scott et al. |
| 2007/0181128 A1 | 8/2007 | Stroetz |
| 2007/0221225 A1 | 9/2007 | Kutt et al. |
| 2007/0034507 A1 | 12/2007 | Sin et al. |
| 2008/0202774 A1 | 8/2008 | Kotliar |
| 2009/0183738 A1 | 7/2009 | Kostin |
| 2010/0065440 A1 | 3/2010 | Nishimura et al. |
| 2012/0241315 A1 | 9/2012 | Yoshinaga et al. |
| 2013/0026195 A1 | 1/2013 | Park et al. |
| 2013/0053541 A1 | 2/2013 | Shankar et al. |
| 2013/0340760 A1 | 12/2013 | Brumley et al. |
| 2014/0069429 A1 | 3/2014 | Lucci et al. |
| 2014/0131217 A1 | 5/2014 | Buschmann |
| 2014/0322675 A1 | 10/2014 | Bassovitch |
| 2015/0323411 A1 | 11/2015 | Eberlein |
| 2016/0095994 A1 | 4/2016 | Currin |
| 2016/0118679 A1 | 4/2016 | Joos et al. |
| 2016/0144973 A1 | 5/2016 | Darling et al. |
| 2016/0175623 A1* | 6/2016 | Alexander ............. G09B 23/28 434/262 |
| 2016/0190631 A1 | 6/2016 | Dristy |
| 2016/0273116 A1 | 9/2016 | Gilliam et al. |
| 2016/0376712 A1 | 12/2016 | Ono et al. |
| 2017/0152605 A1 | 6/2017 | Izgorodin et al. |
| 2017/0271089 A1 | 9/2017 | Ono et al. |
| 2018/0296877 A1 | 10/2018 | Reeh et al. |

FOREIGN PATENT DOCUMENTS

| | | |
|---|---|---|
| EP | 661071 A1 | 7/1995 |
| GB | 2276458 A | 3/1994 |
| GB | 2558847 A | 7/2018 |
| JP | S61117103 A | 6/1986 |
| JP | 2008543384 A | 12/2008 |
| KR | 1020110124814 A | 11/2011 |
| WO | 1993023102 A1 | 11/1993 |

(56) References Cited

FOREIGN PATENT DOCUMENTS

| WO | 199834683 A1 | 8/1998 |
|---|---|---|
| WO | 2003024505 A3 | 3/2003 |

OTHER PUBLICATIONS

Artino, R. A., et al., "Mask-On Hypoxia Training for Tactical Jet Aviators: Evaluation of an Alternate Instructional Paradigm." Aviation, Space, and Environmental Medicine, Aug. 2006, vol. 77, No. 8, pp. 857-863.

Artino, R. A., et al., "Normobaric Hypoxia Training: The Effects of Breathing-Gas Flow Rate on Symptoms." Aviation, Space, and Environmental Medicine, Jun. 2009, vol. 80, No. 6, pp. 547-552.

Carothers, Wallace, et al., "Platinum Oxide as a Catalyst in the Reduction of Organic Compounds. II. Reduction of Aldehydes. Activation of the Catalyst by the Salts of Certain Metals," Journal of the American Chemical Society, Feb. 23, 1923, vol. 45, pp. 1071-1086.

EPO search report of EP 17796576.1 dated Jan. 3, 2019, 13 pp.

Files, D.S., et al., "Depressurization in Military Aircrafts: Rates, Rapidity, and Health Effects for 1055 incidents," Aiation, Space, and Environmental Medicine, Jun. 2005, vol. 76, No. 6, pp. 523-529.

Fujita, Y., et al., "An electrochemical oxygen separator using an ion-exchange membrane as the electrolyte." Journal of Applied Electrochemistry, Feb. 14, 1986, vol. 16, pp. 935-940.

Katsounaros, I., et al., "Oxygen Electrochemistry as a Cornerstone for Sustainable Energy Conversion," Angew. Chem. Int. Ed., 2014, vol. 53, pp. 102-121.

Owe, Lars-Erik, et al., "Iridium-ruthenium single phase mixed oxides for oxygen evolution: Composition dependence of electrocatalytic activity," Electrochimica Acta, vol. 70, Mar. 10, 2012, pp. 158-164.

Sausen, P. K., et al., "A Closed-Loop Reduced Oxygen Breathing Device for Inducing Hypoxia In Humans." Aviation, Space, and Environmental Medicine, Nov. 2003, vol. 74, No. 11, pp. 1190-1197.

Voorhees, V., et al., "Oxides of Platinum in Organic Reductions, The Use of the Oxides of Platinum for the Catalytic Reduction of Organic Compounds. I," Journal of the American Chemical Society, vol. 44, Apr. 10, 1922, pp. 1397-1405.

Westerman, A. R., "Hypoxia familiarisation training by the reduced oxygen breathing method." ADF Health, Apr. 2004, vol. 5, pp. 11-15.

International Search Report and Written Opinion for PCT/US2017/030634 dated Sep. 12, 2017, 15 pp.

International Search Report and Written Opinion by the Korean Intellectual Property Office for PCT/US2019/030868 dated Oct. 8, 2019, 15 pp.

\* cited by examiner

HYPOXIA TRAINING DEVICE

CROSS-REFERENCE TO RELATED APPLICATIONS

This application is a continuation application of and claims priority to U.S. patent application Ser. No. 15/975,301 filed on May 9, 2018, which is a continuation-in-part application of and claims priority to U.S. patent application Ser. No. 15/584,887 filed on May 2, 2017 and entitled "Hypoxia Training Device," which is a non-provisional patent application of U.S. Provisional Application Ser. No. 62/336,426 filed on May 13, 2016, the entire contents of which are incorporated herein by reference.

STATEMENT OF FEDERALLY FUNDED RESEARCH

This invention was made with government support under contract numbers N68335-14-C-0068 and N68335-15-C-0050 awarded by the United States Navy. The government has certain rights in the invention.

TECHNICAL FIELD OF THE INVENTION

The present invention relates in general to the field of devices and methods for training at high altitude, and more particularly, to a device and method for hypoxia training.

BACKGROUND OF THE INVENTION

Without limiting the scope of the invention, its background is described in connection with hypoxia training devices.

High altitude flight presents many risks to pilots including hypoxia, which severely affects the pilot's cognitive function. In aviation, hypoxia is developed due to low air pressure and thus low oxygen partial pressure at high altitudes. If not recognized and corrected, hypoxia will cause the pilot to lose consciousness and control of the aircraft. Based on a recent USAF publication, from 1981 to 2003, over 1000 hypoxia related incidents (of which 350 cases involved adverse health effects) occurred within US military aircraft pilots. Early recognition of hypoxic conditions is paramount to implementing corrective action and avoiding catastrophe and this can only be achieved through extensive hypoxia training.

Currently, hypoxia training for pilots has been a very limited effort in the US military due to insufficient number of mobile hypoxia training devices and the difficulty of integrating these conventional training devices with flight simulator software. Historically, Low-Pressure Chamber (LPC) technology has been used to simulate high altitude environments for pilot hypoxia training. However, training in these hypobaric chambers is costly, time consuming, and exposes the trainees to risks of decompression sickness, barotraumas, and other dysbarisms. Recently, normobaric training devices, such as the Reduced-Oxygen Breathing Device (ROBD) have been successfully used for training without the risks associated with LPCs. These devices simulate high altitude atmosphere by delivering oxygen depleted air to the trainee at standard atmospheric pressure via an oxygen mask. Ideally, this training device would be implemented in conjunction with an existing full motion flight simulator to realistically mimic in-flight failures. However, these devices are currently too bulky for integration with full motion flight simulators and impose heavy logistical burdens on the training facilities including the replacement of large compressed gas cylinders and the need for CO2 absorption canisters. Additionally, most current reduced oxygen breathing devices provide fixed gas flow rates resulting in air starvation of the trainees. A mobile, low maintenance hypoxia training device with pressure demand delivery is needed for integration into existing full-motion flight simulators to increase training quality and efficiency.

SUMMARY OF THE INVENTION

The present invention includes a device for hypoxia training, including a breathable gas source; a mask in fluid communication with the breathable gas source; a mask-state detector that uses one or more criteria to determine if the mask is being worn by a subject, wherein the mask-state detector is capable of communicating an indication of a mask-off state or a mask-on state; a flowmeter in fluid communication with the mask and coupled to the mask-state detector; and a pressure regulator in fluid communication with the mask and with the breathable gas source, and coupled to the mask-state detector, wherein the pressure regulator sets a first pressure at the mask when the mask-state detector communicates an indication of a mask-off state or a second pressure at the mask when the mask-state detector communicates an indication of a mask-on state. In one aspect, the mask-state detector determines if the mask is being worn by a subject periodically during operation of the device. In another aspect, the one or more criteria include: a flow rate at the mask; a rate of change of flow at the mask, an outlet pressure, a change in outlet pressure, or a system pressure. In another aspect, the one or more criteria include: a flow rate at the mask of less than approximately 70 slpm; a change of flow rate at the mask of less than approximately 2 slpm; an outlet pressure of less than approximately 1.5 inches $H_2O$; or a change in outlet pressure of less than approximately 0.4 inches $H_2O$. In another aspect, the mask-state detector determines if the mask is being worn by a subject after a preselected number of samples of one or more of the criteria. In another aspect, the one or more criteria are sufficient to distinguish a mask-off state and the subject's long inhalation or deep inhalation during a mask-on state. In another aspect, the mask-state detector communicates an indication of mask-transition state for a pre-selected time after the mask-state detector detects a change from a mask-off state to a mask-on state or from a mask-on state to a mask-off state. In another aspect, the first pressure set at the mask, when the mask-state detector communicates an indication of a mask-off state, is approximately 0.075 inches $H_2O$. In another aspect, the second pressure set at the mask when the mask-state detector communicates an indication of a mask-on state is approximately 1.5 inches $H_2O$. In another aspect, the device further includes a pressure transducer in fluid communication with the breathable gas source, wherein the pressure transducer regulates a breathable gas pressure at the output from the breathable gas source; a back pressure regulator in fluid communication with the pressure regulator, wherein the back pressure regulator maintains a preselected maximum breathable gas pressure by venting breathable gas if the preselected maximum breathable gas-pressure is reached; and one or more high-pressure accumulator volumes in fluid communication with the back-pressure regulator and the pressure transducer, wherein the one or more high-pressure accumulator volumes each store breathable gas. In another aspect, the pressure transducer regulates the breathable gas pressure at the breathable gas source at approximately 15 psi. In another aspect, the device is configured for use with a flight simulator.

The present invention also includes a device for hypoxia training including a breathable gas source including a pressure swing adsorption device, a vacuum pressure swing adsorption device, oxygen separation polymer membranes, a solid inorganic oxide ceramic membrane an ion transport membrane, a cryogenic device that produces oxygen, or a MOLTOX™ chemical oxygen separator; a mask in fluid communication with the breathable gas source; a mask-state detector that uses one or more criteria to determine if the mask is being worn by a subject, wherein the mask-state detector is capable of communicating an indication of a mask-off state or a mask-on state; a flowmeter in fluid communication with the mask and coupled to the mask-state detector; and a pressure regulator in fluid communication with the mask and with the breathable gas source, and coupled to the mask-state detector, wherein the pressure regulator sets a first pressure at the mask when the mask-state detector communicates an indication of a mask-off state or a second pressure at the mask when the mask-state detector communicates an indication of a mask-on state. In one aspect, the device is configured for use with a flight simulator.

The present invention also includes a method of regulating pressure in a hypoxia training system including providing a device to a subject during hypoxia training that includes: a breathable gas source; a mask in fluid communication with the breathable gas source; a mask-state detector that uses one or more criteria to determine if the mask is being worn by a subject, wherein the mask-state detector is capable of communicating an indication of a mask-off state or a mask-on state; a flowmeter in fluid communication with the mask and coupled to the mask-state detector; and a pressure regulator in fluid communication with the mask and with the breathable gas source, and coupled to the mask-state detector, wherein the pressure regulator sets a first pressure at the mask when the mask-state detector communicates an indication of a mask-off state or a second pressure at the mask when the mask-state detector communicates an indication of a mask-on state; and setting a first pressure at the mask when the mask-state detector communicates an indication of a mask-off state or a second pressure at the mask when the mask-state detector communicates an indication of a mask-on state. In one aspect, the mask-state detector determines if the mask is being worn by a subject periodically during operation of the device. In another aspect, the one or more criteria include: a flow rate at the mask; a rate of change of flow at the mask, an outlet pressure, a change in outlet pressure, or a system pressure. In another aspect, the one or more criteria include: a flow rate at the mask of less than approximately 70 slpm; a change of flow rate at the mask of less than approximately 2 slpm; an outlet pressure of less than approximately 1.5 inches $H_2O$; or a change in outlet pressure of less than approximately 0.4 inches $H_2O$. In another aspect, the mask-state detector determines if the mask is being worn by a subject after a preselected number of samples of one or more of the criteria. In another aspect, the one or more criteria are sufficient to distinguish a mask-off state and the subject's long inhalation or deep inhalation during a mask-on state. In another aspect, the mask-state detector communicates an indication of mask-transition state for a pre-selected time after the mask-state detector detects a change from a mask-off state to a mask-on state or from a mask-on state to a mask-off state. In another aspect, the first pressure set at the mask when the mask-state detector communicates an indication of a mask-off state is approximately 0.075 inches $H_2O$. In another aspect, the second pressure set at the mask when the mask-state detector communicates an indication of a mask-on state is approximately 1.5 inches $H_2O$. In another aspect, the device further includes a pressure transducer in fluid communication with the breathable gas source, wherein the pressure transducer regulates a breathable gas pressure at the breathable gas source; a back pressure regulator in fluid communication with the pressure regulator, wherein the back pressure regulator maintains a preselected maximum breathable gas pressure by venting breathable gas if the preselected maximum breathable gas-pressure is reached; and one or more high-pressure accumulator volumes in fluid communication with the back-pressure regulator and the pressure transducer, wherein the one or more high-pressure accumulator volumes each store breathable gas. In another aspect, the pressure transducer regulates the breathable gas pressure at the breathable gas source at approximately 15 psi. In another aspect, the method further includes using the device with a flight simulator. The present invention also includes a device for hypoxia training including an oxygen-depleted breathable gas source; a switching valve in fluid communication with the oxygen-depleted breathable gas source; an oxygen pump for delivering oxygenated breathable gas or normal breathable gas, the oxygen pump in fluid communication with the switching valve; a low-pressure accumulated volume in fluid communication with the oxygen pump; a normal breathable gas source in fluid communication with the low-pressure accumulated volume; an oxygen source in fluid communication with the low-pressure accumulated volume; a high-pressure accumulated volume in fluid communication with the switching valve; a forward pressure regulator in fluid communication with the high-pressure accumulated volume; and a mask in fluid communication with the forward pressure regulator. In one aspect, the device further includes a bladder in fluid communication with the low-pressure accumulated volume, wherein: in a normal mode, oxygen is stored in the bladder; and in an oxygen recovery mode, the bladder supplies oxygen to supplement oxygen from the oxygen source. In another aspect, in the oxygen recovery mode, the normal breathable gas source supplies breathable gas to supplement the oxygen source. In another aspect, the device for hypoxia training further includes a bidirectional pressure control in fluid communication with the normal breathable gas source and the low-pressure accumulated volume and configured to vent excess pressure and to supply normal breathable gas when needed to supplement oxygen from the oxygen source in an oxygen recovery mode. In another aspect, the device for hypoxia training further includes a back pressure regulator in fluid communication with the oxygen pump and the low-pressure accumulated volume and configured to cycle excess oxygen from the oxygen pump to the low-pressure accumulated volume. In another aspect, the device for hypoxia training further includes a control interface coupled at least to the oxygen pump and the switching valve and configured to accept manual input at least to enable or disable the oxygen pump or to actuate the switching valve. In another aspect, the device for hypoxia training further includes a switch box coupled to the control interface and configured to accept manual input at least to actuate the switching valve. In another aspect, the device is configured for use with a flight simulator.

The present invention also includes a method of controlling the level of oxygen in a breathable gas stream during hypoxia training, including providing a device to a subject during hypoxia training that includes: an oxygen-depleted breathable gas source; a switching valve in fluid communication with oxygen-depleted breathable gas source; an oxygen pump for delivering oxygenated breathable gas or normal breathable gas, the oxygen pump in fluid communication with the switching valve; a low-pressure accumulated volume in fluid communication with the oxygen pump; a normal breathable gas source in fluid communication with the low-pressure accumulated volume; an oxygen source in fluid communication with the low-pressure accumulated volume; a high-pressure accumulated volume in fluid communication with the switching valve; a forward pressure regulator in fluid communication with the high-pressure accumulated volume; and a mask in fluid communication with the forward pressure regulator; and modulating the amount of oxygen output from the device at the mask during operation. In one aspect, the device further includes a bladder in fluid communication with the low-pressure accumulated volume, wherein: in a normal mode, oxygen is stored in the bladder; and in an oxygen recovery mode, the bladder supplies oxygen to supplement oxygen from the oxygen source. In another aspect, in the oxygen recovery mode, the normal breathable gas source supplies breathable gas to supplement the oxygen source. In another aspect, the device further includes a bidirectional pressure control in fluid communication with the normal breathable gas source and the low-pressure accumulated volume and configured to vent excess pressure and to supply normal breathable gas when needed to supplement oxygen from the oxygen source. In another aspect, the device further includes a back pressure regulator in fluid communication with the oxygen pump and the low-pressure accumulated volume and configured to cycle excess oxygen from the oxygen pump to the low-pressure accumulated volume. In another aspect, the device further includes a control interface coupled at least to the oxygen pump and the switching valve and configured to accept manual input at least to enable or disable the oxygen pump or to actuate the switching valve. In another aspect, the device further includes a switch box coupled to the control interface and configured to accept manual input at least to actuate the switching valve. In another aspect, the method of controlling the level of oxygen in a breathable gas stream during hypoxia training further includes using the device with a flight simulator.

The present invention also includes a method of recovering from or avoiding hypoxia, including using a device for hypoxia training including: an oxygen-depleted breathable gas source; a switching valve in fluid communication with oxygen-depleted breathable gas source; an oxygen pump for delivering oxygenated breathable gas or normal breathable gas, the oxygen pump in fluid communication with the switching valve; a low-pressure accumulated volume in fluid communication with the oxygen pump; a normal breathable gas source in fluid communication with the low-pressure accumulated volume; an oxygen source in fluid communication with the low-pressure accumulated volume; a high-pressure accumulated volume in fluid communication with the switching valve; a forward pressure regulator in fluid communication with the high-pressure accumulated volume; and a mask in fluid communication with the forward pressure regulator; recognizing at least one symptom of hypoxia, hyperventilation, hyperoxia, or exposure to chemicals; and switching the switching valve to an oxygen recovery mode to increase oxygen to the mask by supplying pure oxygen, atmospheric air, reduced oxygen air or oxygen enriched air. In one aspect, the device further includes a bladder in fluid communication with the low-pressure accumulated volume. In another aspect, the device is adapted for use with a flight simulator.

The present invention also includes a method of regulating a breathable gas pressure in a device for supplying breathable gas to a user through a mask including sampling at least one measurement including: a flow rate of the breathable gas; a change in the flow rate of the breathable gas; a breathable gas pressure; and a change in the breathable gas pressure; comparing at least one sampled measurement to a respective preselected range; counting the number of the at least one sampled measurements that falls within the respective preselected range within a preselected period of time; determining an appropriate breathable gas pressure from the at least one sampled measurement that falls within the respective preselected range within a preselected period of time; and setting the breathable gas pressure substantially at the appropriate breathable gas pressure. In one aspect, the respective preselected range includes: a flow rate of the breathable gas greater than approximately 70 standard liters per minute; a change in the flow rate of the breathable gas less than approximately 2 slpm; a breathable gas pressure less than 1.5 or 3.0 inches $H_2O$; and a change in the breathable gas pressure less than approximately 0.4 inches $H_2O$. In another aspect, the device is adapted for use with a flight simulator.

The present invention also includes a hypoxia training device for use with a commercial-aviation breathing mask including an oxygen-depleted breathable gas source; a switching valve in fluid communication with the oxygen-depleted breathable gas source; an oxygen pump for delivering oxygenated breathable gas or normal breathable gas, the oxygen pump in fluid communication with the switching valve; a booster pump adapted to supply oxygen-depleted breathable gas, oxygenated breathable gas, or normal breathable gas at a pressure of at least approximately 60 psi; a water knock-out; a high-pressure accumulated volume in fluid communication with the oxygen pump; a normal breathable gas source in fluid communication with the low-pressure accumulated volume; an oxygen source in fluid communication with the low-pressure accumulated volume; a high-pressure accumulated volume in fluid communication with the switching valve; a forward pressure regulator in fluid communication with the high-pressure accumulated volume; and a mask in fluid communication with the forward pressure regulator; wherein the hypoxia training device is adapted to operate in at least two recovery modes, a first recovery mode in which the breathable gas supplied to the mask is pure oxygen at a negative pressure, and a second recovery mode in which the breathable gas supplied to the mask is pure oxygen at a positive pressure. In one aspect, the device further includes a bladder in fluid communication with the low-pressure accumulated volume. In another aspect, the device is adapted to be switched to the first recovery mode or the second recovery mode while the device is being operated. In another aspect, in operation in the first mode, the forward pressure regulator is set to a negative pressure bias. In another aspect, in operation in the second recovery mode, a preselected range of breathable gas pressure is less than approximately 3.0 inches $H_2O$. In another aspect, the device is configured for use with a flight simulator.

The present invention also includes a method of collecting and storing breathing information, including noting a first time at which a breathable gas flow rate rises above a preselected threshold rate; noting a second time at which a peak breathable gas flow rate occurs after the first time;

storing a sum of the breathable gas flow rate multiplied by a change in time since a previous peak breathable gas flow rate; noting a third time at which the breathable gas flow rate next rises above the threshold rate after the first time; storing a difference between the third time and the first time as a length of a breath that begins at the first time; storing at least the length of the breath that begins at the first time, the peak breathable gas flow rate, an integration of the breathable gas flow rate over time, and a calculated average breath frequency over a preselected number of breaths or a preselected period of time; and displaying at least one of the length of the breath that began at the first time, the peak breathable gas flow rate, the integration of the breathable gas flow rate over time, and the calculated average breath frequency over a preselected number of breaths or a preselected period of time.

The present invention also includes a training device that simulates one or more oxygen malfunctions in aircraft flight, including: a training device configured to be operably coupled to a flight simulator, the training device including: an oxygen-depleted breathable gas source; a switching valve in fluid communication with the oxygen-depleted breathable gas source; an oxygen pump for delivering oxygenated breathable gas or normal breathable gas, the oxygen pump in fluid communication with the switching valve; a low-pressure accumulated volume in fluid communication with the oxygen pump; a normal breathable gas source in fluid communication with the low-pressure accumulated volume; an oxygen source in fluid communication with the low-pressure accumulated volume; a high-pressure accumulated volume in fluid communication with the switching valve; a forward pressure regulator in fluid communication with the high-pressure accumulated volume; and wherein the training device is configured to disrupt a supply of breathable gas to the mask by providing reduced oxygen breathable gas to the mask or by modifying a breathable gas flow rate to the mask; wherein the training device is configured to monitor one or more physiological or cognitive responses of a subject wearing the mask or to allow one or more physiological or cognitive responses of a subject wearing the mask to be monitored; and wherein the training device is configured to permit the subject wearing the mask or an attendant or an operators of the training device to correct a oxygen malfunction in simulated aircraft flight.

In one embodiment the present invention includes a device for hypoxia training including: one or more electrochemical cells each including: a cathode and an anode separated by a proton exchange membrane, each of the anode and cathode in communication with an input and an output, wherein the input of the cathode is in fluid communication with ambient air, and wherein the input of the anode is in fluid communication with a source of liquid water; a power supply connected to the one or more electrochemical cells; and a mask in fluid communication with the output from the cathode of the one or more electrochemical cells, wherein oxygen is removed from the ambient air during contact with the cathode when hydrogen ions separated from liquid water by a catalyst on the anode convert oxygen in the ambient air into water. In one aspect, the anode catalyst is an electrocatalyst and wherein water molecules that contact the electrocatalyst are dissociated into hydrogen protons and oxygen by electrolysis, wherein the protons traverse the proton exchange membrane to the cathode, and oxygen in the ambient air is reacted with protons at the cathode into water. In another aspect, the device further includes an oxygen sensor in fluid communication with the output from the cathode and connected to a processor that determines the amount of oxygen in the output, wherein the processor controls the power to the electrochemical cell based on the amount of oxygen detected and one or more settings for hypoxia training. In another aspect, the device further includes one or more pumps and valves in fluid communication with the anode and cathode, wherein the one or more pumps and valves control air flow to and from the cathode, and water flow into the anode, wherein the pumps and valves regulate the reduction in oxygen from ambient air and the air flow to the mask and the conversion of water into oxygen. In another aspect, the device further includes a temperature regulator for the electrochemical cell, wherein the temperature is reduce by contacting the electrochemical cell with a coolant. In another aspect, the device is defined further as a pressure-on-demand device, wherein a reduction in the amount of oxygen removed from the ambient air by the electrochemical cell is controlled based on air intake at the mask, wherein air intake is determined by one or more sensors that monitor breath rate, wherein the one or more sensors are connected to a control logic that adjusts the current to the electrochemical stack in real time. In another aspect, the logic determines how much air is inhaled at the mask, a peak amplitude of the air and a breath rate, and a mass flow controller adjusts the air intake at the mask available to a user. In another aspect, the electrochemical cell includes a stack of anodes and cathodes. In another aspect, the power supply is defined further as a hybrid power distribution system that limits current draw from an external power source. In another aspect, the device further includes a water recovery system in fluid communication with the cathode, wherein the water in the water recovery system can be at least one of: delivered to the anode, stored, or disposed. In another aspect, the e anode catalyst is an Ir-Ru-Ox catalyst with at least one of Au or Pt nanoparticles. In another aspect, the anode catalyst is an Ir-Ru-Ox catalyst with a 5 to 95 mol % Ir to Ru ratio. In another aspect, the anode catalyst is an Ir-Ru-Ox catalyst that further includes at least one of an Au loading range of 0, 1, 5, 10, 15, 20, 25, 30, 35, 40 wt %, or a Pt loading of from 0, 5, 10, 15, 20 wt %. In another aspect, the cathode further includes a cathode electrochemical catalyst that reduces oxygen in the ambient air. In another aspect, the cathode has a first and a second side, and the first side is in contact with the proton exchange membrane and the second side is in contact with an air diffusion layer, wherein the air diffusion layer is in contact with the cathode input and output. In another aspect, the anode has a first and a second side, and the first side is in contact with the proton exchange membrane and the second side is in contact with a water flow layer, wherein the water flow layer is in contact with the anode input and output. In another aspect, the electrocatalyst demonstrates a greater than 65%, 70%, 75%, 80%, or 85% water electrolysis efficiency. In another aspect, an ion exchange resin is positioned between the source of water and the anode.

In another embodiment the present invention includes a method of controlling the level of oxygen is an air stream during pilot hypoxia training including: providing a device to a pilot during hypoxia training that includes: one or more electrochemical cells each including: a cathode and an anode separated by a proton exchange membrane, each of the anode and cathode in communication with an input and an output, wherein the input of the cathode is in fluid communication with ambient air, and wherein the input of the anode is in fluid communication with a source of liquid water; a power supply connected to the one or more electrochemical cells; and a mask in fluid communication with the output from the cathode of the one or more electrochemical cells, wherein oxygen is removed from the ambient air during contact with the cathode when hydrogen ions are separated from liquid water by a catalyst on the anode; and measuring one or more parameters of oxygen use at the mask, wherein the parameters are processed by a logic that controls the current to the one or more electrochemical cells; and modulating the amount of oxygen output from the device during operation. In one aspect, the anode catalyst is an electrocatalyst and further including contacting water molecules with the electrocatalyst, wherein the water molecules are dissociated into hydrogen protons and oxygen by electrolysis, wherein the protons traverse the proton exchange membrane to the cathode and oxygen at the cathode is converted into water by catalysis of the hydrogen and oxygen. In another aspect, the method further includes using an oxygen sensor in fluid communication with the output from the cathode and connected to a processor that determines the amount of oxygen in the output, wherein the processor controls the power to the electrochemical cell based on the amount of oxygen detected and one or more settings for hypoxia training. In another aspect, the method further includes controlling one or more pumps and valves in fluid communication with the anode and cathode with a processor, wherein the one or more pumps and valves control air flow to and from the cathode, and water flow into the anode, wherein the pumps and valves regulate the reduction in oxygen from ambient air and the air flow to the mask and the conversion of water into oxygen. In another aspect, the method further includes regulating the temperature of the electrochemical cell by contacting the electrochemical cell with a coolant. In another aspect, the method further includes regulating oxygen pressure-on-demand, wherein the amount of oxygen removed from the ambient air is reduced by the electrochemical cell based on air intake at the mask, wherein air intake is determined by one or more sensors that monitor breath rate, wherein the one or more sensors are connected to that logic, which logic adjusts the current to the electrochemical stack in real time. In another aspect, the method further includes determining how much air is inhaled at the mask with the logic, wherein the logic provides a peak amplitude based on the breath rate, and adjusts a mass flow controller for ambient air intake at the mask. In another aspect, the electrochemical cell includes a stack of anodes and cathodes. In another aspect, the power supply is defined further as a hybrid power distribution system that limits current draw from an external power source. In another aspect, the method further includes recovering water with a water recovery system in fluid communication with the cathode, wherein the water in the water recovery system can be at least one of: delivered to the anode, stored, or disposed. In another aspect, the anode catalyst is an Ir-Ru-Ox catalyst with at least one of Au or Pt nanoparticles. In another aspect, the anode catalyst is an Ir-Ru-Ox catalyst with a 5 to 95 mol % Ir to Ru ratio. In another aspect, the anode catalyst is an Ir-Ru-Ox catalyst that further includes at least one of an Au loading range of 0, 1, 5, 10, 15, 20, 25, 30, 35, 40 wt %, or a Pt loading of from 0, 5, 10, 15, 20 wt %. In another aspect, the cathode further includes a cathode electrochemical catalyst that reduces oxygen in the ambient air. In another aspect, the cathode has a first and a second side, and the first side is in contact with the proton exchange membrane and the second side is in contact with an air diffusion layer, wherein the air diffusion layer is in contact with the cathode input and output. In another aspect, the anode has a first and a second side, and the first side is in contact with the proton exchange membrane and the second side is in contact with a water flow layer, wherein the water flow layer is in contact with the anode input and output. In another aspect, the electrocatalyst demonstrates a greater than 65%, 70%, 75%, 80%, or 85% water electrolysis efficiency. In another aspect, the method further contacting includes water with an ion exchange resin prior to contacting with the anode.

In yet another embodiment the present invention includes a system for training a pilot for hypoxia, the system including: providing a device to a pilot during hypoxia training that includes: one or more electrochemical cells each including: a cathode and an anode separated by a proton exchange membrane, each of the anode and cathode in communication with an input and an output, wherein the input of the cathode is in fluid communication with ambient air, and wherein the input of the anode is in fluid communication with a source of liquid water; a power supply connected to the one or more electrochemical cells; and a mask in fluid communication with the output from the cathode of the one or more electrochemical cells, wherein oxygen is removed from the ambient air during contact with the cathode when hydrogen ions are separated from liquid water by a catalyst on the anode; and measuring one or more parameters of oxygen use at the mask with one or more sensors connected to a processor, wherein an output from the sensors is processed by a logic in the processor, wherein the processor that controls a current to the one or more electrochemical cells; modulating the amount of oxygen output from the device during operation; and a display connected to the processor, wherein the display provides instructions to the pilot to change one or more parameters selected from at least one of breathing depth, breathing frequency, breathing cadence, muscle tension, suit pressure, or from of oxygen from a non-ambient source.

Another embodiment the present invention includes a device for reducing the amount of oxygen in ambient air including: one or more electrochemical stacks including: a cathode electrocatalyst, a proton exchange membrane, and an anode electrocatalyst, wherein when power is provided to the one or more electrochemical stacks, the anode electrocatalyst electrolyzes water into protons and oxygen, the protons traverse the hydrogen exchange membrane, and the cathode electrocatalyst reacts the protons with oxygen in ambient air to form water, thereby reducing the amount of oxygen in the ambient air.

The present invention also includes a method for reducing the amount of oxygen in ambient air including: electrically powering one or more electrochemical stacks that include: a cathode electrocatalyst, a proton exchange membrane, and an anode electrocatalyst; electrolyzing water at the anode electrocatalyst into protons and oxygen, wherein the protons traverse the hydrogen exchange membrane by attraction to the cathode, and reacting oxygen in ambient air with the protons at the cathode electrocatalyst to form water, thereby reducing the amount of oxygen in the ambient air.

In yet another embodiment the present invention includes a gas generator including: electrically powering one or more electrochemical stacks that include: a cathode electrocatalyst, a proton exchange membrane, and an anode electrocatalyst; electrolyzing water at the anode electrocatalyst into protons and oxygen, wherein the protons are eliminated by traversing the hydrogen exchange membrane by attraction to the cathode and pure oxygen is generated. In another aspect, the generator is connected to a compressor that compresses the oxygen to 0 to 400 psi, 400 to 2200 psi, or 2200 to 3600. In another aspect, the oxygen is concentrated by reacting the protons and electrons transferred to the cathode and reacted with oxygen in the air feed to generate a nitrogen enriched air stream at the cathode side. In another aspect, the nitrogen enriched air is applied to render materials inert. In another aspect, the protons generated are recombined at the cathode into hydrogen gas. In another aspect, the protons generated are recombined at the cathode into compressed hydrogen gas and the oxygen is vented out at ambient pressures. In another aspect, the one or more of the following gases can be detected at the electrocatalyst by measuring changes in pH: nitrous oxides, ammonia, carbon monoxide, or carbon dioxide.

Yet another embodiment of the present invention is a device for hypoxia training including: an accumulator in fluid communication with a gas inlet and a back pressure regulator at a first output and a forward pressure regulator at a second output; a conduit connected to an output of the forward pressure regulator that connects to an inlet of a unidirectional valve at a mask, the mask being further connected to a unidirectional output valve; and a pressure sensor in communication with an interior of the conduit, wherein the pressure sensor is connected to and controls the forward pressure regulator to control the flow of gas from the accumulator to the mask.

Another embodiment of the present invention is a method for hypoxia training including: providing an accumulator in fluid communication with a gas inlet and a back pressure regulator at a first output and a forward pressure regulator at a second output; connecting a conduit to an output of the forward pressure regulator that connects to an inlet of a unidirectional valve at a mask, the mask being further connected to a unidirectional output valve; and providing a pressure sensor in communication with an interior of the conduit, wherein the pressure sensor is connected to and controls the forward pressure regulator to control the flow of gas from the accumulator to the mask.

BRIEF DESCRIPTION OF THE DRAWINGS

For a more complete understanding of the features and advantages of the present invention, reference is now made to the detailed description of the invention along with the accompanying figures and in which.

DETAILED DESCRIPTION OF THE INVENTION

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

The present invention is an electrochemical oxygen separation (EOS) device that is based on liquid water fed electrochemical cells that utilize an advanced and highly efficient oxygen evolution reaction (OER) electrocatalyst. A membrane electrode assembly (MEA), which is one of the components of the electrochemical cell, is used to separate the oxygen from the nitrogen present in the ambient air via a series of electrochemical reactions. Liquid water is fed to the anode compartment of the electrochemical cell, while air is fed to the cathode compartment. At the cathode, oxygen is removed from the air stream resulting in an oxygen depleted stream which is transferred to the pilot trainee via an oxygen mask. At the anode, pure oxygen is formed which is stored in a Douglas bag for subsequent use.

The electrochemical mechanism used to separate oxygen from the air is very accurate and efficient. Therefore, the oxygen concentration may be accurately controlled resulting in simulated altitude from 0 to 30,000 ft. Additionally, the device required no compressed gases, eliminated the logistics chain associated with current devices. The EOS device only required electrical power and a water source to replace water vapor lost to the ambient surroundings.

Figure 1:
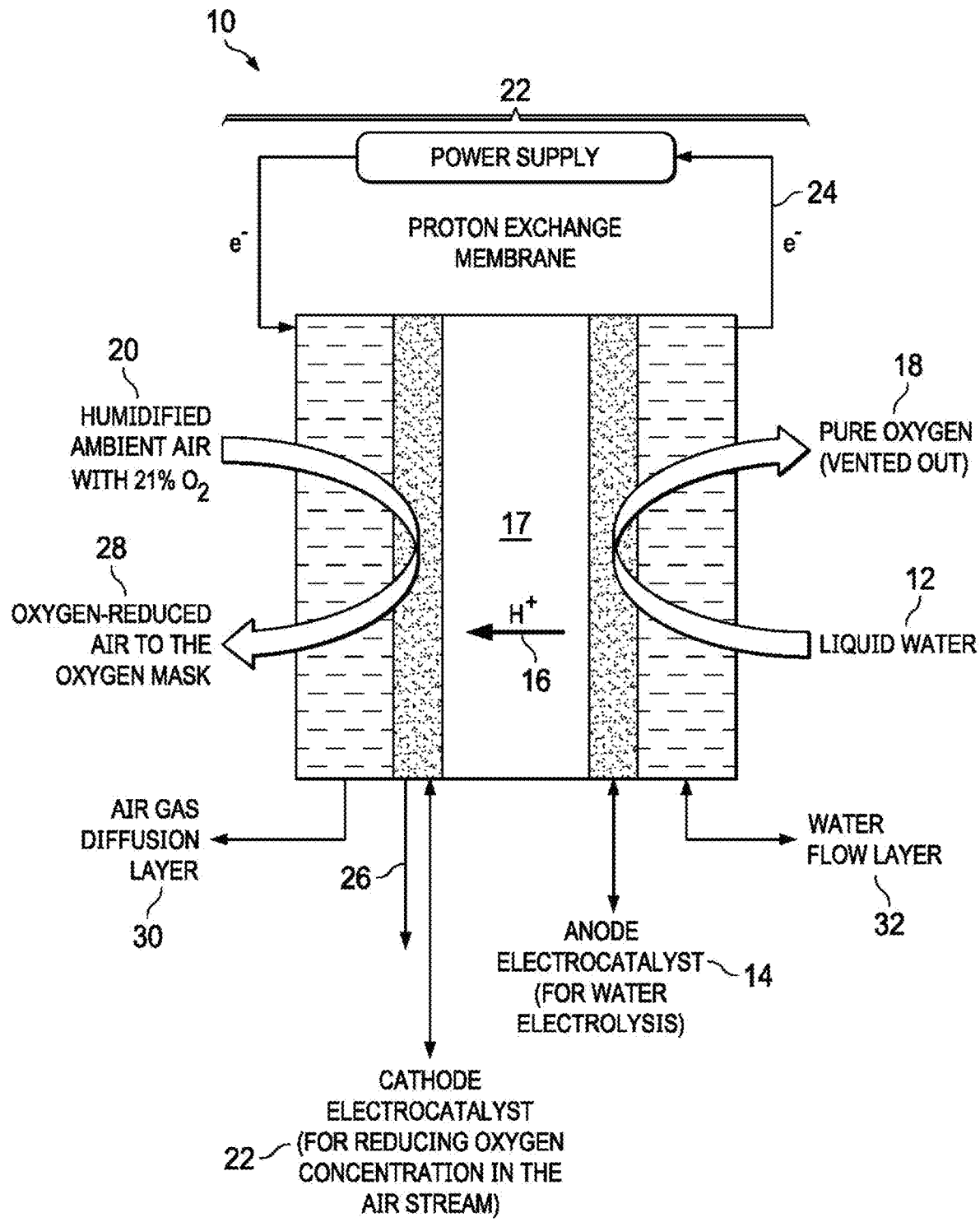
FIG. 1 shows a basic electrochemical operation schematic for the electrochemical oxygen separation of the present invention that generates an oxygen-reduced air for, e.g., hypoxia training for naval pilot trainees.

The basic operation principles of the electrochemical oxygen separator device 10 are shown in FIG. 1 and the corresponding electrochemical reactions are described in Table 1. Liquid water 12 is fed to the anode compartment 14 and water molecules are dissociated into hydrogen protons 16 and oxygen 18 via electrolysis reaction over the anode electrocatalyst (see anode half-cell reaction in Table 1). Atmospheric air 20 is fed into the cathode compartment 22 of the electrochemical cell 22. Protons 16 generated at the anode 14 are transported to the cathode side 22 due to the electrical field gradient 24 across a proton exchange membrane 17 and react with the oxygen in the air 20 to generate both water 26 and reduced-oxygen air 28 (this reaction is also known as electrochemical cathode depolarization). The electrochemical cathode 22 depolarization phenomenon lowers the electrochemical device's electrical potential and hence, reduces its power consumption. The reduced-oxygen air stream 28 at the cathode outlet is then transferred to the pilot trainee via an oxygen mask. The pure oxygen 18 generated at the anode is stored in a storage container (e.g., a Douglas bag) during normal operation. However, the pure oxygen anode stream can be made available for mask delivery in the event of a medical emergency. Also depicted in FIG. 1 are an air gas diffusion layer 30 and a water flow layer 32.

TABLE 1

Electrochemical half-cell reactions for the electrochemical oxygen separator technology.

| | |
|---|---|
| Cathode | $4H^+ + 4e^- +$ Ambient air with 21% $O_2 \rightarrow 2H_2O +$ Reduced-oxygen air stream |
| Anode | $2H_2O \rightarrow$ Pure $O_2 + 4H^+ + 4e^-$ |
| Overall | Reduced-oxygen air stream (cathode outlet to oxygen mask) $\rightarrow$ Pure $O_2$ (anode outlet stored) |

An electrochemical oxygen separator device uses an advanced oxygen evolution reaction (OER) electrocatalyst and feeding the water to the anode side. The efficiency and power consumption of the proposed electrochemical oxygen separator device are mainly governed by the anode electrocatalyst and how the liquid water is fed. The present invention includes the development of an advanced OER electrocatalyst. Since the anode side of the electrochemical oxygen separator uses a water electrolysis reaction, a novel OER electrocatalyst was optimized to provide high efficiencies. The OER electrocatalyst of the present invention demonstrated over 85% efficiency for water electrolysis. In addition, to further improve the efficiency of the electrochemical oxygen separator device, liquid water can be fed directly to the anode side. Flowing the water directly onto the anode electrocatalyst eliminates the reactant mass transfer issues and allows the device to operate at high current densities, which will drastically reduce the mass and volume of the final system.

Figure 2A:
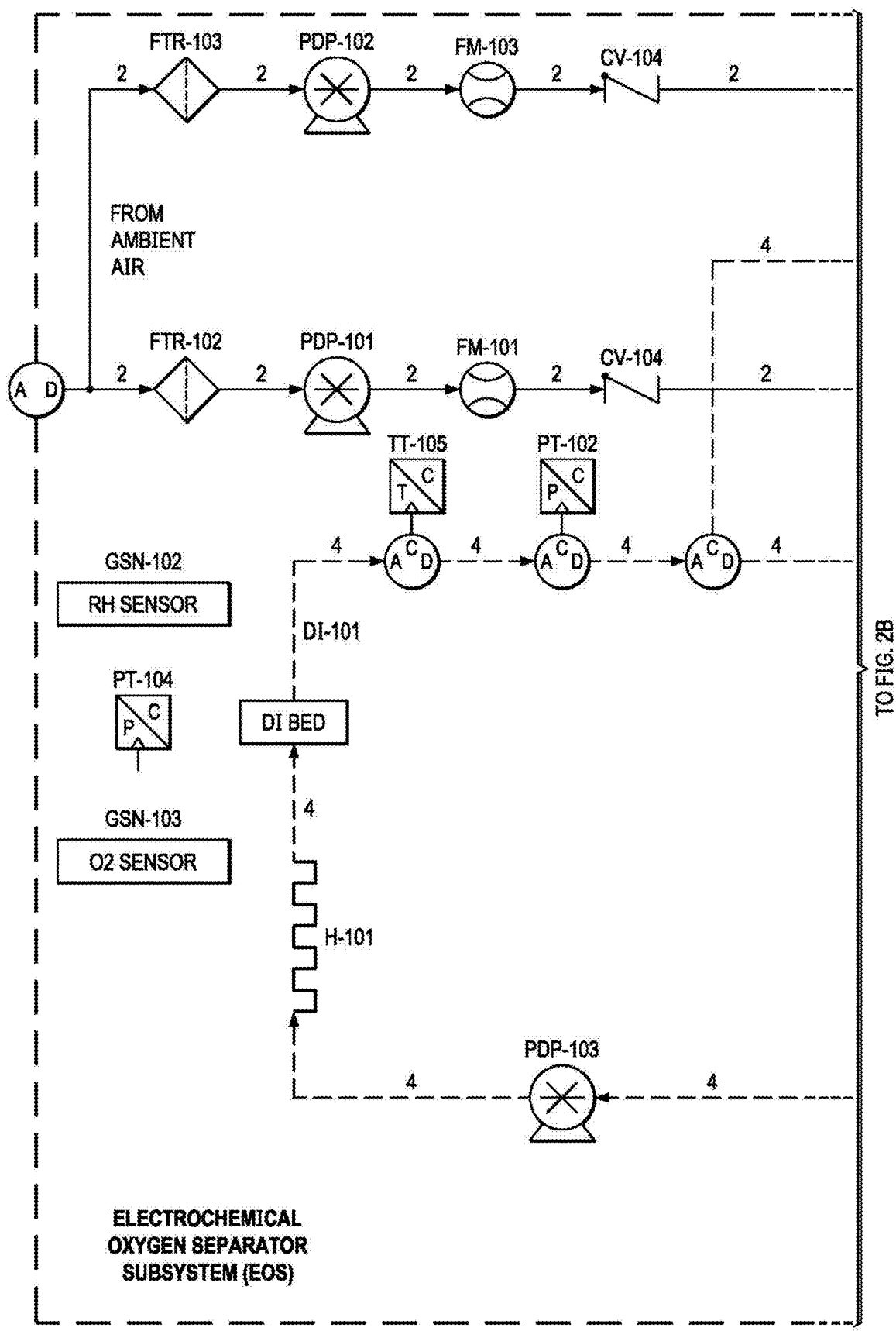
FIGS. 2A to 2E show a basic piping and instrumentation diagram (P&ID) for an electrochemical oxygen separation (EOS) EOS system of the present invention.
Figure 2B:
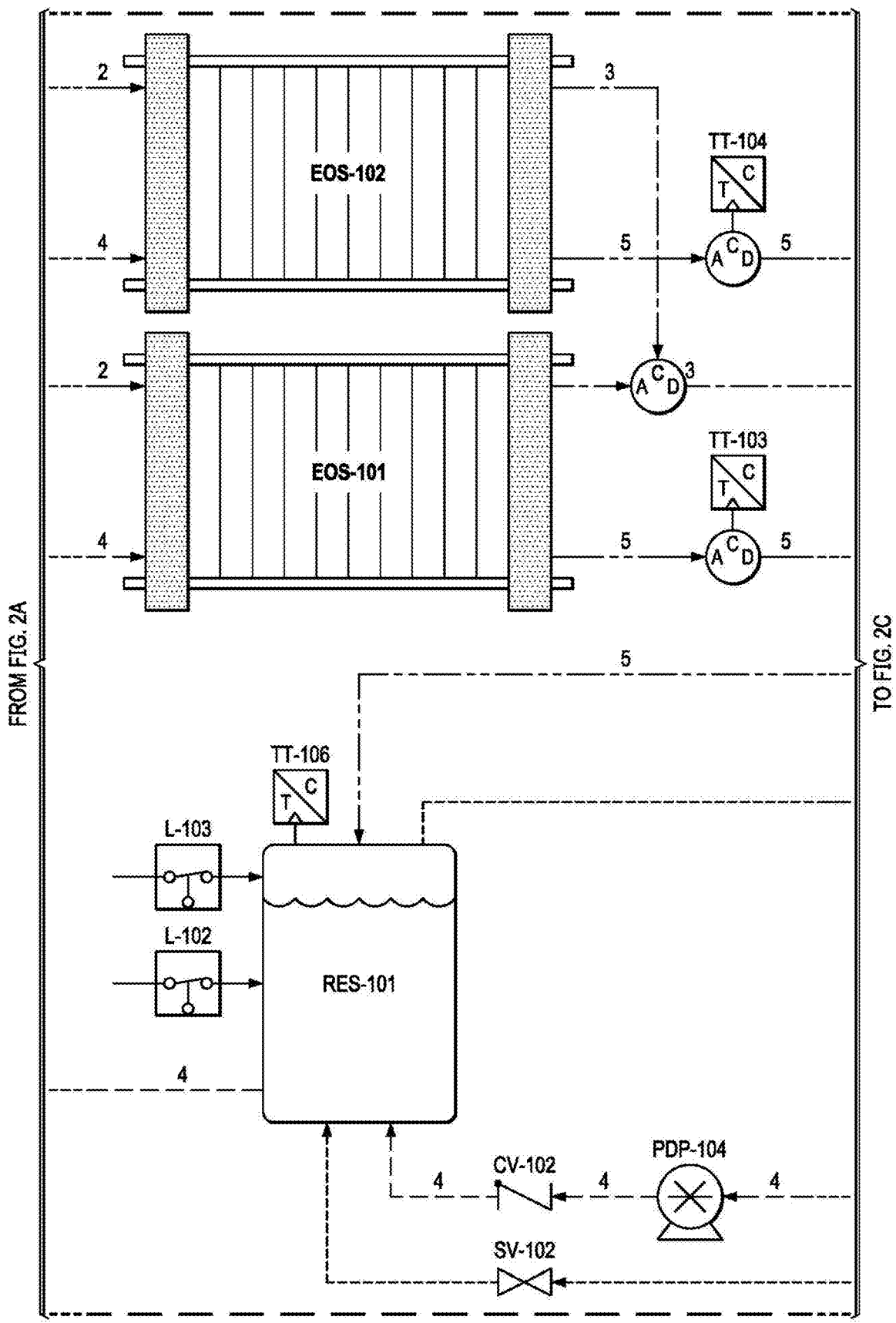

Supporting system for the EOS technology. The electrochemical stack requires supporting Balance of Plant (BOP) components to function. Two basic piping and instrumentation diagrams for use with the present invention are shown in FIGS. 2A to 2E and 3A to 3H. FIGS. 2A to 2E show a basic piping and instrumentation diagram (P&ID) for an electrochemical oxygen separation (EOS) EOS system of the present invention. For remote operations, air pumps may be needed to pressurize and force the air through the system. Generally, the pressure generated by these air pumps (~10-15 psig) also enables the pressure demand operation discussed in a later section. In FIG. 2A, air can be filtered via particulate filters (FTR-102 & 103 (see FIG. 2E)) before entering the system. In FIG. 2B, the flow rate from the air pumps is metered via two flow meters (FM-101 & 103). Measuring the amount of air entering the system is important as it defines the amount of oxygen that will need to be removed by the electrochemical stacks (EOS-101 & 102). As previously discussed, the electrochemical stacks are responsible for separating the oxygen from the cathode to the anode. The molar quantity of oxygen separated is directly proportional to the electrical current applied to the stacks. Therefore, accurate control of the applied current results in an accurate control of the oxygen concentration and thus simulated altitude.

Figure 2C:
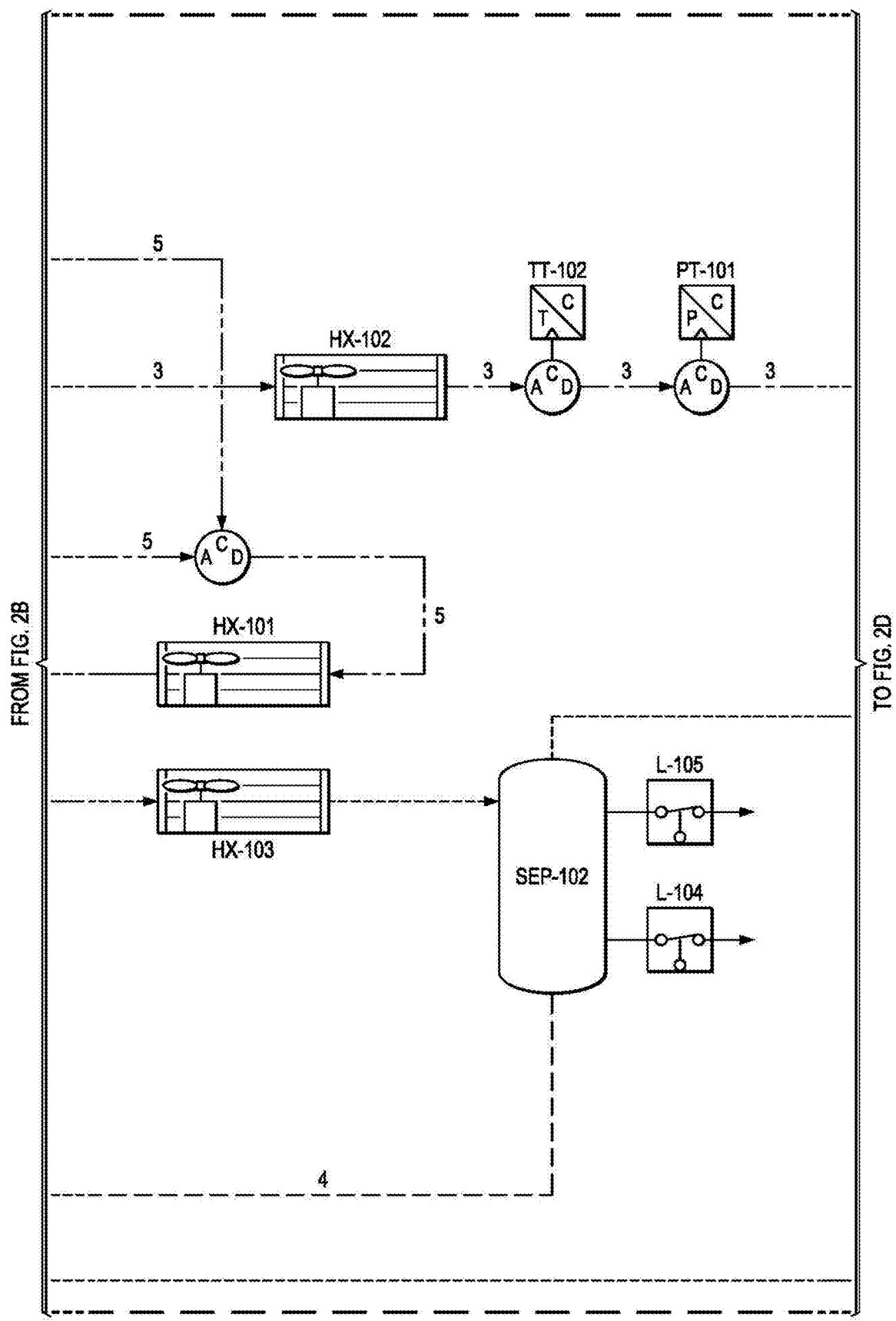
Figure 2D:
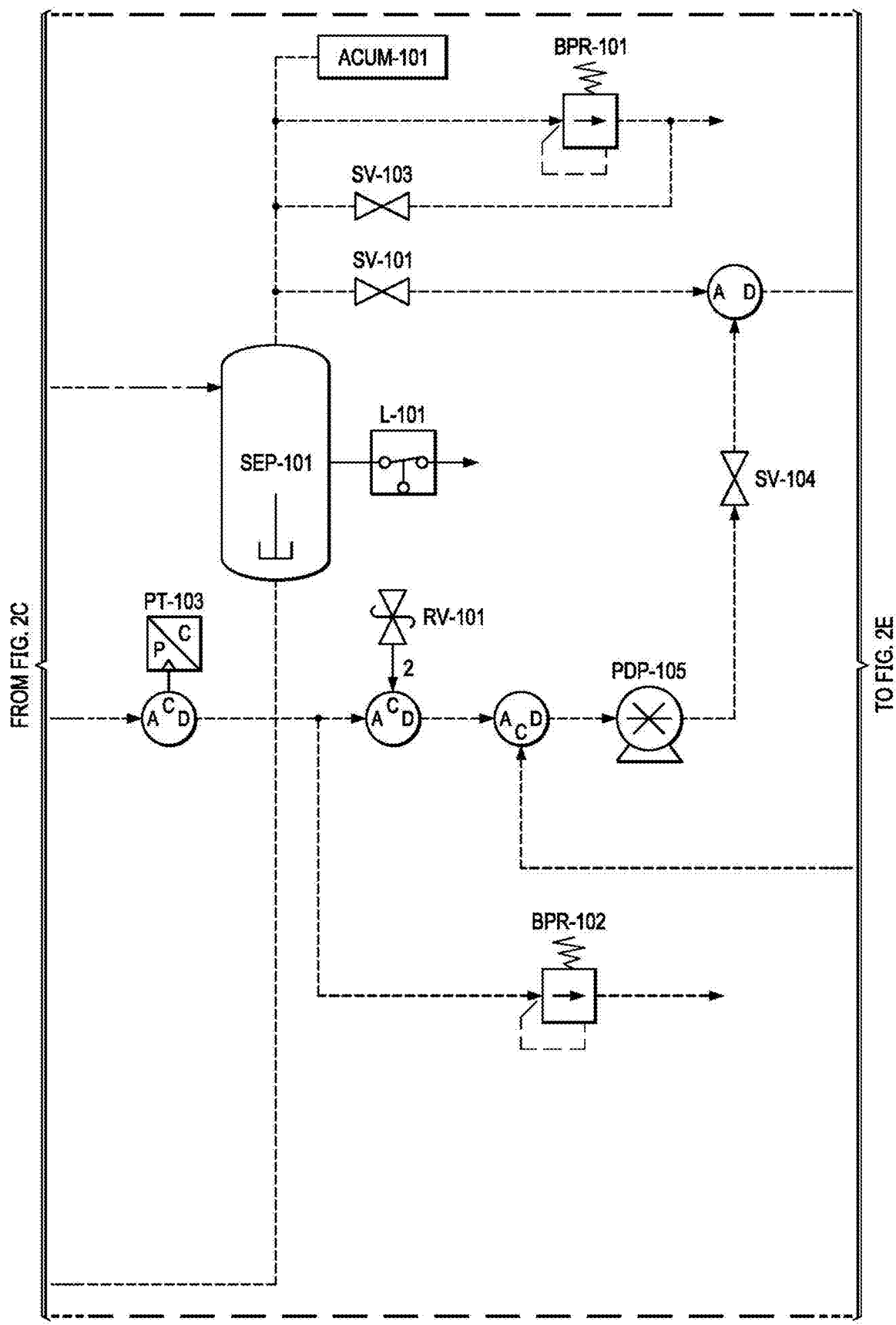

FIGS. 2B and 2C show that, in this version, after the stack, the oxygen depleted cathode stream is cooled back down to room temperature via HX-102 where excess water vapor is condensed. In FIG. 2D, this condensed water is then separated out via SEP-101. The collected liquid water is captured and delivered back to the water reservoir (RES-101) in an effort to conserve water. The resulting oxygen depleted cathode air is then collected in an accumulator (ACUM-101) where it is subsequently vented through a back pressure regulator (excess production) (BPR-101), or delivered to the pilot. System pressure can be monitored by pressure transducers (PT-101, PT-103) operated separately or together mounted between the EOS system and accumulator (ACUM-101).

Figure 2E:
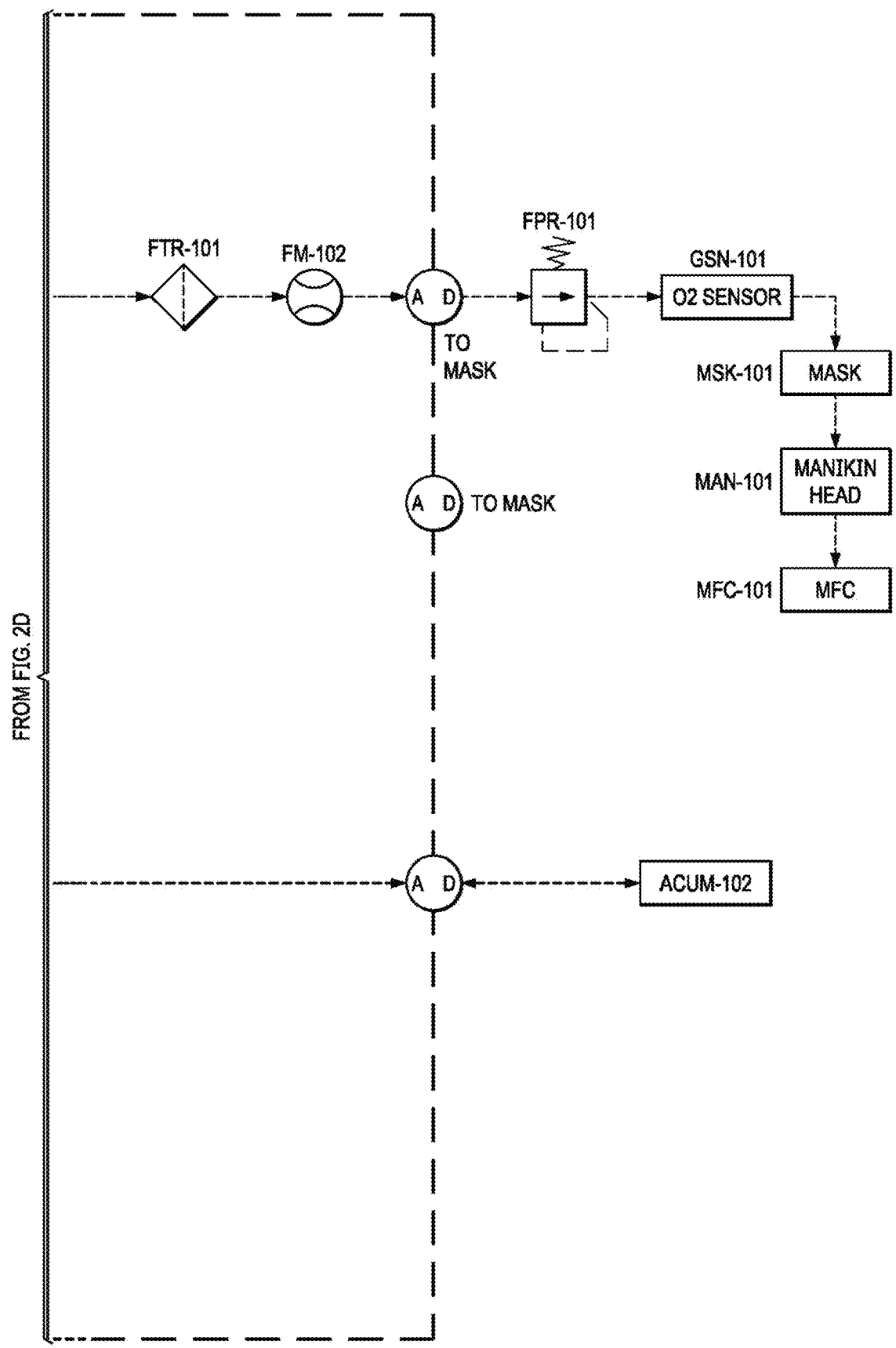

In FIG. 2E, before delivery to the user (e.g., a pilot), the cathode air is first filtered via a particulate filter (FTR-101) and metered with a flow meter (FM-102). The metered flow is used to calculate the pilots breathing rate (slpm), tidal volume and BPM (breaths per minute), which may be data logged for further analysis and/or display. The EOS system of the present invention has the capability to interchange regulators (FPR-101). The regulator is responsible for enabling the mask breathing response. This can be configured for pressure on demand (positive pressure mask which forces air into lungs) or dilution demand (negative pressure mask which required the pilot to pull air into the lungs) functionality.

The electrochemical stack can also incorporate a thermal control. This may be accomplished through a re-circulated liquid coolant loop, which is incorporated into the anode of the stack. A water reservoir (RES-101) is filled with de-ionized water (see FIG. 2B). Water is circulated via PDP-103 (see FIG. 2A) through a water heater (H-101, which heats the coolant during startup) and a de-ionization bed (DI BED) before being delivered to the electrochemical stacks. In addition to a coolant, the water can also humidify the stack, supplying the water needed at the anode for electrolysis. As the electrochemical reactions take place, oxygen is evolved and exits the anode along with the water. The two phase mixture then passed through an air cooled heat exchanger before dumping back in the water reservoir.

The coolant reservoir also acts as a phase separator, which allows the produced oxygen to escape through a vent at the top. This product oxygen stream then pass through an air-cooled condenser (similar to the cathode stream), which condenses any excess water. The product oxygen stream then flows into a secondary phase separator, which recycles the water that is delivered back to the coolant reservoir.

In FIG. 2E, the product oxygen stream then vents into an optional storage container (e.g., a Douglas bag (ACUM-102)) where it is stored at ~10" $H_2O$ for subsequent use. If the storage container is not installed, or if the storage container has filled to capacity, the product oxygen vents through a pressure relief valve. When the pilot becomes hypoxic, an oxygen dump feature may be enabled which will deliver pure oxygen to the pilot (if the Douglas bag is present) or ~50% concentrated oxygen to the pilot (if the storage container is not installed).

When the oxygen dump mode is enabled, the cathode stream is closed (by closing SV-101, FIG. 2D), while the anode stream is opened (by opening SV-104, FIG. 2D). This allows oxygen to be pulled from the anode (or the storage container if installed) and delivered to the pilot via the oxygen delivery pump (PDP-105, FIG. 2D).

Figure 3A:
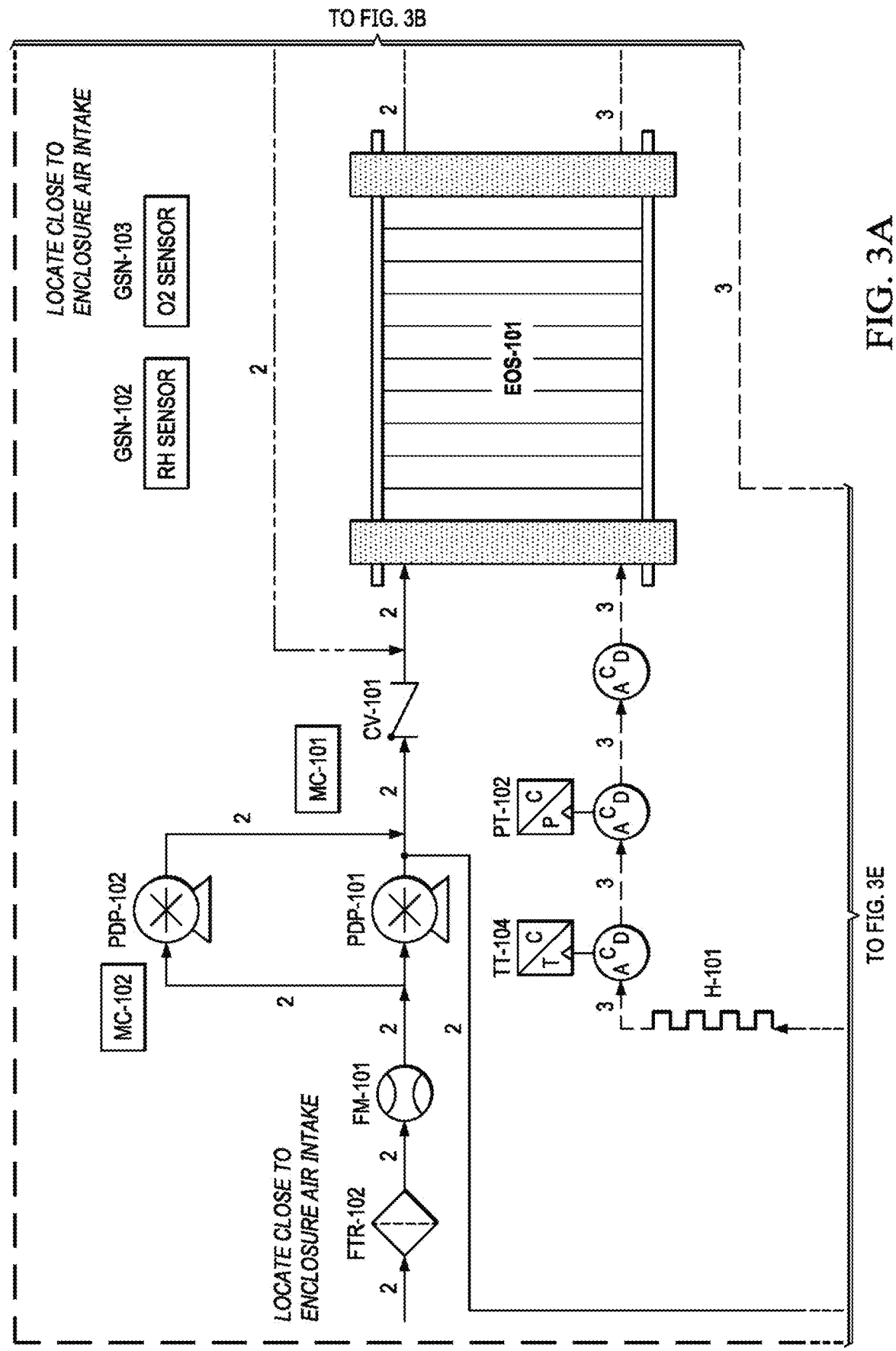
FIGS. 3A to 3H show another basic piping and instrumentation diagram (P&ID) for another EOS system P&ID of EOS system of the present invention.

FIG. 3A to 3H shows another basic piping and instrumentation diagram (P&ID) of EOS system P&ID of EOS system. In FIG. 3A, for remote operations, an air pump may be needed to pressurize and force the air through the system via PDP-101. Generally, the pressure generated by this air pump (~10-15 psig) enables the pressure demand operation discussed in a later section. Pressure in the range ~20-40 psig is also generally used. Piston Air Pumps (such as Thomas by Gardner Denver 22201230INTLSCX pumps) can be used for PDP-101 and PDP-102. Air can be filtered via particulate filters (FTR-102) before entering the system. The flow rate from the air pumps is metered via flow meters (FM-101), e.g., using a MEMS flow sensor FS4000 mass flow sensor. Measuring the amount of air entering the system is important as it defines the amount of oxygen that will need to be removed by the electrochemical stack (EOS-101). A single electrochemical stack is preferred in this embodiment, with the single air pump (PDP-101) forcing air through the system.

As previously discussed, the electrochemical stack is responsible for separating the oxygen from the cathode to the anode. The molar quantity of oxygen separated is directly proportional to the electrical current applied. Therefore, accurate control of the applied current results in an accurate control of the oxygen concentration and thus simulated altitude.

Figure 3B:
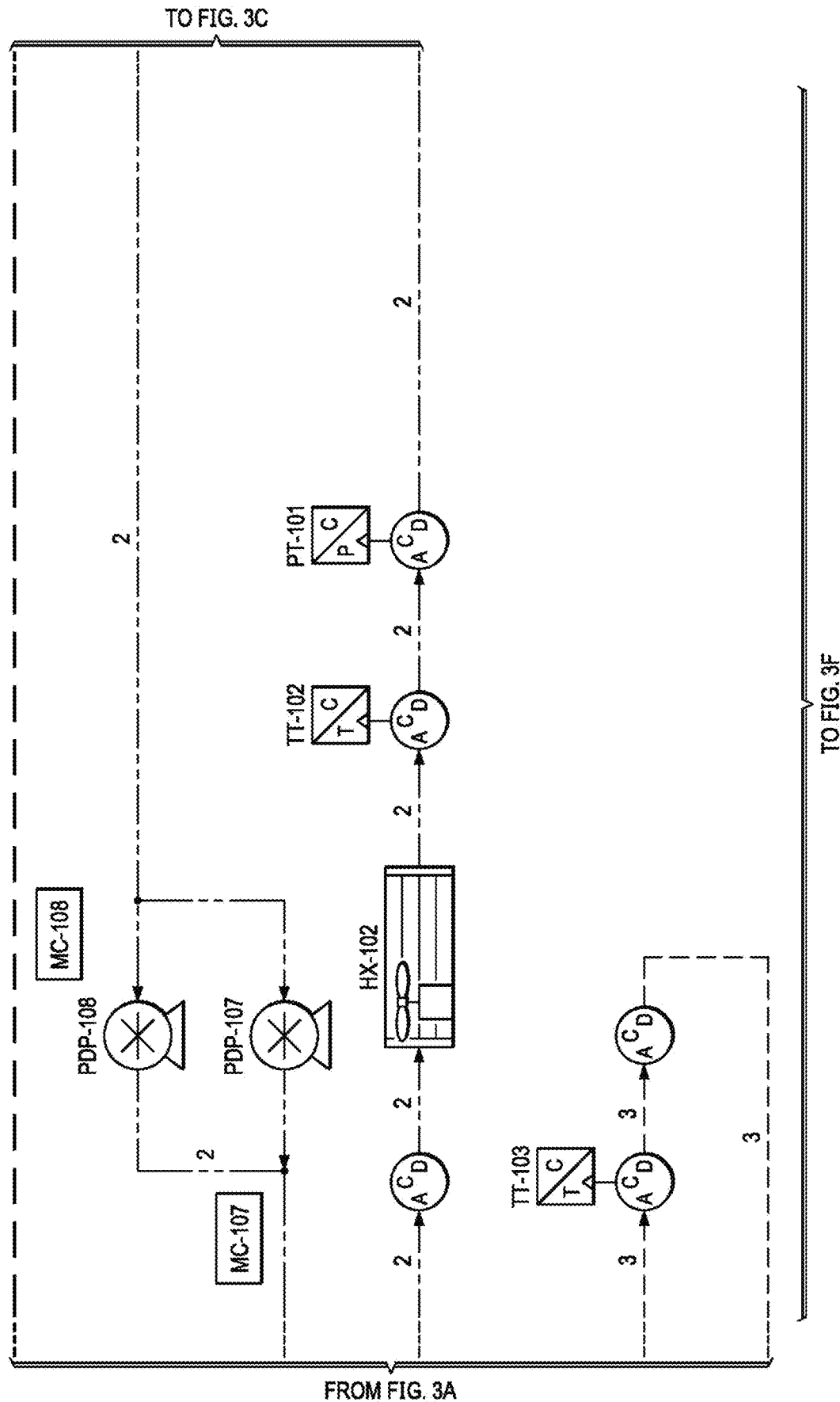

In FIG. 3B, in this version, after the stack, the oxygen depleted cathode stream is cooled via HX-102 where excess water vapor is condensed. This embodiment allows for some of the oxygen-depleted air from electrochemical stack (EOS-101) outlet on the cathode side, to be returned back to the stack's air inlet. Return of oxygen depleted air is via ACUM-101 (FIG. 3C) and pumps PDP-108 and PDP-107. These pumps are under variable control so to allow the amount of gas returning to the inlet to be varied. The pumps may also be operated at a fixed pumping rate. Suitable pumps include Servoflo's D10K micro diaphragm pump, 1420VDP Thomas diaphragm pumps, also Air Squared scroll compressor can be used. The return air loop is implemented for the purposes of reducing water build up in the cathode compartments of the stack. Thereby excess air enters the cathode compartments to remove excess water, controlling "flooding" of the cathode electrode structure. This maintains electrochemical efficiency of the stack and reduces oxygen separation, and hence altitude fluctuations over time.

Figure 3C:
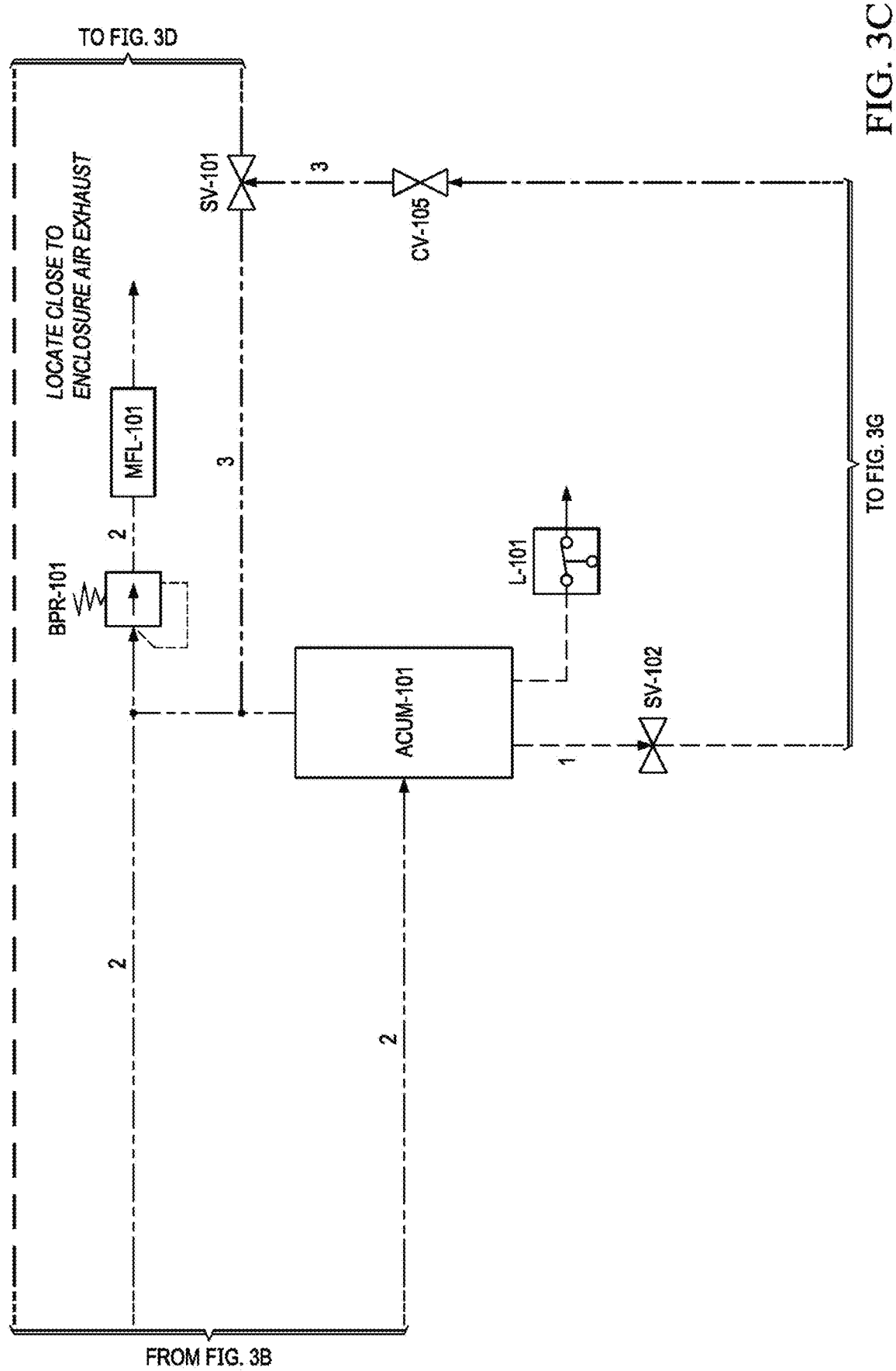
Figure 3D:
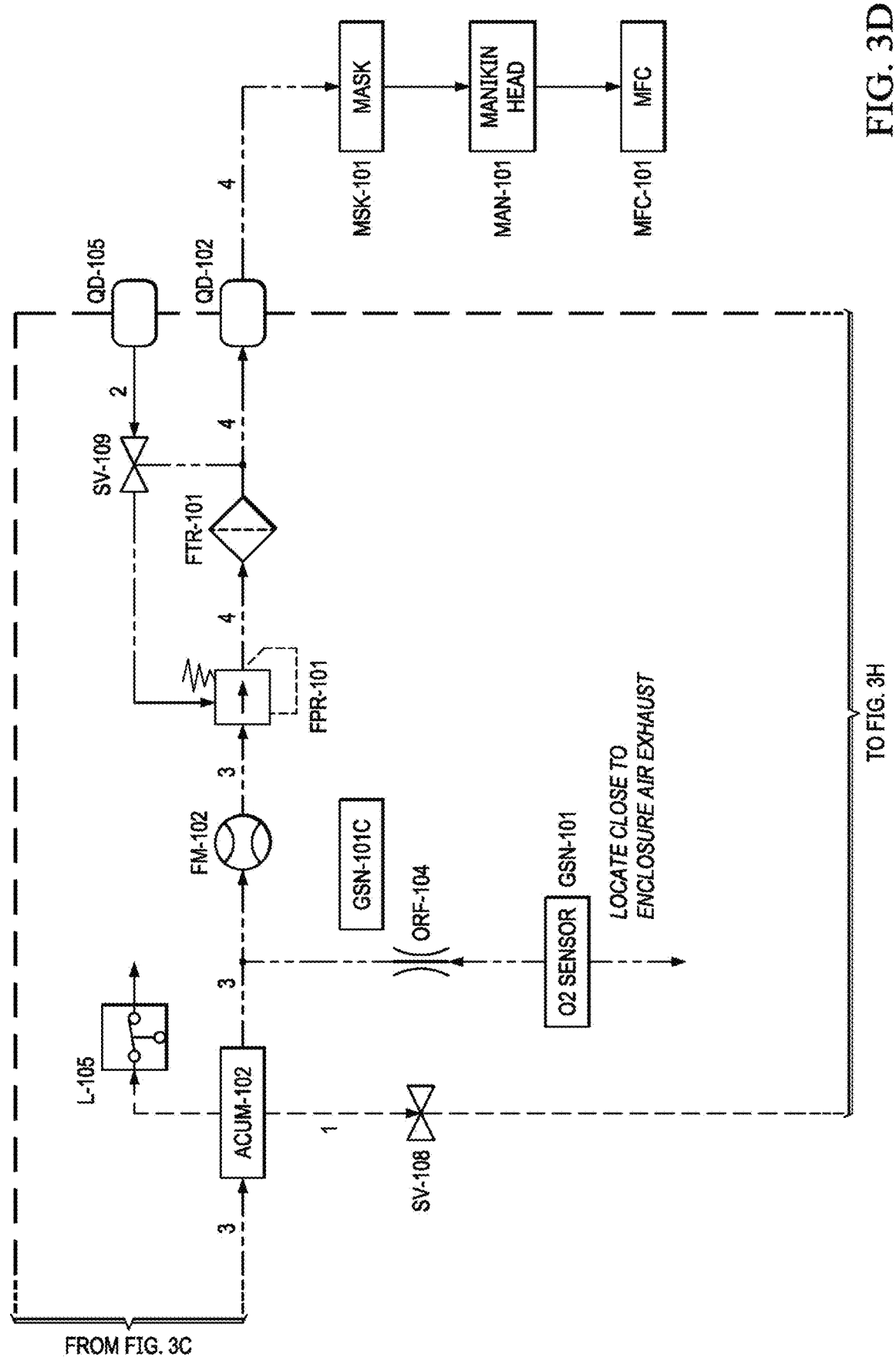
Figure 3E:
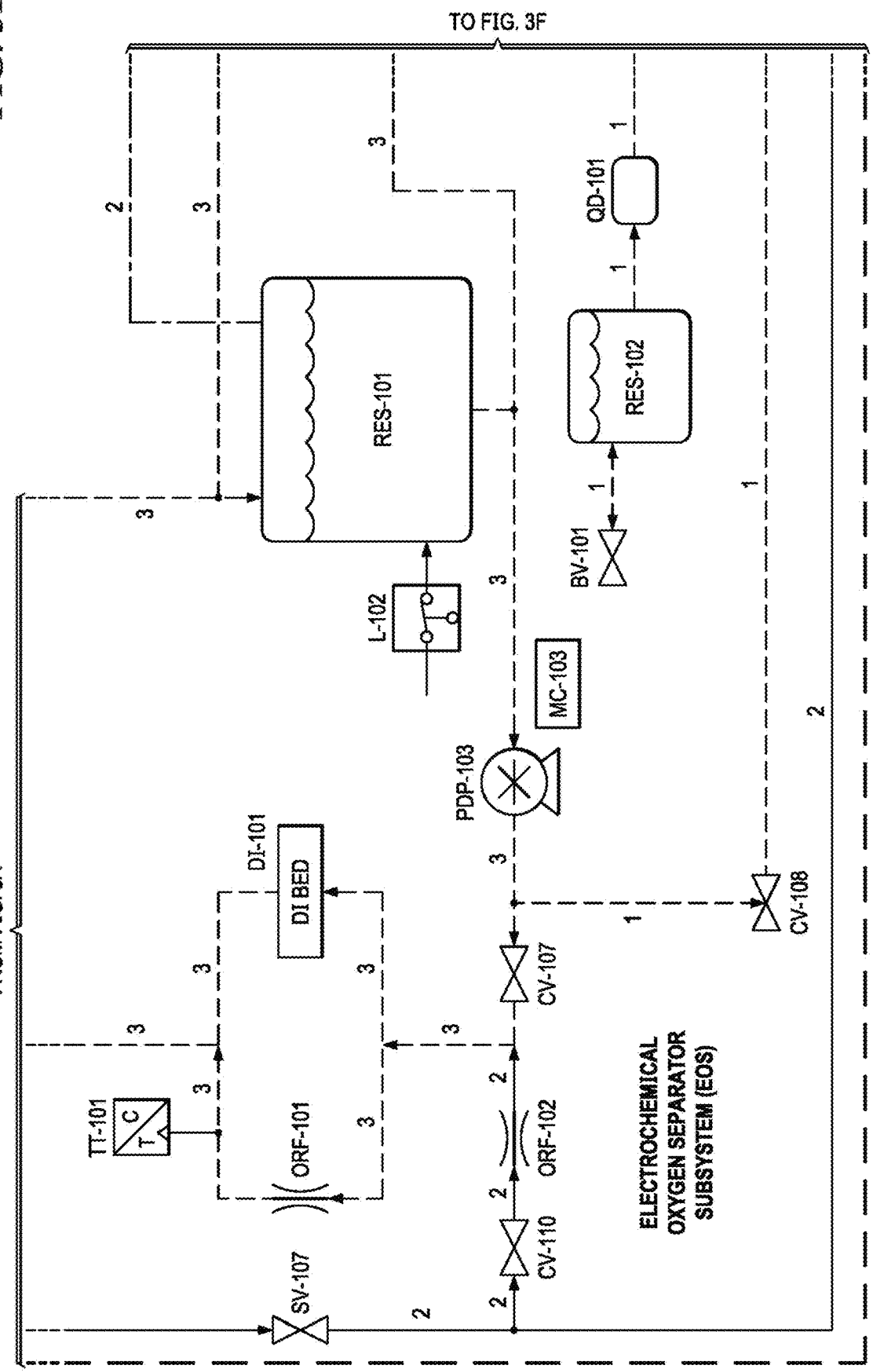

As shown in FIGS. 3C and 3E, this condensed water is then separated out via ACUM-101. The collected liquid water is captured and delivered back to the electrochemical stack via RES-101 in an effort to conserve water. Water is determined via a level sensor (L-101). Water is recovered via PDP-104, then via HX-101 and into container (RES-101). The water is then fed from container RES-101 into the electrochemical stack via PDP-103.

The resulting oxygen depleted cathode air is then collected in an accumulator (ACUM-101) where it is subsequently vented through a back pressure regulator (excess production) (BPR-101), or delivered to the pilot. A suitable back pressure regulator is the Airtrol RV-5300 Miniature Relief Valve. A pressure relief valve or a back pressure regulator could be used for this purpose. System pressure can be monitored by pressure transducer (PT-101) mounted in the conduit between the EOS-101 system and accumulator (ACUM-101).

BPR-101 is used to set the system pressure, or to be more exact it sets the system upper pressure limit. System pressure is here defined as the pressure in the system (conduits and fixtures) that are positioned between and pressure pump (PDP-101) and the pressure regulator (FPR-101). The internal cathode compartments of the stack EOS-101 are included in this zone. The pump PDP-101 pushes against the pressure set by BPR-101.

As shown in FIG. 3D, cathode air is delivered to the pilot via accumulator (ACUM-102). Water in the accumulator is determined by a level sensor (L-105). Water is recovered for conservation purposes via PDP-104, then via HX-101 and into container (RES-101), involving valves. Before delivery to the user (e.g., a pilot), the cathode air is first filtered via a particulate filter (FTR-101) and metered with a flow meter (FM-102). Suitable flow meters include MEMS flow sensor FS1015 CL Mass Flow Sensors. The metered flow is used to calculate the pilots breathing rate (slpm), tidal volume and BPM (breaths per minute), which may be data logged for further analysis and/or display. Prior to being delivered to the pilot, the oxygen content of the oxygen is measured using an oxygen sensor (GSN-101).

In FIG. 3D, the EOS system of the present invention has the capability to interchange regulators (FPR-101). The forward pressure regulator (FPR-101) is responsible for enabling the delivery of oxygen-depleted air according to the user's breathing actions. This can be configured for pressure on demand (positive pressure mask which forces air into lungs) or dilution demand (negative pressure mask which required the pilot to pull air into the lungs) functionality. FPR-101 responds to changes in pressure in the conduit between ACUM-102 and the pilot mask, in response to the users breathing activity.

As shown in FIG. 3E, the electrochemical stack can also incorporate a thermal control. This may be accomplished through a re-circulated liquid coolant loop, which is incorporated into the anode of the stack. A water reservoir (RES-101) is filled with de-ionized water. Water is circulated via PDP-103 through a water heater (which heats the coolant during startup) and a de-ionization bed before being delivered to the electrochemical stacks. In addition to a coolant, the water can also humidify the stack, supplying the water needed at the anode for electrolysis. As the electrochemical reactions take place, oxygen is evolved and exits the anode along with the water. The two phase mixture then passed through an air cooled heat exchanger before dumping back in the water reservoir (RES-101).

Figure 3F:
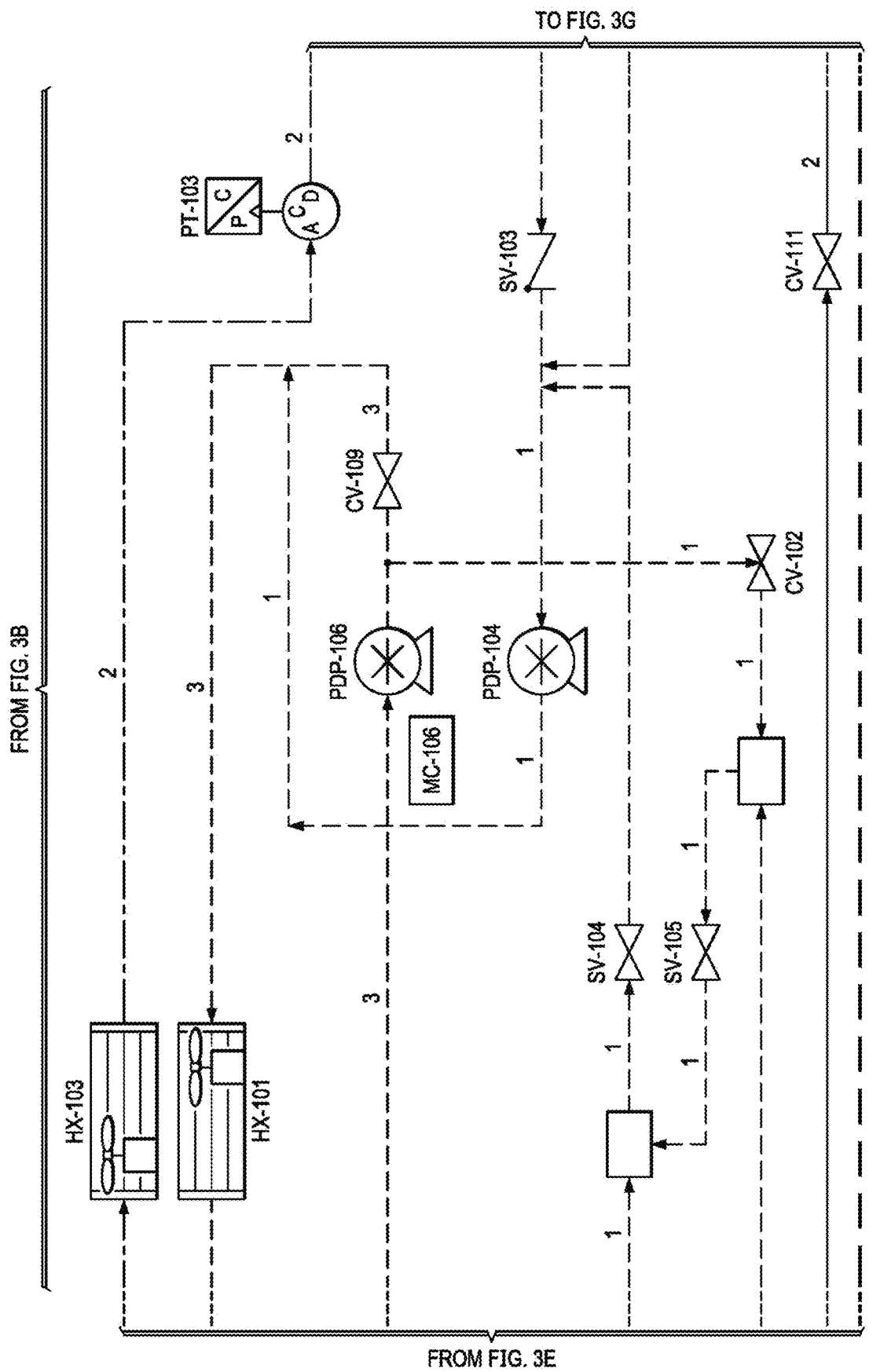
Figure 3G:
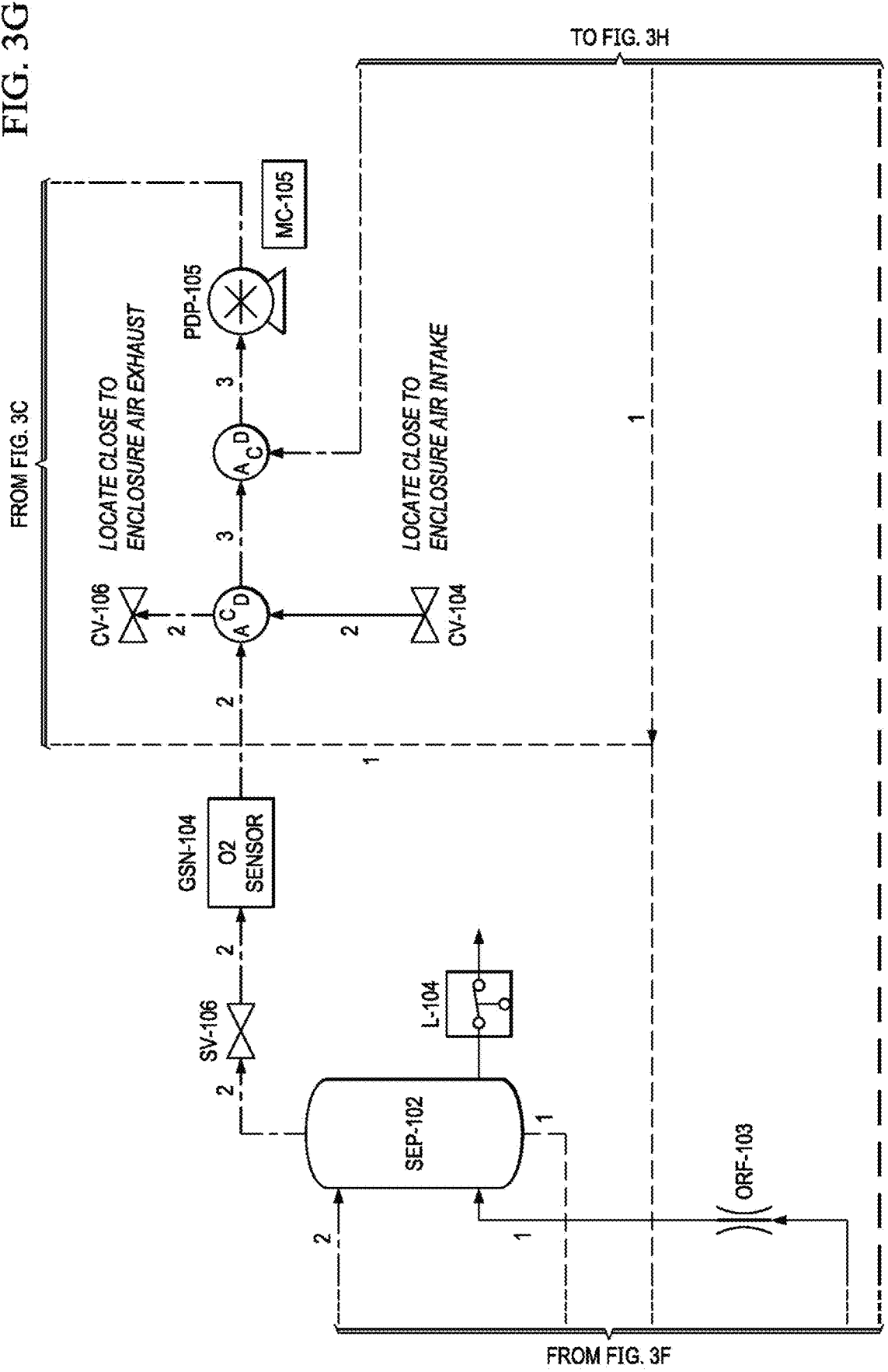

As shown in FIGS. 3F and 3G, the coolant reservoir also acts as a phase separator, which allows the produced oxygen to escape through a vent at the top. This product oxygen stream then pass through an air-cooled condenser (similar to the cathode stream), which condenses any excess water (HX-103). The product oxygen stream then flows into a secondary phase separator, which recycles the water (SEP-102), which is delivered back to the coolant reservoir.

Figure 3H:
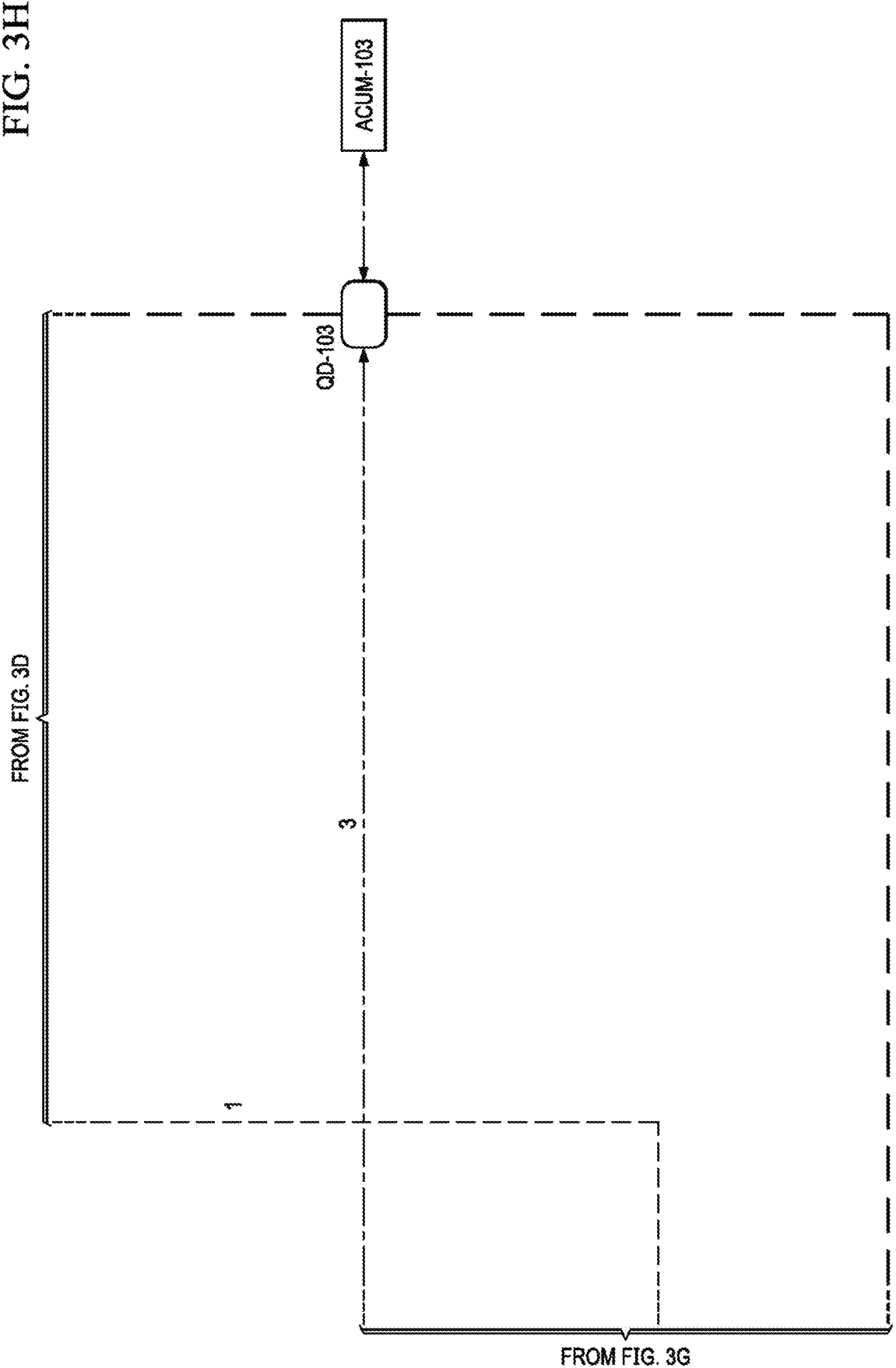

As shown in FIG. 3H, the product oxygen stream then vents into an optional storage container (e.g., a Douglas bag (ACUM-103)) where it is stored at ~10" $H_2O$ for subsequent use. If the storage container is not installed, or if the storage container has filled to capacity, the product oxygen vents through a pressure relief valve. When the pilot becomes hypoxic, an oxygen dump feature may be enabled which will deliver pure oxygen to the pilot (if the Douglas bag is present) or ~50% concentrated oxygen to the pilot (if the storage container is not installed).

When the oxygen dump mode is enabled, the cathode stream is closed (by closing SV-101, FIG. 3C), while the anode stream is opened (by opening SV-104, FIG. 3F). This allows oxygen to be pulled from the anode (or the storage container if installed) and delivered to the pilot via the oxygen delivery pump (PDP-105, FIG. 3F).

Figure 4:
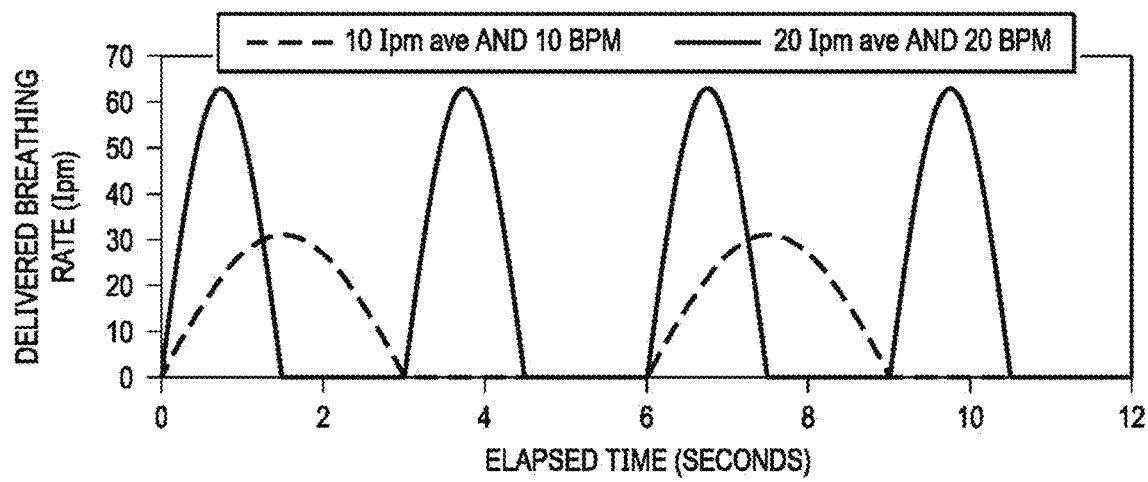
FIG. 4 shows an example of approximated clipped sine wave breathing profiles as delivered to the pilot. For an average flow rate of 10 and 20 liters per minute (lpm), the peak instantaneous flow rate is 31.4 and 62.8 lpm respectively (Average flow rate times Pi).

Using an electrochemical separation approach to produce reduced oxygen air for hypoxia training. Pressure on demand generation feature within the hypoxia device. Human breathing can be approximated by a sine wave at a frequency of 10 to 20 BPM (Breaths per Minute) and an average flow rate of ~10-20 lpm. For example, the aviation masks currently used by the military have exhaust valves resulting in a unidirectional flow of gas going to the pilot. This results in an apparent clipped sine wave being delivered to the pilot with peak instantaneous flow rates up to 62.8 lpm (FIG. 4). Additionally, it is not uncommon for larger individuals to breathe significantly more than this.

However, the EOS stacks of the present invention perform better while producing a constant flow rate of simulated altitude breathing gas. In order to avoid grossly over sizing the system for maximum instantaneous flow rates, the EOS system can be designed with a pressurized accumulator sized to dampen the breathing waveform.

Figure 5:
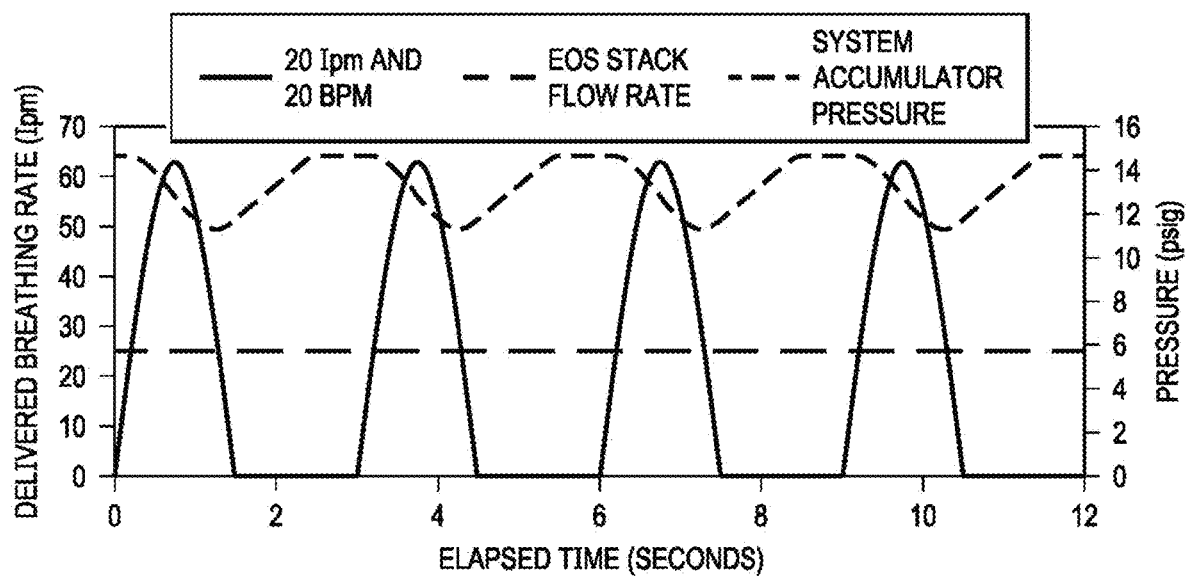
FIG. 5 shows a simulated breathing waveform of 20 lpm & 20 breaths per minute (BPM) delivered by the EOS system of the present invention. Based on an accumulator size of 2 Liters and a constant gas production rate of 25 lpm, the system accumulated pressure oscillated by only 4 psid while maintaining a minimum system pressure of 10 psig at all times.

FIG. 5 demonstrates the performance of EOS system of the present invention while operating at a maximum system pressure of 15 psig and accumulator volume of 2 Liters. An average breathing rate of 20 liters per minute (lpm) with peak instantaneous rate of over 60 lpm are delivered to the pilot with a constant production rate of 25 lpm from the EOS stacks. System accumulator pressure is maintained within 4 psid and never falls below a threshold of 10 psig, insuring that air starvation will not be an issue.

The electrical power consumed by the EOS system of the present invention is primarily related to the air production rate. Therefore, at average flow rates of 30,000 ft simulated air the device power can exceed what a typical 120 vac/15 amp receptacle can provide. Since breathing rates vary from pilot to pilot, a pressure demand based production algorithm was developed that enables the EOS system of the present invention to only produce the flow rate required based on the demand of the pilot.

The flow rate required based on the demand of the pilot is enabled by the use of intelligent pressure and flow rate feed back to the EOS stack and air pumps. Average accumulator pressure and delivered flow rates are monitored to detect increases in pilot demand. The two air pumps are then ramped up in proportion to meet this demand (maintaining flow rate and accumulated pressure). As the air pumps ramp up, additional flow is detected by the inlet flow meters, which trigger a rise in the electrochemical stack current. These relations effectively ramp the production up or down to meet the demand of the pilot while maintain accurate simulated altitude control and preventing air starvation.

Advanced OER (Oxygen Evolution Reaction) electrocatalyst. The Need for Advanced Anode Electrocatalyst for Electrochemical Hypoxia Device.

Table 1 (above) describes the anode and cathode electrochemical reactions occurring in the electrochemical hypoxia device. While from a thermodynamic perspective, electrolysis of water at anode and reduction of oxygen at cathode side of EOS should be occurring at the same electrical voltage, but due to use of two completely different medium (liquid medium at anode and gaseous medium at cathode), different surface reactions generate different polarizations (change in the equilibrium potential of an electrochemical reaction) and hence observation of different polarization overpotentials. In the electrochemical hypoxia device, oxygen evolution reaction is more sluggish compared to oxygen reduction reaction due to its higher activation overpotential values. Higher overpotential values mean that system is experiencing inefficiencies. The most promising route to reduce the inefficiencies is to lower the activation overpotentials and electrocatalyst component plays the most critical part in achieving lower overpotentials.

Microstructure and chemical composition of the electrocatalyst usually govern the experimentally observed overpotential values (i.e., inefficiencies). How strongly the reaction intermediates bound to the electrocatalyst's surface and how fast the reaction kinetics would be usually governed by the microstructure and chemical composition of the electrocatalyst. The present invention includes a nanoparticle surface modification process for anode electrocatalyst that reduced the binding energies of reaction intermediates to the anode electrocatalyst surface and hence increased reaction kinetics. Enhancing how fast the reactions occurring at the anode significantly improved the electrical efficiencies.

Mechanistic Investigation of OER and Potential Electrocatalysts. OER in aqueous solutions in the water electrolysis reaction, represented by anode reaction of hypoxia device, proceeds always at metal oxide MexO, covered metal electrodes, the anodic overpotential usually exceeding 0.2 V. The OER is supposed to proceed according to the so-called Krasilch'shikov mechanism, in which unstable, overoxidized metal oxide sites are self-stabilizing by mutual redox or disproportionation reactions by release of molecular oxygen (schematically described by Equation 1 thru 3) with regeneration of the lower valent metal oxide:

$$Me_xO_y + H_2O \rightarrow Me_xO_yOH + H^+ + e^- \quad (1)$$

$$Me_xO_yOH \rightarrow Me_xO_{y+1} + H^+ + e^- \quad (2)$$

$$2\,Me_xO_{y+1} \rightarrow 2Me_xO_y + O_2 \quad (3)$$

This mechanistic interpretation is based on the observation, that searching for a volcano-like correlation for activities of OER catalysts, the activity for OER is simply based on the free enthalpy of formation of the overoxidized metal oxide catalyst sites-namely the free enthalpy of formation of the higher oxide from the stable metal oxide. The maximum activity, the tip of the volcano, is observed, where the equilibrium potential for the lower valent and higher valent metal oxides (which can be calculated from the Gibbs-enthalpy of the oxidation reaction of the metal oxide) matches that of the equilibrium potential of the oxygen electrode (+1.23 V vs. RHE). On this basis, $IrO_2$ and $RuO_2$ electrocatalysts were found to be the best metal oxides for OER, sitting at the top of the volcano plot (overpotential vs. enthalpy of oxidation), while PtO exhibits slightly higher overpotentials. Literature supports high catalytic activity of $IrO_2$ for OER, while there have been number of studies based on physically mixed $IrO_2$ and $RuO_2$ as OER catalysts. Surface decoration of nanoparticles is a well-known process in the industry, but most of the time application of the wrong materials does not provide the expected results. It is important that optimal decoration materials are identified and loaded on the base material with the appropriate composition in order to observe the synergetic effects between different elements. In order to demonstrate the efficiencies that can be gained with hypoxia device, the present inventors investigated a series of materials in a very systematic approach and identified the right microstructure with the optimal chemical composition that was needed for anode electrocatalyst. Details of these electrocatalysts and their electrochemical performance in the hypoxia device are provided in the following sections.

Advanced OER Catalyst Manufacturing and Characterization Protocols. A high temperature (450° C.) method was used to prepare these mixed Ir-Ru oxides (Adams 1923). The method is based on oxidation of metal oxide precursors (generally metal halides) in a molten salt (sodium nitrate) environment. The weight ratio of molten salt component to mixed oxide precursor in the method was set to 20 (i.e., X20 protocol). When the weight ratio of molten salt to oxide precursors was 40, it was named as X40 protocol and if the ratio was 10, then it was called X10 protocol. To optimize the Ir and Ru molar ratio, following compositions were prepared:

TABLE 2

Ir to Ru Molar Ratios that were Investigated in Phase I.

| Catalyst ID | Iridium mole fraction | Ruthenium mole fraction |
|---|---|---|
| $IrO_x$ | 100% | 0% |
| $Ir_3RuO_x$ | 75% | 25% |
| $IrRuO_x$ | 50% | 50% |
| $IrRu_3O_x$ | 25% | 75% |
| $Ir_{15}Ru_{85}O_x$ | 15% | 85% |
| $Ir_{10}Ru_{90}O_x$ | 10% | 90% |
| $Ir_5Ru_{95}O_x$ | 5% | 95% |
| $RuO_x$ | 0% | 100% |

Electrochemical characterization of the electrocatalyst samples included collecting OER potentiodynamic curves and EIS spectra in 0.5 M $H_2SO_4$ electrolyte with a VMC VersaStat potentiostat from PAR. Synthesized catalysts were also evaluated for the anodic oxygen evolution reaction in a single cell anode liquid water fed electrolyzer having a 25 $cm^2$ active area using a Fideris Hydrogen Test Station modified for electrolyzer use. The electrolyzer membrane electrode assembly (MEA) had 4 $mg/cm^2$ Pt black as cathode catalyst and 4 $mg/cm^2$ of the corresponding mixed Ir-Ru oxide as the anode catalyst. Nafion ionomer was used on both the anode (45 vol % loading) and cathode (70 vol % loading). Performance of the single cell was tested at 75° C. with no backpressure. Electrolyzer i-V curves were taken for each catalyst and the performances was compared to determine optimum Ir to Ru molar ratio.

After optimizing the chemical composition of Ir-Ru mixed oxide, the effects of synthesis temperature and synthesis protocol parameters were investigated. Some of the mixed Ir-Ru oxides with different molar ratios from Table 2 were synthesized at 550 and 450° C. In addition, the effect of chemical components' weight ratio in the Adam's synthesis protocol was explored. Currently, the weight ratio of molten salt to Ir-Ru oxide precursors was set to 20. Molten salt to Ir-Ru precursors' weight ratios of 40 and 10 were investigated.

Next, an Ir-Ru oxide catalyst was selected for Pt and Au loading optimization. Au loadings of 1, 5, 10, 20, 30, and 40 wt % were investigated. Pt loadings of 1, 5, 10, and 20 wt % were investigated. Initially, optimal loadings of Au and Pt were determined individually. After identification of the optimal loading for each surface modifier, combined Pt-Au binary surface modification was examined. For the binary nanoparticles, the following synthesis route was explored: the gold was reduced on the mixed oxide first, then, platinum a reduction was conducted. Then, the effect of Nafion loading in the anode catalyst layer on the electrolyzer performance was studied with the optimized catalyst. Currently, 45 vol % Nafion ionomer is used for the anode catalyst layer. Loadings of 33, 40, 47, and 61 vol % Nafion ionomer were investigated to optimize the anode ionic conductivity without increasing overall electrical resistance.

Figure 6:
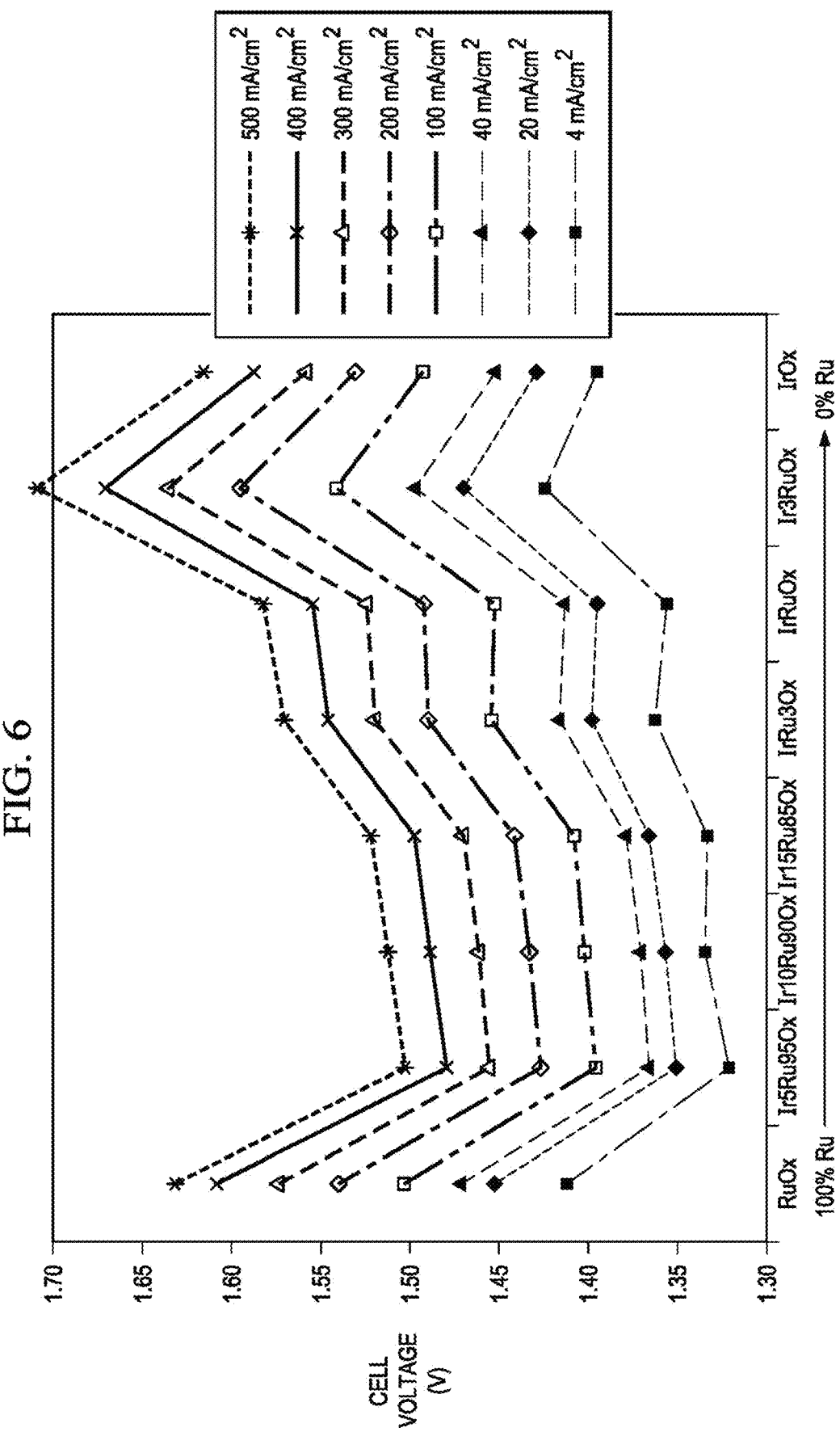
FIG. 6 shows the cell potential as a function of the chemical composition at specific current densities for catalysts synthesized at 550° C., X20 protocol (for Ir to Ru molar ratio optimization). $Ir_5Ru_{95}O_x$ (5 to 95 mol % of Ir to Ru ratio) catalyst demonstrated the best performance. $Ir_5Ru_{95}O_x$ catalyst provided a cell voltage of 1.428 V at 200 mA/cm² was obtained with five-mil thick Nafion membrane (86.13% efficiency) at a 75° C. cell temperature in the anode-fed mode. No backpressure.
Figure 7:
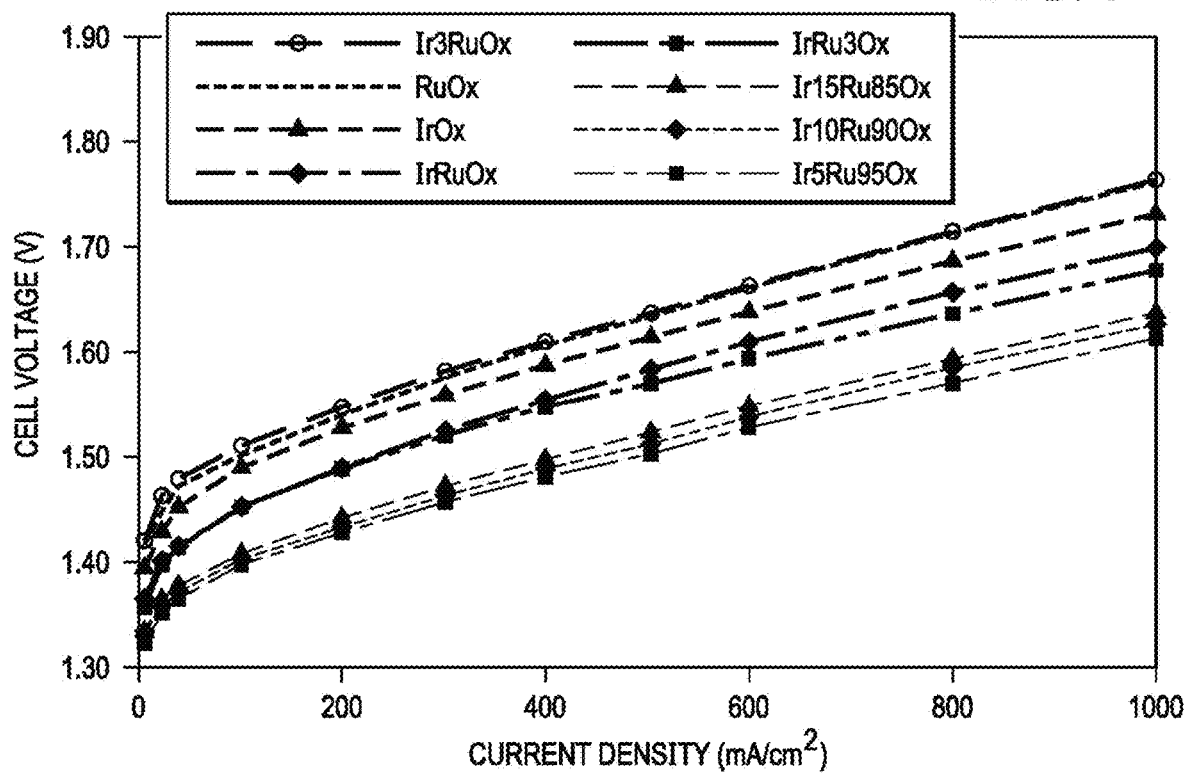
FIG. 7 shows results from a single cell for catalysts synthesized at 550° C., X20 protocol (for Ir to Ru molar ratio optimization). $Ir_5Ru_{95}O_x$ (5 to 95 mol % of Ir to Ru ratio) catalyst demonstrated the best performance; a cell voltage of 1.398 V at 200 mA/cm² was obtained with five-mil thick Nafion membrane at a 75° C. cell temperature in the anode-fed mode. No backpressure.

Optimization of the iridium to ruthenium molar ratio. To identify the optimal Ir to Ru molar ratio for the mixed oxide, catalyst samples listed in Table 2 were synthesized at 550° C. using the X20 protocol. Synthesized catalysts were electrochemically characterized in a single cell with five-mil thick Nafion membrane (from DuPont) at 75° C. and zero backpressure. The single cell results are given in FIGS. 6 and 7. $Ir_5Ru_{95}O_x$ (5:95 mol % of Ir to Ru ratio) catalyst demonstrated the best electrolysis performance. $Ir_5Ru_{95}O_x$ catalyst provided a cell voltage of 1.428 V at 200 $mA/cm^2$, which corresponds to an efficiency of 86.13%.

While there are several electrocatalysts that can be used for anode side of hypoxia device, the most efficient ones would be based on the mixtures of $IrO_2$ and $RuO_2$ materials. While $IrO_2$ has excellent corrosion resilience for hypoxia device, it has higher overpotential compared to $RuO_2$. On the other hand, $RuO_2$ is highly active as a electrocatalyst, it does not possess the electrochemical stability for hypoxia device. While this patent is not limited to the following compositions, but it is preferred to have 0 to 95 mol % of $RuO_2$ (with the balance being $IrO_2$) in order to have both excellent electrocatalytic activity and good electrochemical stability in an electrochemical hypoxia device. More preferably, 50 to 95 mol % of $RuO_2$ (with the balance being $IrO_2$) in order to further improve the electrochemical stability and good catalytic activity, even more preferably, 75 to 95% mol % of $RuO_2$ (with the balance being $IrO_2$) for the best electrochemical activity and satisfactory corrosion resistance.

Figure 8:
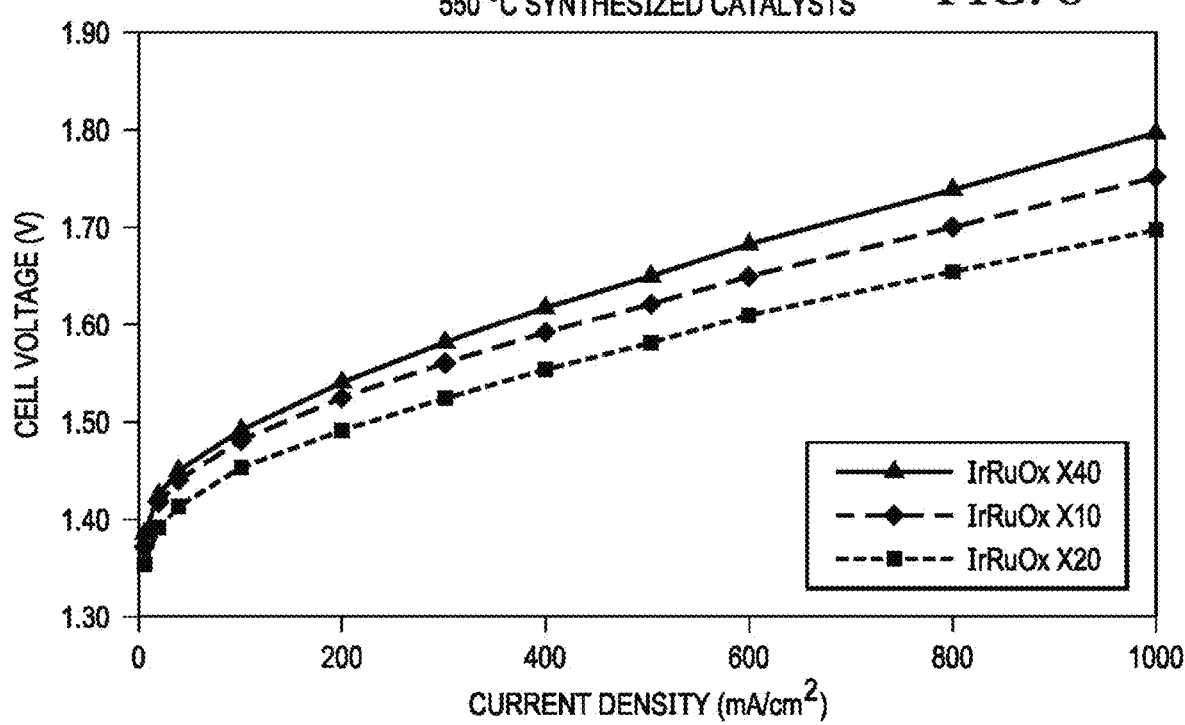
FIG. 8 shows results from a single cell for IrRuOx catalysts synthesized at 550° C. with X10, X20, and X40 protocols (synthesis protocol optimization). IrRuOx catalyst that was synthesized with X20 protocol demonstrated the best performance with five-mil thick Nafion membrane at a 75° C. cell temperature in the anode-fed mode. No backpressure.

Effect of synthesis protocol and synthesis temperature and optimization of these parameters. The synthesis protocol effect was investigated with IrRuOx catalyst (1:1 molar ratio of Ir to Ru) as a baseline. IrRuOx catalysts were synthesized at 550° C. with three different synthesis protocols, namely X10, X20, and X40 protocols. Single cell results are given in FIG. 8. The catalyst sample that was synthesized with X20 protocol demonstrated the best performance.

While this patent is not limited to the following weight ratio of oxidizer salt to metal oxides for the synthesis, in certain embodiments it may be preferred to have 5 to 40 fold in excess of oxidizer salt (compared to the weight of the metal oxide), in other embodiments 10 to 35 fold in excess of oxidizer salt (compared to the weight of the metal oxide), and in other embodiments a 20 to 30 fold in excess of oxidizer salt (compared to the weight of the metal oxide).

Figure 9:
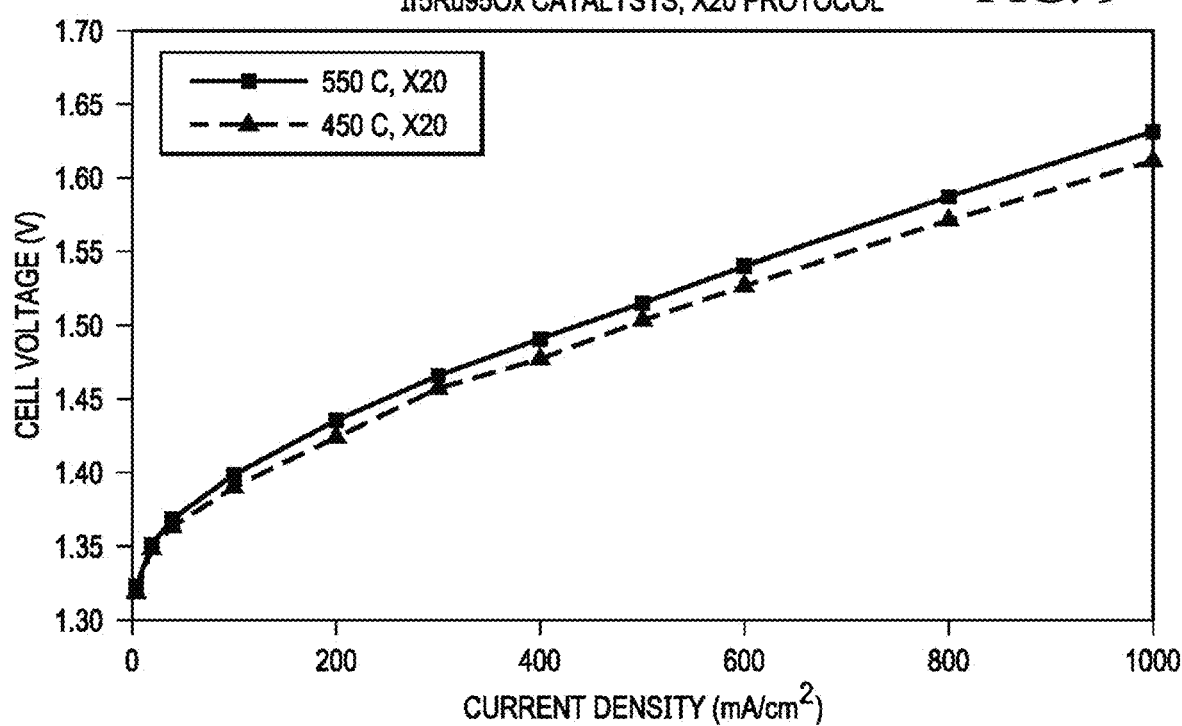
FIG. 9 shows results from a single cell for $Ir_5Ru_{95}O_x$ catalysts synthesized with X20 protocol at 450 and 550° C. temperatures (synthesis temperature optimization). $Ir_5Ru_{95}O_x$ catalyst that was synthesized at 450° C. temperature demonstrated the best performance with five-mil thick Nafion membrane at a 75° C. cell temperature in the anode-fed mode. No backpressure.

After the optimal molar ratio and optimal synthesis protocol parameters were identified, the effects of synthesis temperature were investigated. $Ir_5Ru_{95}O_x$ catalyst samples were synthesized via X20 protocol at 450 and 550° C. temperatures and the single cell results are given in FIG. 9. $Ir_5Ru_{95}O_x$ catalyst that was synthesized at 450° C. demonstrated higher performance than the 550° C. synthesized catalyst sample.

In terms of synthesis temperature, while this patent is not limited to the following temperature ranges, it is preferred to have 300 to 550 C, more preferably 400 to 500 C, even more preferably, 440 to 460 C in order to get the best electrocatalytic activity for mixed metal oxide material.

Optimization of the platinum and gold loading (surface decoration of mixed metal oxide material). After identifying the optimal molar ratio, synthesis protocol and synthesis temperature parameters, Pt and Au loading optimization was carried out. Platinum decoration of metal oxides generates a downshift of the d-band center of Pt atoms and this prevents strong adsorption of surface species to the electrocatalyst surface. A more weakly bound surface species may be more reactive to form O2 than a more strongly bound one, resulting in a rate enhancement for O2 evolution. Obviously, a weak binding of surface adsorbed reactive oxygen species and a weak adsorption of O2 on Pt surfaces of the deposited Pt/metal oxide electrode can decrease the coverage of the surface species and increase available active sites for water dissociation, leading to higher catalytic activity for OER on the deposited catalyst than on pure Pt or on the physically mixed Pt/metal oxide catalyst. Au was used to stabilize the Pt particles for the high potential application for anodic OER.

Pt and Au nanoparticle surface modification was investigated with individual species first to identify the optimal loading value for each platinum and gold alone. Then, the combined optimal platinum-gold loading on Ir5Ru95Ox was verified. The Au loading range was from 0 wt % to 40 wt % with the Pt loading range from 0 wt % to 20 wt %. All Ir5Ru95Ox catalyst samples were synthesized at 450° C. using the X20 protocol.

Figure 10:
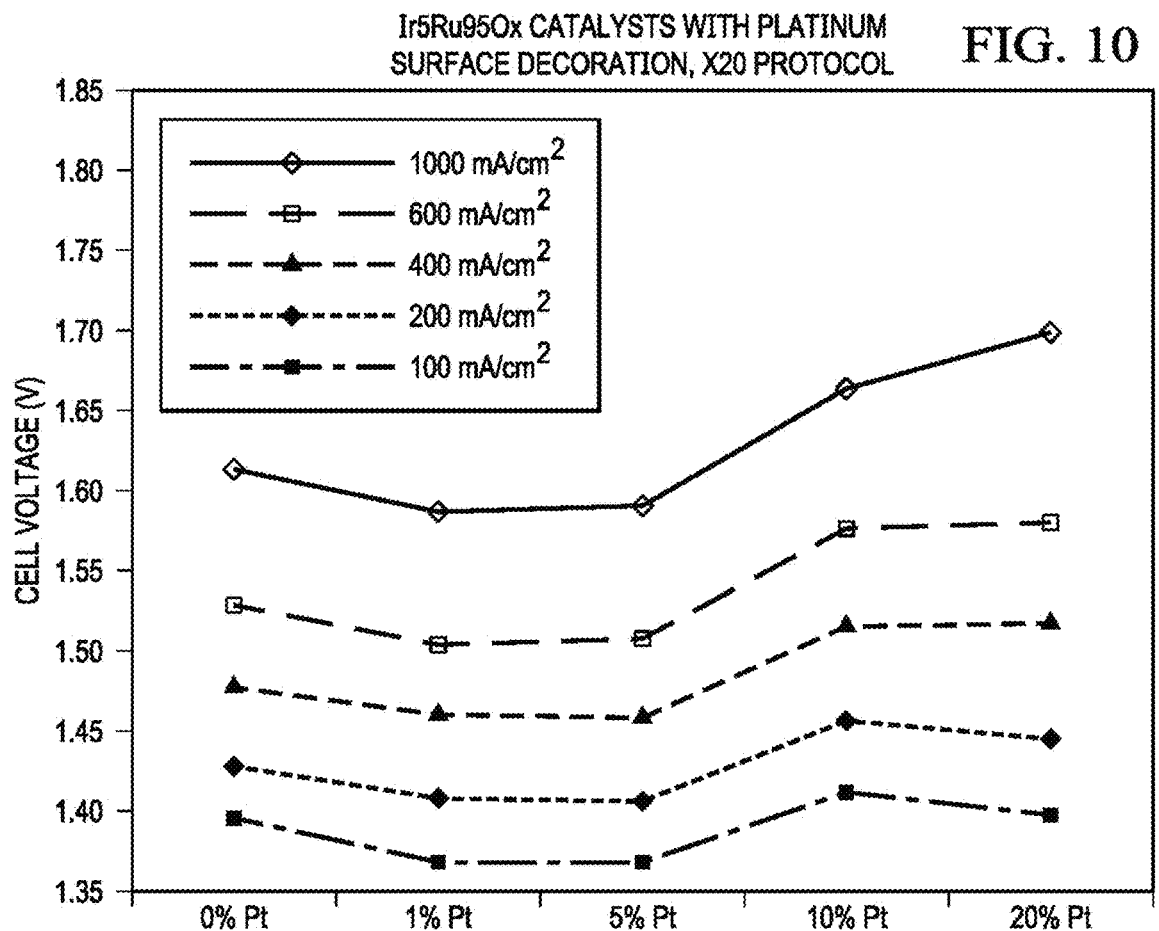
FIG. 10 shows the cell potential as a function of the Pt loading on $Ir_5Ru_{95}O_x$ catalyst at specific current densities (for Pt loading optimization). The Pt loading range tested was from 0 wt % to 20 wt %. Pt nanoparticles were decorated on the surface of the $Ir_5Ru_{95}O_x$. $Ir_5Ru_{95}O_x$ catalysts synthesized with X20 protocol at 450° C. temperature. $Ir_5Ru_{95}O_x$ catalyst with 1 wt % Pt surface modification demonstrated the best performance with five-mil thick Nafion membrane. A 1 wt % Pt nanoparticle surface modification provided a cell voltage of 1.406 V at 200 mA/cm² (87.48% efficiency) at a 75° C. cell temperature in the anode-fed mode. No backpressure.
Figure 11:
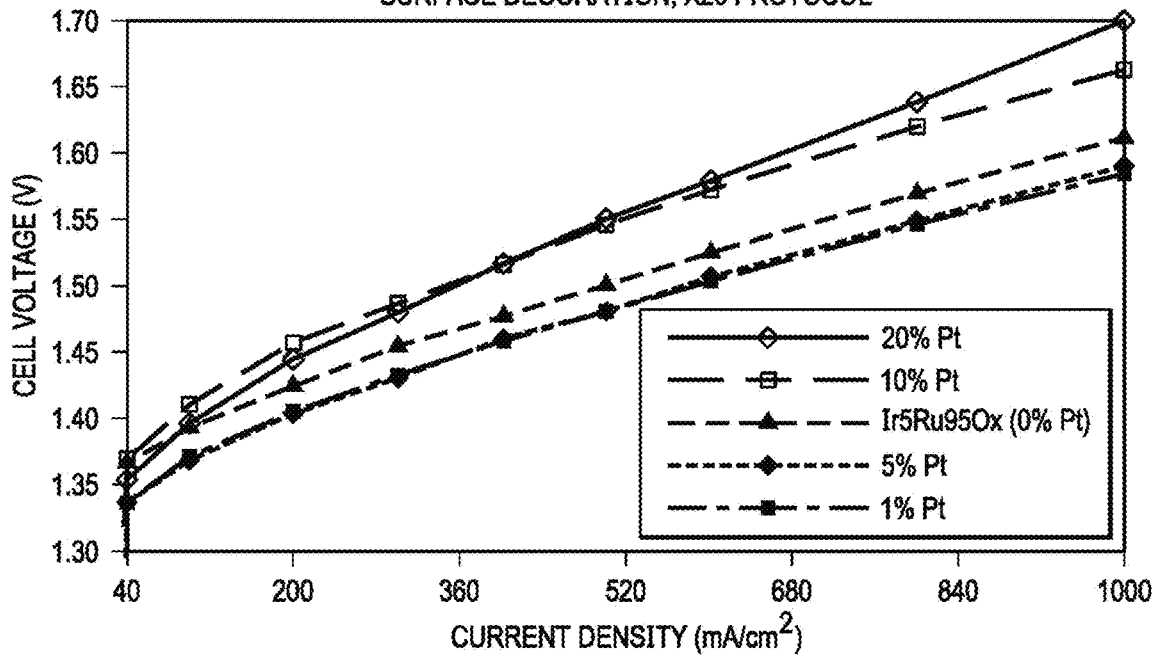
FIG. 11 shows results from a single cell for platinum loading optimization. $Ir_5Ru_{95}O_x$ catalyst with 1 wt % Pt surface modification demonstrated the best performance with five-mil thick Nafion membrane at a 75° C. cell temperature in the anode-fed mode. No backpressure.

Platinum loading optimization single cell results are given in FIGS. 10 and 11. Ir5Ru95Ox catalyst with 1 wt % Pt nanoparticle surface modification demonstrated the best performance.

Figure 12:
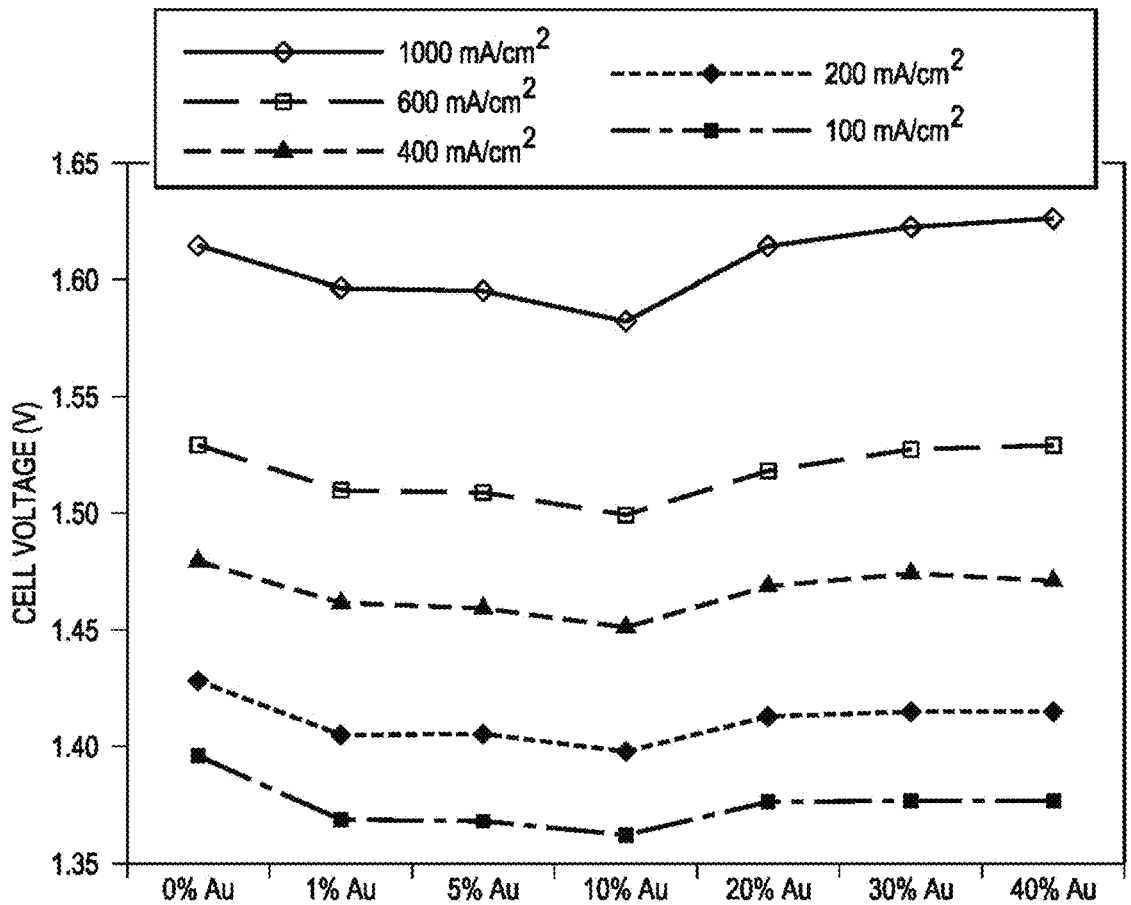
FIG. 12 shows the cell potential as a function of the Au loading on $Ir_5Ru_{95}O_x$ catalyst at specific current densities (for Au loading optimization). The Au loading range was from 0 wt % to 40 wt %. Au nanoparticles were decorated on the surface of the $Ir_5Ru_{95}O_x$. $Ir_5Ru_{95}O_x$ catalysts were synthesized with the X20 protocol at 450° C. The IrsRugsOx catalyst with 10 wt % Au surface modification demonstrated the best performance with five-mil thick Nafion membrane. The 10 wt % Au nanoparticle surface modification provided a cell voltage of 1.398 V at 200 mA/cm² (87.98% efficiency) at a 75° C. cell temperature in the anode-fed mode. No backpressure.
Figure 13:
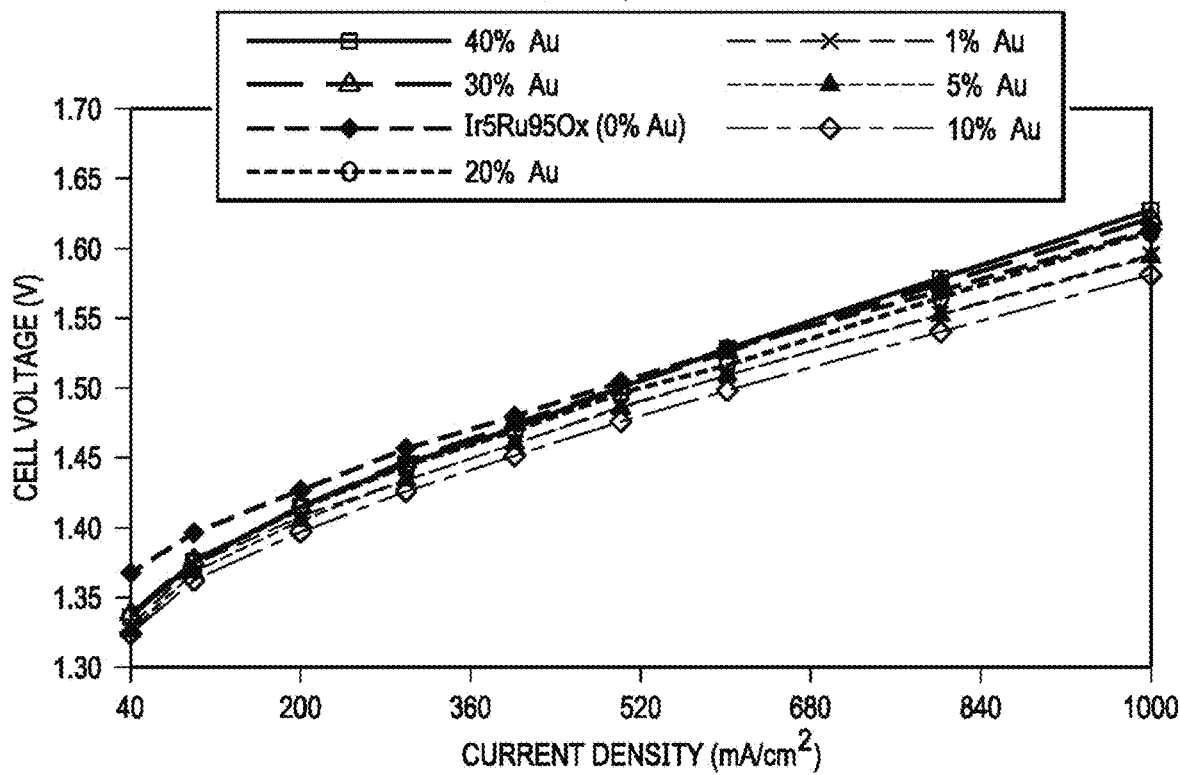
FIG. 13 shows results from a single cell for gold loading optimization. The $Ir_5Ru_{95}O_x$ catalyst with 10 wt % Au surface modification demonstrated the best performance with five-mil thick Nafion membrane at a 75° C. cell temperature in the anode-fed mode. No backpressure.

Gold loading optimization single cell results are given in FIGS. 12 and 13. Ir5Ru95O$_x$ catalyst with 10 wt % Au nanoparticle surface modification demonstrated the best performance.

In one non-limiting example, platinum loading is 0 to 20 wt %, preferably 1 to 10 wt %, or preferably 1 to 5 wt %. The skilled artisan will understand that this patent is not limited to these values, though to get the best electrocatalytic activity and corrosion resilience, 1 to 5 wt % of platinum decoration was found to be optimal.

One preferred gold loading is 0 to 40 wt %, more preferably 1 to 30 wt %, even more preferably 1 to 10 wt %. Again, the skilled artisan will recognize that the amount may be varied to optimize performance, as such, this patent is not limited to these values, though to get the best electrocatalytic activity and corrosion resilience, 1 to 10 wt % of gold decoration was found to be optimal.

One preferred combined platinum-gold loading is 1% Pt with 10% Au in order to achieve the highest efficiency for hypoxia device. Again, the skilled artisan will recognize that the amount may be varied to optimize performance, as such, this patent is not limited to these values, though to get the best electrocatalytic activity, highest efficiency, and corrosion resilience, 1% Pt with 10% Au were found to be optimal.

Figure 14:
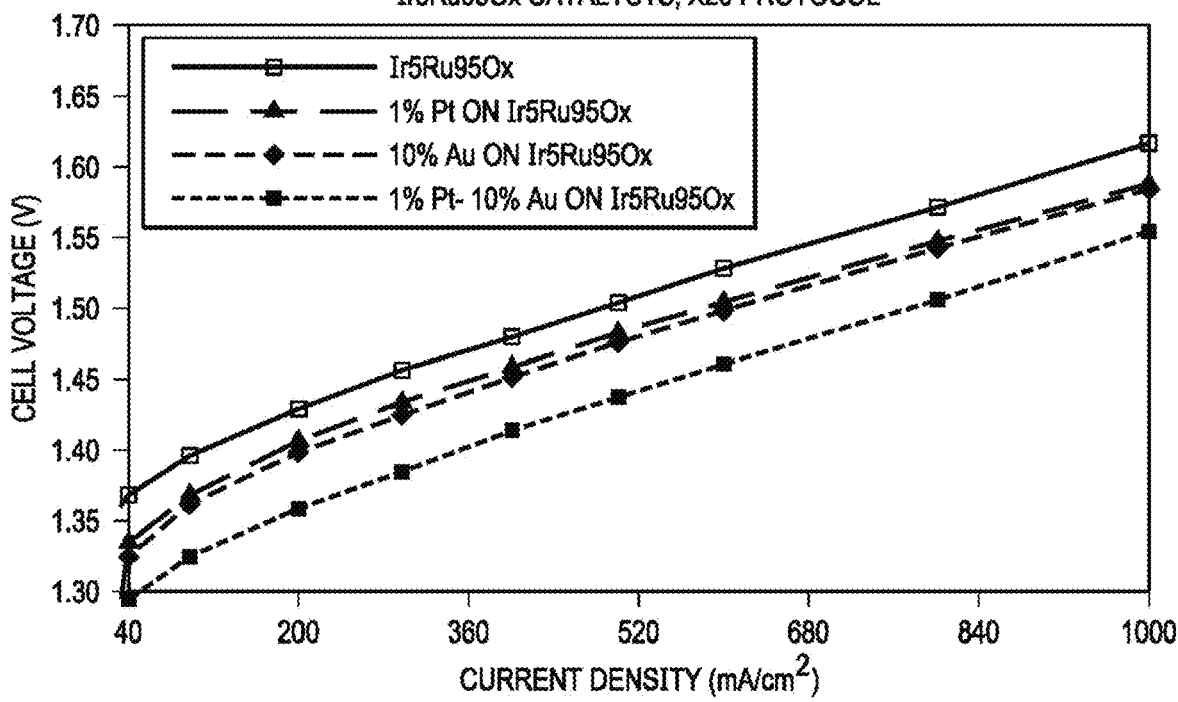
FIG. 14 shows results from a single cell for verification of combined optimal platinum-gold loading optimization. $Ir_5Ru_{95}O_x$ catalyst with 1 wt % Pt-10 wt % Au surface modification demonstrated the best performance with five-mil thick Nafion membrane. The 1 wt % Pt-10 wt % Au surface modified catalyst demonstrated a cell voltage of 1.358 V at 200 mA/cm² (90.5% efficiency) at a 75° C. cell temperature in the anode-fed mode. No backpressure.

For the combined optimal platinum-gold loading performance verification, 1 wt % Pt-10 wt % Au nanoparticles were decorated on the Ir5Ru95O$_x$ catalyst surface. The Ir5Ru95O$_x$ catalyst was synthesized at 450° C. using the X20 protocol. Single cell results for the verification of the combined optimal platinum and gold loading with Ir5Ru95O$_x$ catalyst was given in FIG. 14. A cell voltage of 1.358 V at 200 mA/cm$^2$ was obtained with 1 wt % Pt-10 wt % Au nanoparticles surface modified Ir5Ru95Ox (with a five-mil thick Nafion membrane) and this corresponds to 90.5% MEA efficiency.

Interestingly, the optimal Pt and Au decorations procedure produce similar improvements in performance over the basic oxide. When combined, they produce an improvement about equal to the sum of the two individual contributions. It was expected the combination of Pt and Au to be better than the individual elements, but the magnitude is surprisingly very high.

Figure 15:
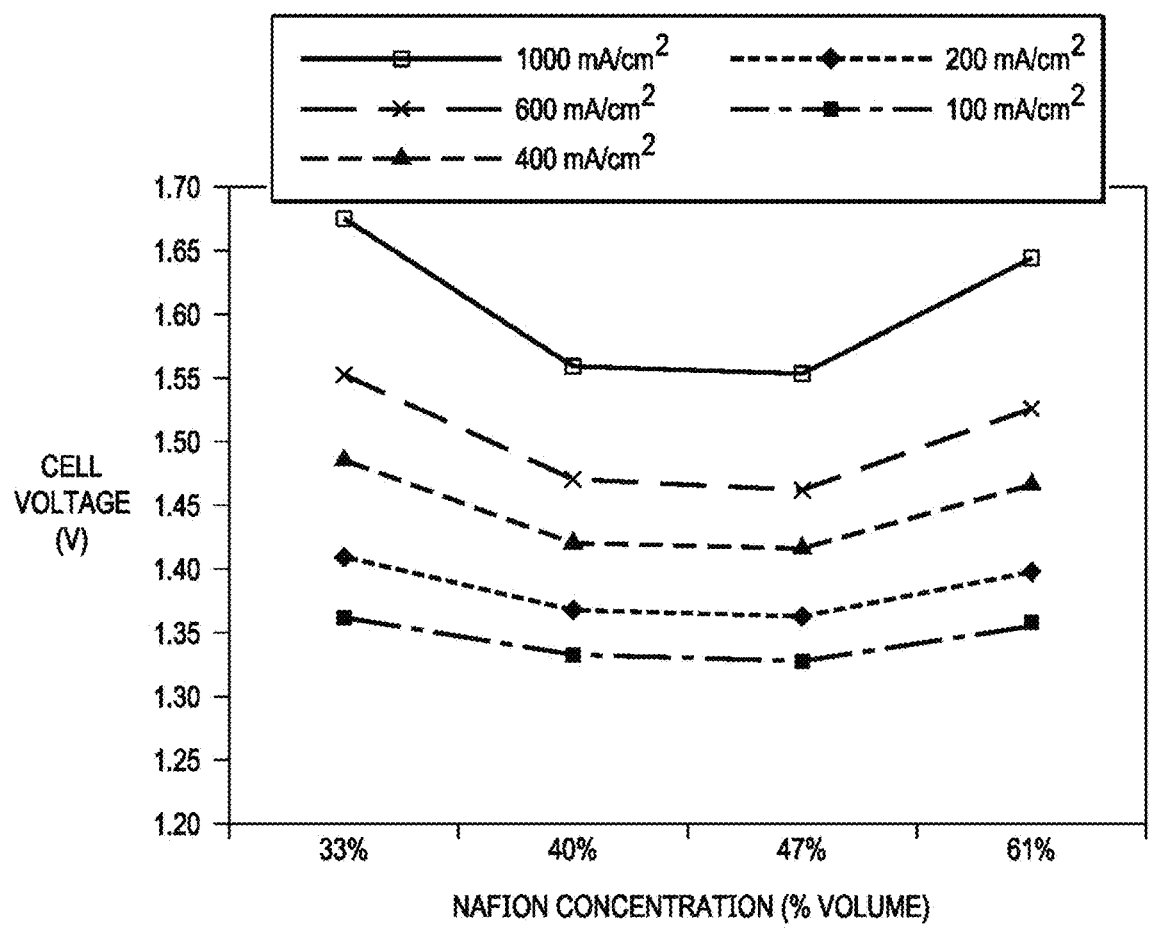
FIG. 15 shows cell potential as a function of the Nafion ionomer concentration in the anode catalyst layer. Optimized anode catalyst with 47 vol % Nafion ionomer in the catalyst layer demonstrated the best performance with five-mil thick Nafion membrane at a 75° C. cell temperature in the anode-fed mode. No backpressure.

Effect of Nafion loading in the anode catalyst layer. The content of Nafion material in the anode electrocatalyst determines the ionic conductivity and electrical conductivity. It is critical to have good ionic conductivity and satisfactory electrical conductivity. The optimal Nafion ionomer concentration for the optimized anode catalyst was investigated in the range of 33 vol % to 61 vol %. Single cell results are provided in FIG. 15. The anode catalyst layer with 47 vol % demonstrated the best performance. This confirms the Nafion content we have been using.

The preferred Nafion volume percent in the hypoxia anode is 33 to 61%, more preferably 40 to 55 volume %, even more preferably 45 to 50 volume %. Again, the skilled artisan will recognize that the amount may be varied to optimize performance, as such, this patent is not limited to these values, though to get the best ionic conductivity and electrochemical performance, a range of 45 to 50 volume % of Nafion is needed at the hypoxia anode side.

Atmospheric air is composed of ~21% oxygen. Additionally, it has been shown that this percentage is closely maintained even up to 30,000 ft altitude. However, the atmospheric pressure changes significantly with altitude. This change in total pressure directly corresponds to the partial pressure of oxygen and is the reason humans struggle breathing at elevated altitudes (FIG. 16).

Figure 16:
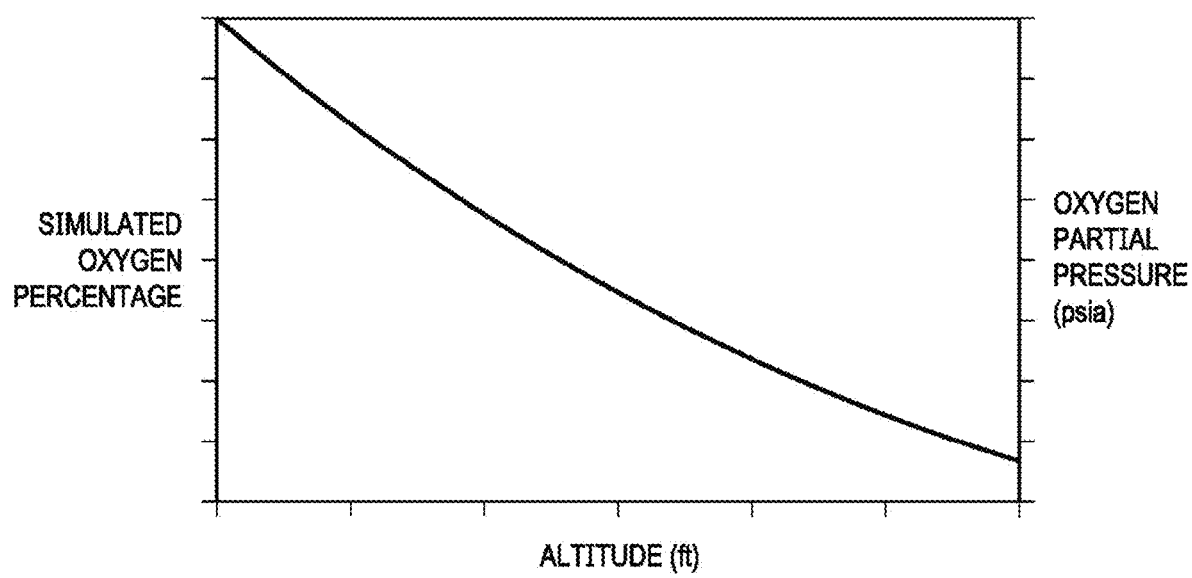
FIG. 16 shows simulated oxygen percentage and oxygen partial pressure as a function of altitude.

Therefore, in order to simulate an elevated altitude under normobaric conditions, the partial pressure of oxygen (simulated oxygen percentage) must be reduced to match the values shown in FIG. 16. The present invention was used in the hypoxia simulation device as a curve fit to FIG. 16, which was used to determine the required oxygen partial pressure for a given target altitude based on the following equations:

$$y = -4.364E - 14x^3 + 7.452E - 09x^2 = 5.281E - 04x + 1.469E + 01$$

$y$ = simulated atmospheric pressure($psia$), $x$ = altitude (feet)

Removing oxygen from an air stream was accomplished utilizing an electrochemical oxygen separation device and technique of the present invention. This technology directly and selectively removes oxygen from the air. Due to the reliability of the electrochemical reactions, the amount (mass) of oxygen removed is directly proportional to the electrical current passed through the electrochemical cells. This correlation results in approximately 3.5 std ml/min of oxygen removal per amp of current. The derived electrochemical reactions, combined with the previously discuss altitude/pressure relations are used, along with the measured inlet air flow rate, are used to determine the required electrical current to achieve a given simulated altitude. These relations are presented below in expanded form for clarity.

Inlet Oxygen rate (slpm)=Total inlet rate (slpm) *20.945% O2

Oxygen Partial Pressure (psia)=Simulated Atmospheric Pressure (psia)*20.945% O2

Simulated oxygen percentage=Oxygen Partial Pressure (psia)/14.668 (psia)

Nitrogen rate (slpm)=Total inlet rate (slpm)*(100%− 20.945% O2)

Total outlet rate (slpm)=Nitrogen rate (slpm)/(100%− simulated oxygen percentage)

Outlet Oxygen Rate (slpm)=Total outlet rate (slpm) *simulated oxygen percentage

Oxygen removal (slpm)=Inlet Oxygen rate (slpm)−
   Outlet Oxygen Rate (slpm)

Total Current (amps)=Oxygen removal (slpm)/0.0035
   (A/slpm)

Stack Current (amps)=Total Current (amps)/# of
   cells in series

The controls work by first measuring the Total inlet air rate (slpm) via the sum of FM-101 & 103. The air flow set point is controlled by the pressure on demand algorithm described hereinabove. The measured flow is multiplied by the assumed oxygen concentration of air to determine the actual amount of oxygen entering the electrochemical stacks. As a first order approximation, 20.945% is used. Although this is a good average for most conditions, several factors can influence the actual percent oxygen in the ambient air. Most notably a combination of relative humidity, temperature and atmospheric pressure can significantly affect the inlet oxygen percentage.

The present invention increases the accuracy of the simulated altitude in part by measuring and accounting for the relative humidity, temperature and atmospheric pressure to calculate the actual oxygen percentage of the air. As a secondary measure, an oxygen sensor is also used to verify the actual ambient oxygen partial pressure. This redundant measure enables the device to self-verify the oxygen concentration and notify the user if the accuracy of the delivered simulated altitude air is in question. As a tertiary measure, an oxygen sensor is also used to measure the oxygen concentration of the outlet stream.

As mentioned previously, the target outlet oxygen partial pressure is determined via the altitude set point. This measure is used to determine the required amount of oxygen needed in the outlet stream to achieve the target-simulated altitude. From here the required amount of oxygen that needs to be removed is used to determine the electrical current required. These relations are calculated real time via the onboard microprocessor to actively control the delivered simulated altitude flow accurately.

Hypoxia training involves exposing personnel to profiles of oxygen concentrations that vary as a function of time. The oxygen concentration is varied as a function of time to simulate changes in altitude above sea level. Various profiles may be created to represent changes of altitude at various rates as well as various altitude extremes and hold times at intermediate altitudes. In order to allow for the electrochemical system to remove oxygen from the air, a significant amount of electrical power is needed. The electrical power required is a function of the altitude that is being simulated and the required flow rate. As the simulated altitude increases, additional electrical power is needed to remove the required amount of oxygen from the ambient air. At high simulated altitudes the required electrical power exceeds that available from common 120Volt AC (Alternating Current), 15 amp or 20 amp power outlets. In order to allow for a hypoxia training device to operate with altitude profiles that include high altitudes (30,000 ft and beyond) and high flow rates (50 slpm and beyond) without exceeding the available AC power, a hybrid power management and energy storage system is required. The system stores energy during the lower power portions of the altitude profiles and makes use of the stored energy to supplement the power available for the AC power input during the higher power portions of the altitude profiles.

Figure 17:
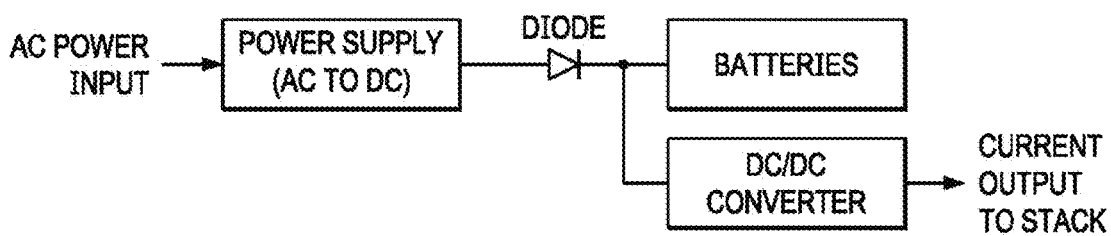
FIG. 17 shows the hybrid power management and energy storage system.

FIG. 17 shows a hybrid power management and energy storage system for use with the present invention. The system operates as follows. A power supply is used to convert the AC input power to DC (Direct Current) power. This power supply incorporates both voltage and current limiting. The voltage limiting is used to limit the voltage to which the battery (or batteries) used for energy storage is (are) charged. The current limiting is used to assure that that power drawn for the AC power input does not exceed that available from the AC power circuit (typically 15 to 20 amps). The diode connected to the output of the power supply is used to protect the power supply from reverse voltage in the event of the power to the supply being turned off or disconnected. The DC/DC converter is used to convert the power supplied form the power supply and the battery (or batteries) into the voltage required to drive the electrochemical stack with the current required to remove the amount of oxygen required to simulate the altitude. The output voltage of the DC/DC converter is adjusted by a control system as required for the output current from the DC/DC converter to follow that required by the simulated altitude profile. The DC/DC converter may be a buck converter, a boost converter or a buck/boost converter depending upon the required stack voltage relative to the battery voltage. If the stack voltage is always higher than the battery voltage, a boost converter is required. If the stack voltage is always lower than the battery voltage, a buck converter is required. If the stack voltage may be higher or lower than the battery voltage, a buck/boost converter is required.

The batteries are charged during periods of the simulated altitude profile that require less power than is available from the AC power input and discharged during periods of the simulated altitude profile that require more power than is available from the AC power input. Current flows into the battery if it is not fully charged and excess power is available. Current flows out of the battery when more power is required to simulate the required altitude than is available from the AC power input. If the required altitude profile to be simulated requires more energy to be provided to the battery than is available during the profile, a battery recharge time is required to allow for adequate energy to be provided the battery prior to running a new profile.

Description of pure oxygen capability. A key advantage of the electrochemical oxygen separation of the present invention is the production of a high purity oxygen stream. As the air stream on the cathode is depleted of oxygen, the anode stream becomes oxygen enriched. In fact, the net effect of the electrochemical reactions is that for every oxygen molecule removed from the cathode, one oxygen molecule is produced at the anode. In this way, only oxygen and water are produced on the anode. After the water is removed through phase separation, only saturated oxygen remains.

The present invention maximizes the usefulness of this secondary oxygen production by temporarily storing it in a storage container at atmospheric pressure. This temporary storage enables the device to deliver up to 5 minutes of pure oxygen to the pilot for rapid recovery from the hypoxic conditions.

During hypoxia simulation, if the pilots SpO2 falls below a given threshold, or if the test administrator observes that the pilot has achieved the hypoxic conditions, the simulation is aborted. SV-101 is closed, and PDP-105 is enable, which quickly delivers pure oxygen to the pilot. This allows the pilot to recover quickly, avoiding any long terms effects for the temporally induced hypoxia.

If the storage container is not connected to the device (optional), or once the oxygen bag is depleted, the pilot will be delivered ~40% oxygen directly from the electrochemical stack anode. As an alternative, regular air may also be delivered to the pilot if desired. Based on the stack control algorithms, any user selectable oxygen percentage may also be delivered to the pilot by diluting the delivered oxygen with additional air.

Implementation of water recovery features to reduce logistics. An important concern in operating the $O_2$ Trainer was maintaining water balance. Air pumped into the electrochemical stacks carry water vapor into the system based on atmospheric conditions. As the air moves through the electrochemical stacks, it leaves at almost 100% relative humidity. Water for air humidification becomes available due to the formation of water from the reaction of hydrogen (from the anode) and oxygen (in the cathode), electro-osmotic drag (due to movement of hydrogen protons to the cathode) and diffusion of water from anode to cathode. In an ideal situation, there would be no electro-osmotic drag or diffusion, hence, maintaining perfect water balance in the coolant loop. Since such a situation isn't realistic, condensers and phase separators must be used to recover water lost from the coolant loop (or anode side).

An appropriately sized condenser is required to cool down the humidified air and, therefore, condense the water vapor. This condensed water vapor can then be recovered into the coolant loop. There are, however, limitations to how much water can be condensed. In condensers, the medium undergoing a phase change, such as boiling or condensation, has an infinite capacitance rate (Capacitance Rate Equation). This is because mediums undergoing phase change do not undergo a change in temperature and, therefore, have an infinite specific heat capacity. In such conditions, heat transfer is limited by the fluid with the much lower capacitance rate that experiences a larger change in temperature than the condensing medium. As the non-condensing fluid (in this case ambient air pushed by a fan) approaches the temperature of the condensing medium (reduced-oxygen air & pure oxygen gas stream) heat transfer rate drops substantially. Hence, it's never possible for the exiting condensing fluid to reach ambient temperature unless an infinitely large heat exchanger or a very large cold fluid flow rate is employed.

Capacitance rate Equation.

$$\dot{C} = \dot{m} \cdot c_p$$

$\dot{m}$ = Mass flow rate; $c_p$ = Specific heat capacity

Phase separators are also necessary to separate the condensed water from the air. This also prevents liquid water from entering fluid loops that deliver gas to the end user and damage to electronics downstream.

Temperature and pressure are two important factors that affect the amount of water vapor in the air. Increasing temperature at constant pressure increases the amount of water vapor dry air can carry. This, however, decreases the relative humidity of the air. Relative humidity is an indicator of the percentage of the maximum humidity the air is carrying. At 100% relative humidity, air is carrying the maximum amount of water vapor and a slight drop in temperature will cause the water vapor to condense to liquid water. Increasing the pressure of air-water vapor mixture increases the partial pressure of dry air and water vapor. This causes the relative humidity to increase and making water vapor condensation easier. Equation 2 shows relative humidity as a function of pressure and Dalton's law applied to system pressure. The pressure of the reduced-oxygen air to the mask is reduced from ~30 psia to ~15 psia to prevent condensation of water vapor in the mask. By reducing the pressure of saturated air-water vapor mixture by half, Equation 2, shows that the partial pressures are reduced by half also. Therefore, at constant temperature, the relative humidity drops to 50%. This also prevents dryness in the end users air passages.

Equation 2: Relative humidity ($) (left), Partial pressures of air-water vapor mixture (right).

$$\emptyset = \frac{P_{vapor}}{P_{saturation\ at\ mixture\ temperature}}; P_{System} = P_{vapor} + P_{dry\ air}$$

Figure 18:
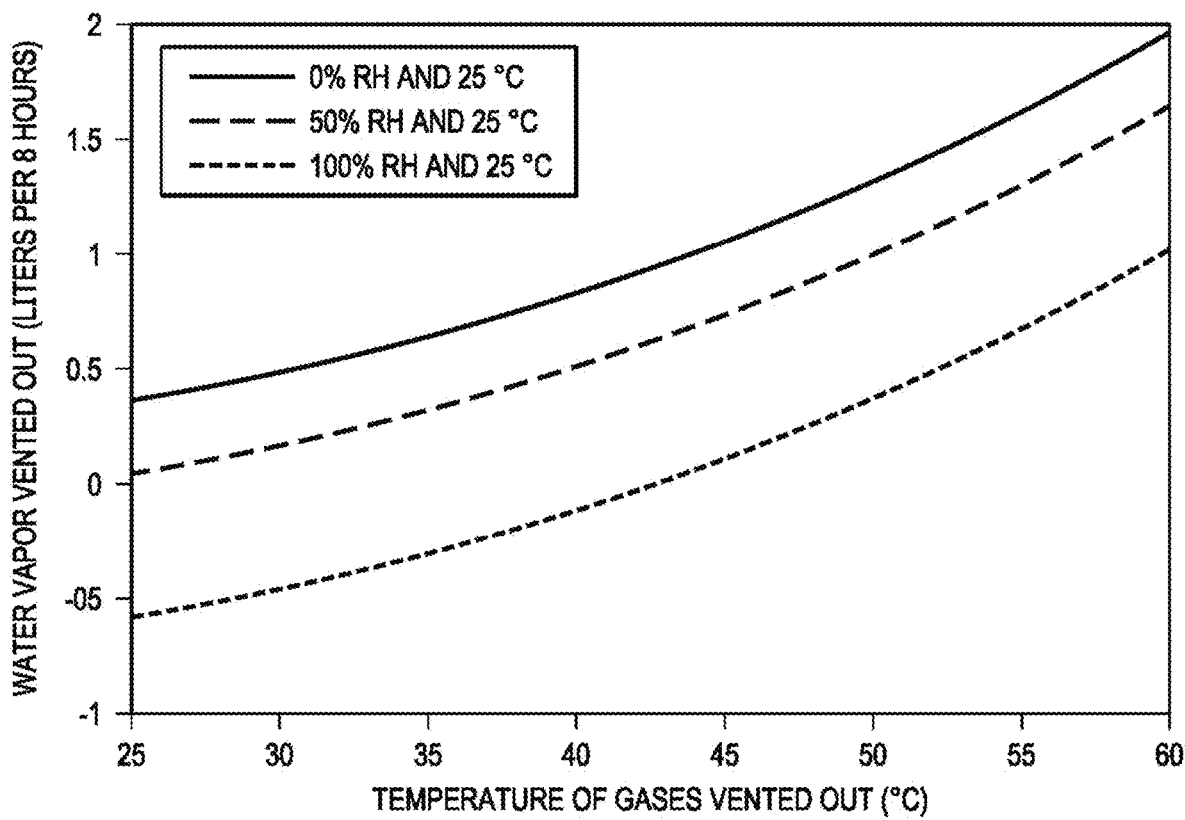
FIG. 18 shows water vapor vented out of the system vs. temperature of vented gases for an incoming air relative humidity of 0, 50 and 100% RH. Water consumption rates without the water recovery condensers are shown at the right (60° C.). Water consumption rates with the water recovery condensers are shown at the left (30° C.).

FIG. 18 shows the sum total of water vapor vented out of the system through the mask supplying reduced oxygen air and the pure oxygen vent. As mentioned above, temperature is one of the major functions that govern water vapor content in dry air; this has been theoretically shown in FIG. 18. FIG. 18 shows the water vapor vented out of the system vs. temperature of vented gases for an incoming air relative humidity of 0, 50 and 100% RH. Water consumption rates without the water recovery condensers are shown at the right (60° C.). Water consumption rates with the water recovery condensers are shown at the left (30° C.).

Also, as the relative humidity of air coming into the system increases the amount of water lost decreases. The highest quantity of water is lost when completely dry air is supplied to the system. On the other hand, by supplying air that is saturated ($\phi$=100%), water is added to the coolant reservoir (depending on outlet temperature & pressure) because the amount of water vapor condensed by the condensers is higher than what is lost in the vented gases.

As the temperature of vented gases increase the amount of water lost increases. For instance, if the gases were vented at 60° C. 2 L to 1 L of water per 8 hours of operation would be lost versus ½ L to 0 L of water. If the incoming air is completely saturated the system would actually gain 0.5 L of water.

Use of an ion exchange resin enables the use of tap water by providing an ion exchange resin for water that comes in contact with the anode. Optionally, an ion exchange resin can also be provided after the anode or the cathode for recycling that water.

The electrochemical oxygen separation device utilizes a Proton Exchange Membrane (PEM), which is selectively conductive to cations. For the purpose of hypoxia simulation, hydrogen protons are transferred through the membrane. However, other charged ions and free radical can also be absorbed into the membrane, reducing the conductivity and thus performance. Many of such ions are present in common tap water. As such, tap water is potentially damaging to the electrochemical stack and must not be used for humidification.

Typically, the present invention uses >10 MOhm*cm De-Ionized (DI) water as a water supply for humidification to replace what water is lost from the system. However, in practical applications, this quality of DI water is not commonly available. Therefore, the present invention incorporates a mixed bed ion exchange resign into the water fill port of the system. This approach allows the user to refill the system with normal tap water without damaging the system.

The present invention also utilizes a DI polishing bed within the system of which the anode water is constantly re-circulated through during operation. This approach added a secondary layer of protection by capturing any contaminating ions, which made it through the initial DI bed during filling. The polishing bed also captures any ions leached out from other metallic components within the anode recirculation loop, thus dramatically extending lifetime.

Other Applications of OER Advanced Catalyst. The first embodiment as it was discussed is the use of the advanced OER electrocatalyst in the electrochemical hypoxia device. In terms of configuration, this device employs liquid water at the anode and air at the cathode. Liquid water is electrochemically dissociated to oxygen, protons, and electrons. While oxygen is stored for emergency or vented out, protons and electrons are transferred to cathode side and reacted with oxygen molecules in the air feed. This later reaction generates oxygen-reduced air stream that is used for hypoxia training of pilots.

The advanced OER electrocatalyst can also be used for one or more of the following applications.

Example 1: Low, medium, and/or high-pressure pure oxygen generators and oxygen compressors (based on electrochemical generation of pure oxygen) can also benefit from the advanced OER electrocatalyst. In terms of configuration, these devices employ liquid water at the anode and utilize the electrolysis reaction in order to produce pure oxygen at different compression pressures. In general such devices are well-known for the oxygen generation and storage at 0 to 400 psi, 400 to 2200 psi, and 2200 to 3600 psi. In terms of electrochemical reactions, at anode liquid water is electrochemically dissociated to oxygen, protons, and electrons. While oxygen is generated and compressed to the desired pressure for the intended applications, protons and electrons are transferred to cathode side, hydrogen gas is produced and usually vented out at atmospheric pressure. Since oxygen compressor devices do not use depolarization mechanism at the cathode, the operating cell voltage for such devices are much higher compared to hypoxia device cells. While it is possible to use cathode depolarization in order to reduce the overall cell voltage, it is not recommended due to the following issues: compressed oxygen gas diffusion to the cathode can create safety issues (creating chemical combustion reaction with hydrogen gas) or contamination of oxygen gas with nitrogen gas.

Example 2: Low, medium, and/or high pressure oxygen concentrators (based on electrochemical generation of oxygen enriched air) can also benefit from the advanced OER electrocatalyst. Such systems are useful for generating 22% to 95% (by volume or weight) oxygen enriched air for numerous industrial and medical applications. In terms of configuration, these devices employ liquid water at the anode and utilize the electrolysis reaction in order to produce pure oxygen at different compression pressures (0 to 3600 psi range). In terms of electrochemical reactions, at the anode liquid water is electrochemically dissociated to oxygen, protons, and electrons. Protons and electrons are transferred to the cathode side and reacted with oxygen in the air feed and a nitrogen enriched air stream is generated. Depending on the desired oxygen enrichment, pure oxygen generated at the anode is mixed with the appropriate ratio of nitrogen enriched stream in a gas mixing chamber and utilized. Since oxygen concentrator devices use depolarization mechanism at the cathode (electrochemical reaction of protons and electrons with oxygen molecules in the air without forming chemical combustion reactions), the operating cell voltage for such devices are comparable to electrochemical hypoxia device cells.

Example 3: Electrochemical inerting systems (that are based on electrochemical generation of nitrogen enriched air) can also benefit from the advanced OER electrocatalyst. Such systems are useful for generating 0% to 95% (by volume or weight) nitrogen enriched air for numerous industrial inerting applications (such as inerting of the fuel tanks for military fuel tankers, inerting of ship and airplane fuel tanks for commercial and military planes, inerting residential fuel tanks, and other inerting applications that require decreased probability of combustion of any flammable materials stored in a confined space). In terms of configuration, an electrochemical inerting device will employ liquid water at the anode and utilize the electrolysis reaction in order to produce pure oxygen (usually at ambient pressure). In terms of electrochemical reactions, at the anode liquid water is electrochemically dissociated to oxygen, protons, and electrons. Protons and electrons are transferred to the cathode side and reacted with oxygen in the air feed and a nitrogen enriched air stream is generated. Depending on the desired nitrogen enrichment, multiple electrochemical inerting systems can be used to achieve much greater nitrogen enrichment levels such as >95%. While oxygen generated at the anode is usually vented out, the nitrogen enriched stream generated at the cathode is used for inerting applications. Since electrochemical inerting devices use depolarization mechanism at the cathode (electrochemical reaction of protons and electrons with oxygen molecules in the air without forming chemical combustion reactions), the operating cell voltage for such devices are comparable to electrochemical hypoxia device cells and lower than pure oxygen compressors.

Example 4: Low-, medium-, and/or high-pressure pure hydrogen generators and hydrogen compressors (based on electrochemical generation of pure hydrogen) can also benefit from the advanced OER electrocatalyst. In terms of configuration, these devices employ liquid water at the anode and utilize the electrolysis reaction in order to generate protons, which are then recombined at the cathode to produce pure hydrogen gas. In general such devices are well-known for the oxygen generation and storage at 0 to 400 psi, 400 to 2200 psi, and 2200 to 5000 psi or possibly greater than 5000 psi for some niche applications. In terms of electrochemical reactions, at the anode liquid water is electrochemically dissociated to protons, electrons, and oxygen. Due to the electrical gradient, protons and electrons are transferred to the cathode. At zero voltage over a hydrogen gas generation electrocatalyst, protons are recombined and hydrogen molecules are formed. Generated hydrogen gas is then compressed and stored at the desired pressure. Oxygen generated at the anode is usually vented out at ambient pressure. Since electrochemical hydrogen generator and hydrogen compressor devices do not use depolarization mechanism at the cathode, the operating cell voltage for such devices are much higher compared to hypoxia device cells.

Example 5: Low, medium, and/or high pressure proton exchange membrane electrolyzers can also benefit from the advanced OER electrocatalyst. In terms of configuration, these devices employ liquid water at the anode and utilize the electrolysis reaction in order to produce pure oxygen or hydrogen at different compression pressures. In general such devices are well-known for the oxygen generation and storage at 0 to 400 psi, 400 to 2200 psi, and 2200 to 3600 psi. Proton exchange membrane based electrolyzer devices can also be used to generate pure hydrogen gas and store it at the desired pressure (0 to 5000+psi). In terms of electrochemical reactions, at the anode liquid water is electrochemically dissociated to oxygen, protons, and electrons. For generation of pure oxygen, no cathode depolarization approaches are used. For generation of pure hydrogen, oxygen is vented out at ambient pressures.

Example 6: Electrochemical gas and liquid sensor devices can also benefit from the advanced OER electrocatalyst. In terms of configuration, these devices generally take samples of gases from different environments and measure the concentration of target gas by oxidizing or reducing the target gas at an electrode and measuring the resulting current. The OER electrocatalyst material can detect the following gases (but this patent is not limited to these target gases): nitrous oxides, ammonia, carbon monoxide, carbon dioxide, etc. In terms of electrochemical liquid sensors, the OER electrocatalyst material of the present invention was found to detect pH changes.

Figure 19:
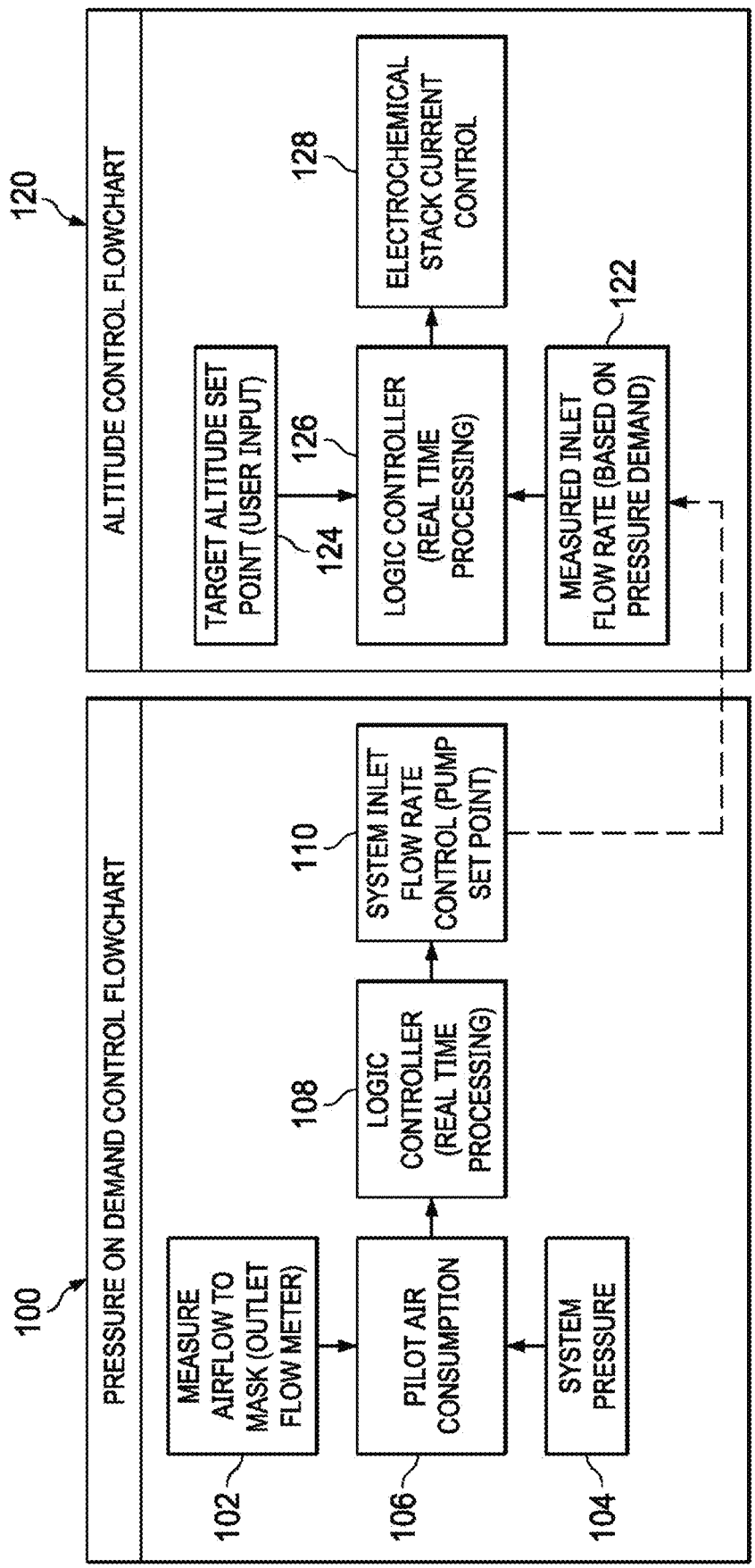
FIG. 19 shows a Pressure on Demand Control Flowchart.

FIG. 19 shows a Pressure on Demand Control Flowchart 100, in which two inputs are provided, measuring the airflow to a mask at an outlet flow meter 102 and a system pressure 104. These two inputs (102, 104) provide a pilot air consumption 106, which data is then provided to a logic controller 108 (which can process in real time), which then controls the system inlet flow rate control pump 110 (at a predetermined pump set point). The data from the system inlet flow rate control pump 110 is then input into the altitude control flowchart 120, which, in conjunction with the measured inlet inflow rate 122 (based on pressure demand) and the target altitude set point 124 (user input), is provided to the logic controller 126 (which can process in real time) and then provides an input into the electrochemical stack current control 128, which varies the current at the stack, which correlates directly to the amount of oxygen generated at the anode, and the amount of oxygen combined with hydrogen to form water at the cathode, thereby varying the final amount of oxygen available at the oxygen air mask.

In FIG. 19, the outlet flow meter 102 is for example FM-102. System pressure 104 can be determined from PT-101 and/or PT or equivalent pressure transducers located between the EOS system and the accumulator ACUM-101. By way of example, control pump 110 can be represented by PDP-101 and/or PDP-102. Measured inlet flow rate 122 can be determined from FM-101 and/or
FM-103.

Figure 20A:
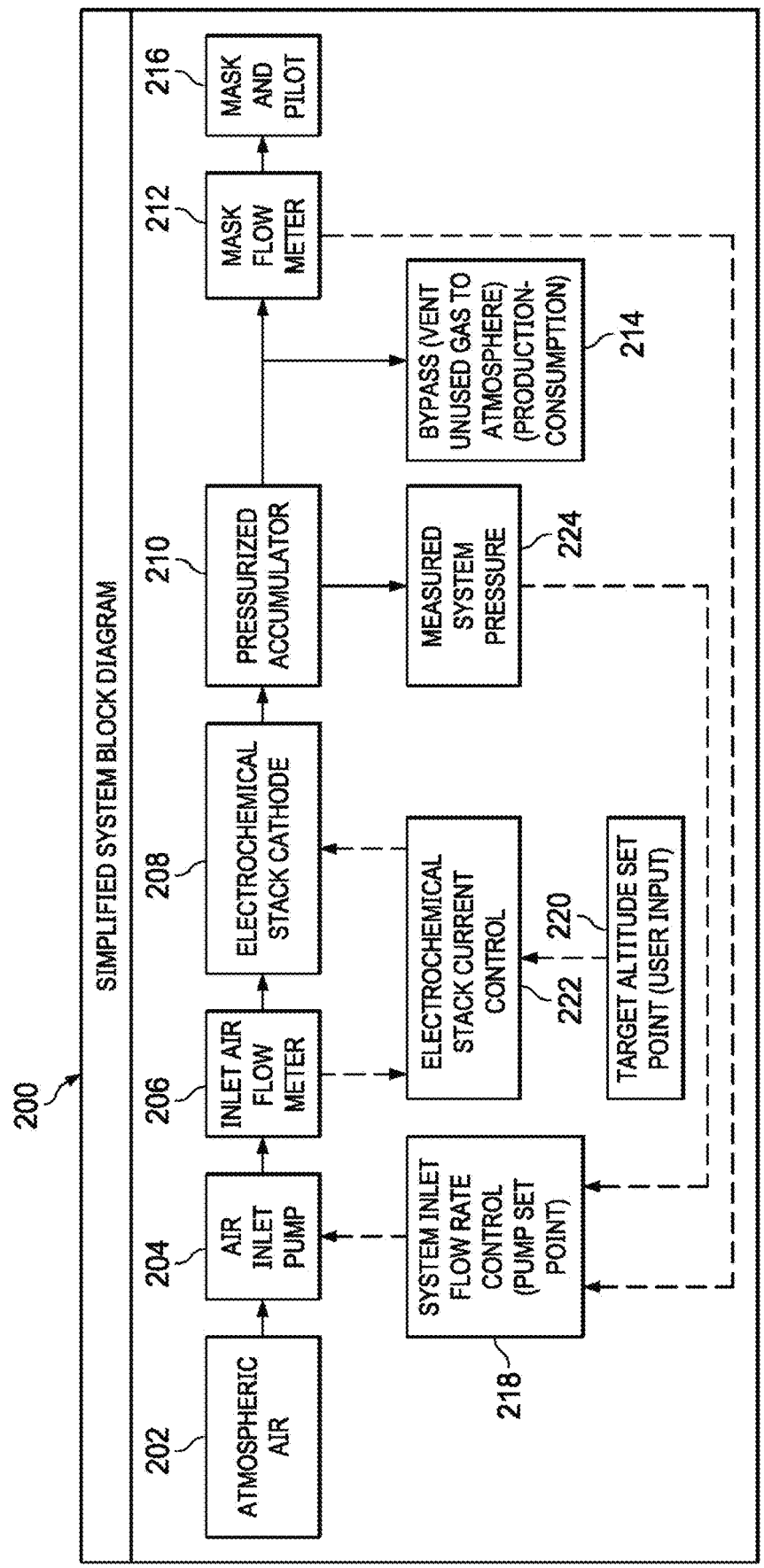
FIGS. 20A to 20B show a simplified system block diagram flowchart.
Figure 20B:
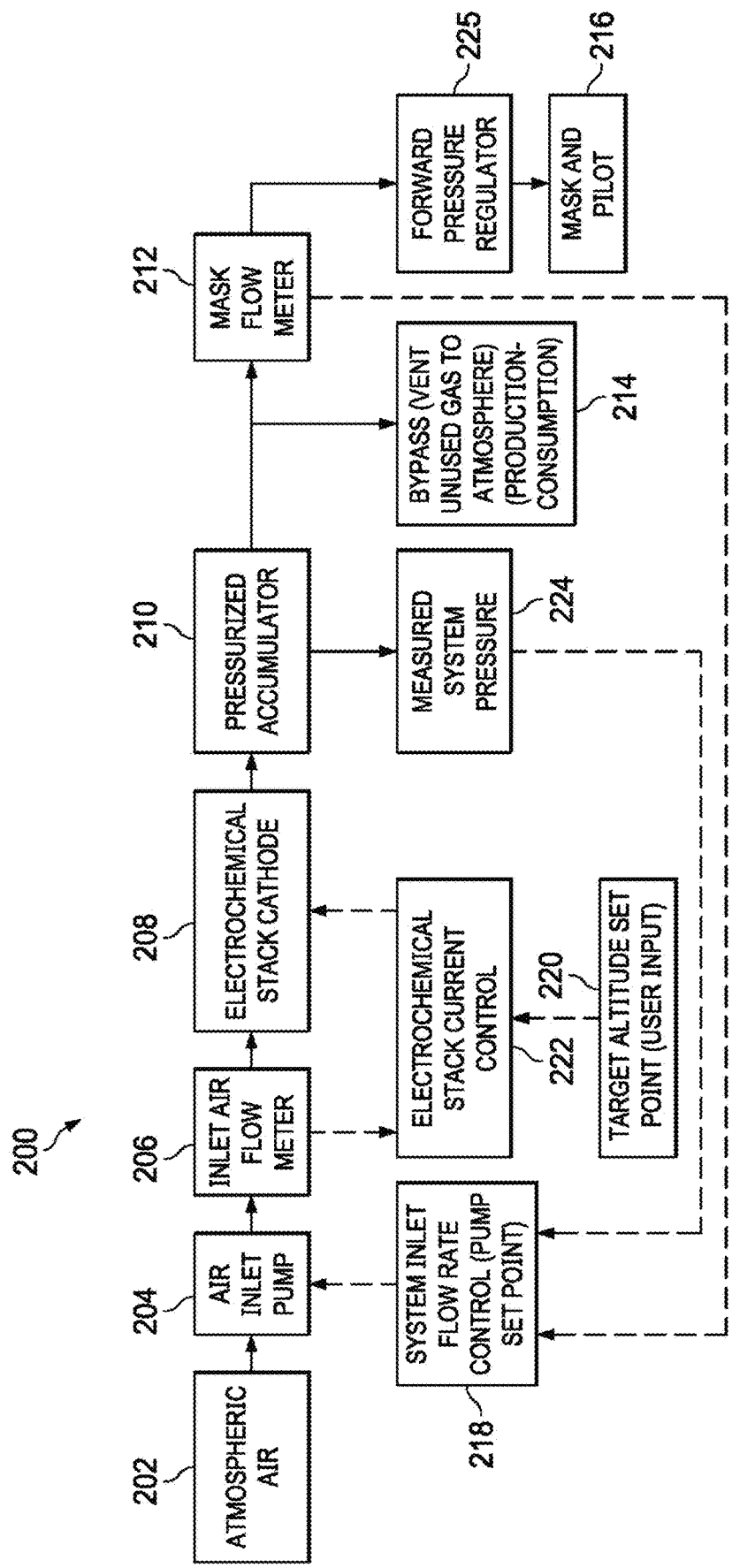

FIG. 20A shows a simplified system block diagram flowchart 200. Atmospheric air 202 enters air inlet pump 204 and the air that exits the air inlet pump 204 is detected at input air flow meter 206. The atmospheric air then contacts one or more electrochemical stacks 2-8 at the cathode, which then enters a pressurized accumulator 210. The air from the pressurized accumulator 210 can be diverted by a valve to a mask flow meter 212, or a bypass 214, which vents unused gas to the atmosphere or production-consumption. The air that traverses the mask flow meter 212 reaches the mask and a pilot at 216. Several inputs are used to modify the flow through the system. First, the mask flow meter 212 is connected to and provides data to the system inlet flow rate control 218 (which controls the pump set-point) and which modifies the output of air inlet pump 204. Second, a user-defined target altitude set point 220 (an altitude setting) is provided to the electrochemical stack current control 222, which in conjunction with information about the amount of air flow at air flow meter 206, controls the amount of current that reaches the electrochemical stack 208, which then controls the amount of oxygen in the atmospheric air that is pulled from the atmospheric air at the electrochemical stack 208. The system inlet flow rate control 218 also received input from the measured system pressure 224, which is measuring the amount of pressure in the pressurized accumulator. In FIG. 20B, a forward pressure regulator 225, is configured to respond to pressure differentials in the conduit connecting the accumulator 210 and the mask.

In FIG. 20A, the air inlet pump 204 can be PDP-101 and/or PDP-102. Input air flow meter 206 is equivalent in function and placement to FM-101 and/or FM-103. Accumulator 210 is equivalent to ACUM-101 and ACUM-102. Mask flow meter 212 is equivalent to FM-102. Bypass 214 is equivalent to BPR-101. Electrochemical stack 208 is equivalent to EOS-101 and EOS-102. System pressure 224 is equivalent to PT-101 and/or PT-103 or equivalent pressure transducers located between the EOS system and the accumulator ACUM-101. In FIG. 20B, the forward pressure regulator 225 is equivalent to FPR-101.

Figure 21A:
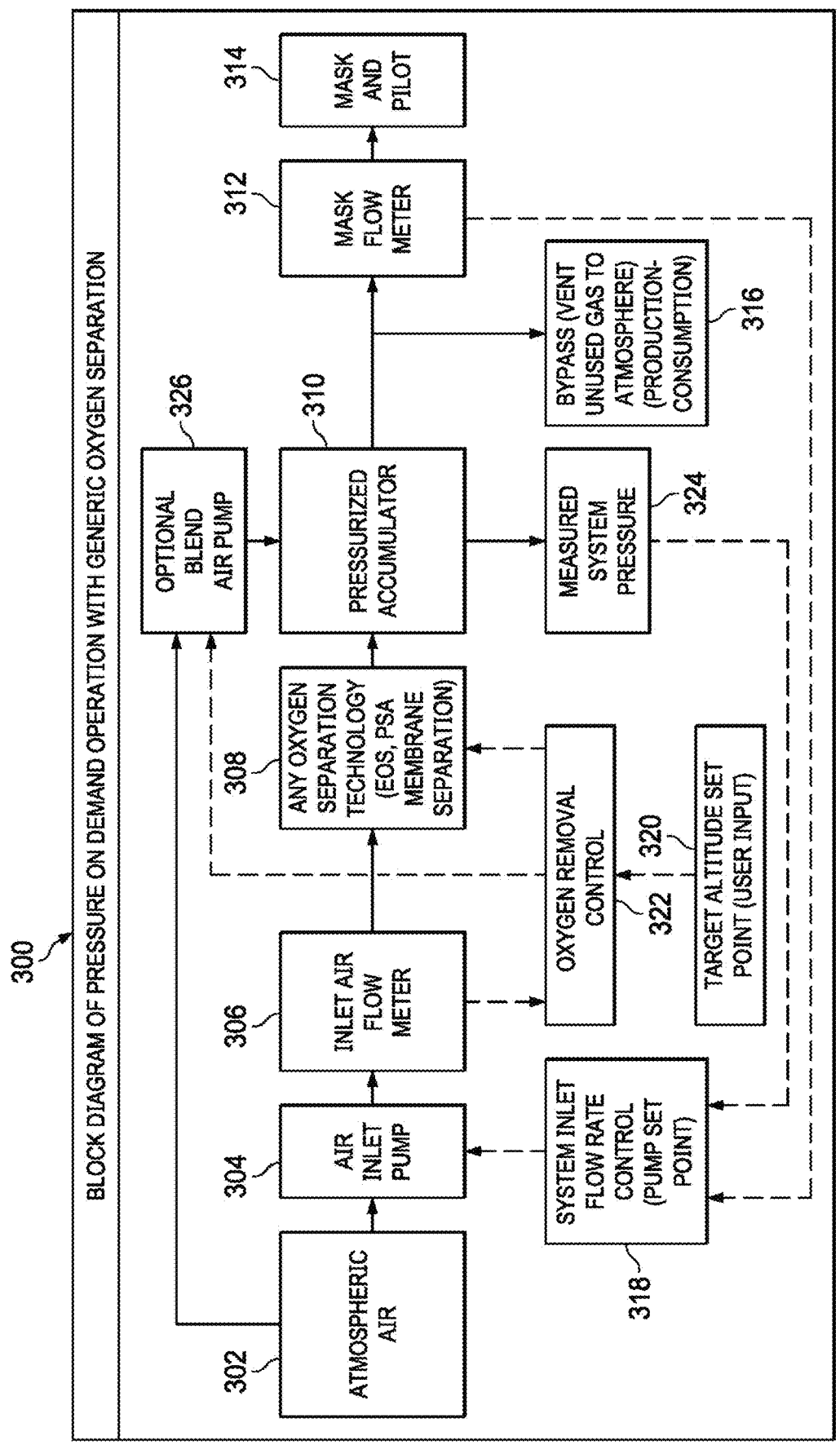
FIGS. 21A to 21B shows a block diagram of pressure-on-demand operation with a generic oxygen separation flowchart.
Figure 22A:
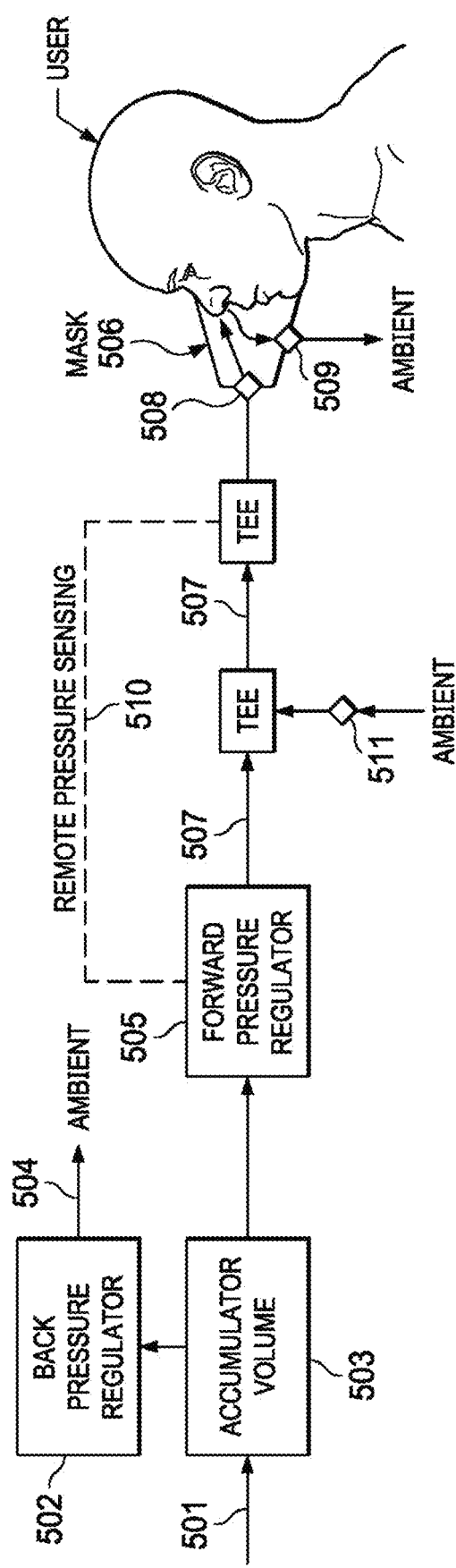
FIGS. 22A to 22B show a diagram of pressure-on-demand operation with a generic oxygen separation.
Figure 22B:
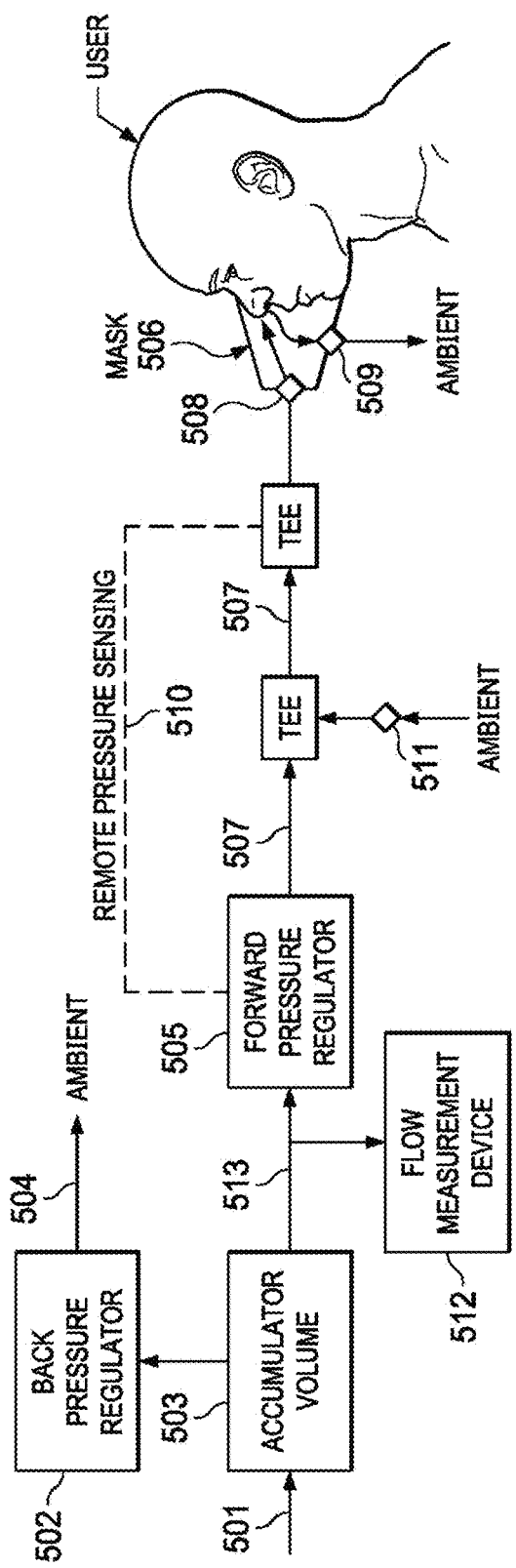

FIG. 21A shows a block diagram of pressure-on-demand operation with a generic oxygen separation flowchart 300. Again, atmospheric air 302 enters an air inlet pump 304, which air flow contact inlet air flow meter 306. The air that flows past the inlet air flow meter 306 then contact an oxygen separator 308 (which can be any oxygen separation technology such as EOS, a PSA membrane, or the like). The output from the oxygen separator 308 enters, e.g., a pressurized accumulator 310 (or can be directly fed to the next step), which is connected via a valve to a mask flow meter 312 and a mask 314, or can be fully or partially bypassed into a bypass 316. As with the system shown in FIG. 20A or 20B, mask flow meter 312 is connected to and provides data to the system inlet flow rate control 318 (which controls the pump set-point) and which modifies the output of air inlet pump 304. Second, a user-defined target altitude set point 320 (an altitude setting) is provided to the oxygen removal control 322, which in conjunction with information about the amount of air flow at air flow meter 306, controls the amount of current that reaches the electrochemical stack 308, which then controls the amount of oxygen in the atmospheric air that is pulled from the atmospheric air at the electrochemical stack 308. The system inlet flow rate control 318 also received input from the measured system pressure 324, which is measuring the amount of pressure in the pressurized accumulator. This embodiment can also include a valve that provides atmospheric air 302 to an optional blend air pump 326 that provides air into the pressurized accumulator 310, under the control of oxygen removal control 322. In FIG. 22B, a forward pressure regulator 325, is configured to respond to pressure differentials in the conduit connecting the accumulator 310 and the mask.

Figure 21B:
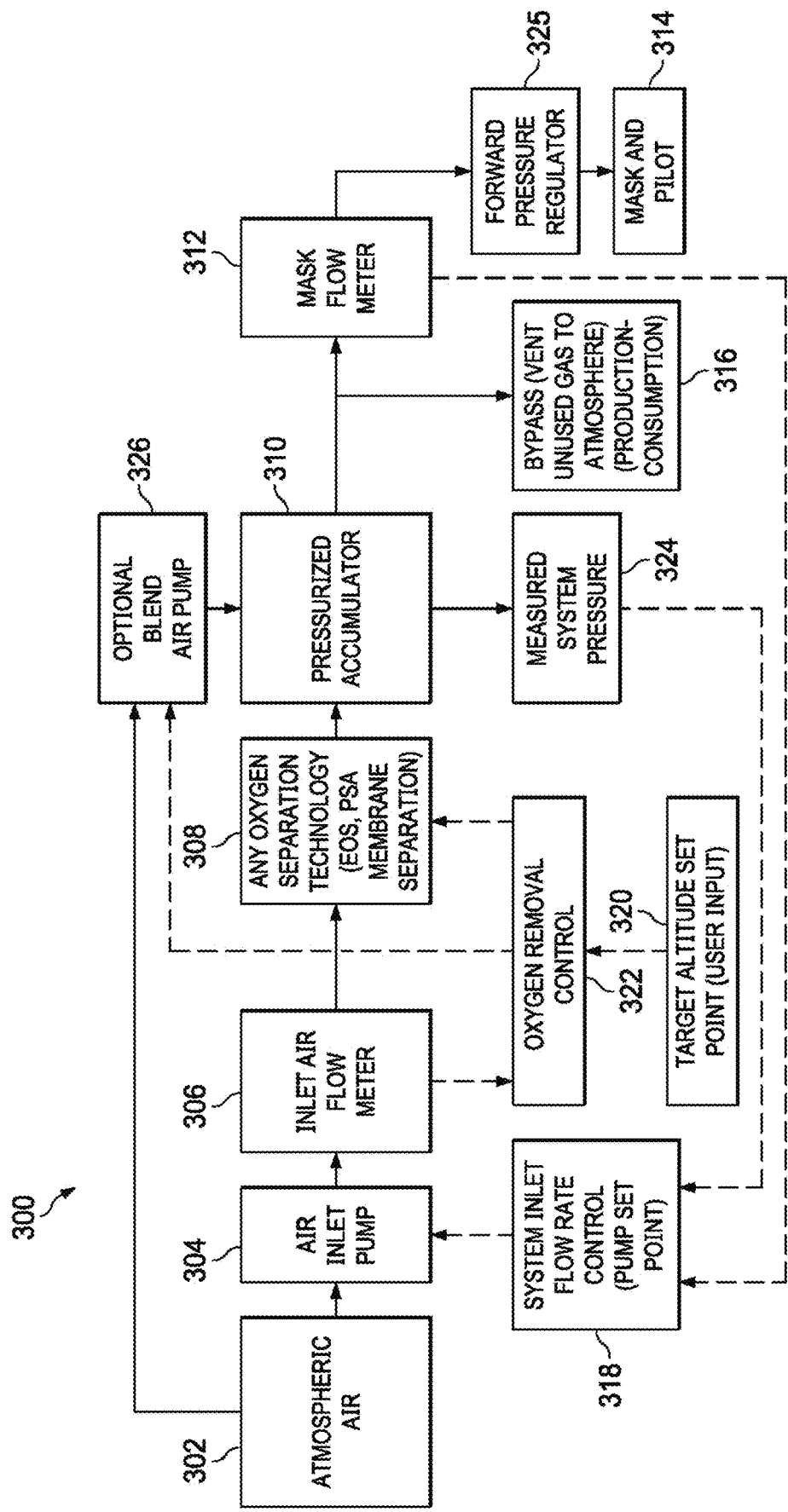

In FIGS. 21A and 21B, air pump 304 can be PDP-101 and/or PDP-102. Inlet air flow meter 306 is equivalent in function and placement to FM-101 and/or FM-103. Pressurized accumulator 310 flow meter 312 is equivalent ACUM-101. Flow meter 312 is equivalent to FM-102. Bypass 316 is equivalent to BPR-101. Electrochemical stack 308 is equivalent to EOS-101 and EOS-102. System pressure 324 is equivalent to PT-101 and/or PT-103 or equivalent pressure transducers located between the EOS system and the accumulator ACUM-101. Forward pressure regulator 325 is equivalent to FPR-101.

Pressure on-demand. FIGS. 22A and 22B show the components of a hypoxia training system 500 that accomplished delivery oxygen depleted gas to a person, providing a pressure on demand capability. Oxygen depleted air enters the system 501. An electrochemical oxygen pump may be used as the source of oxygen depleted air. In one non-limiting alternative, a pressure swing absorption device may be used as a source of oxygen depleted air. In another alternatively, a membrane separation gas processing device may be used. Alternatively, oxygen depleted air may be sourced from compressed gas cylinders, that includes a mechanism for mixing and dilution, typically an oxygen supply or ambient air can be diluted with nitrogen. For example, U.S. Pat. No. 6,871,645, relevant portions incorporated herein by reference, teaches a method of producing nitrogen/oxygen mixtures suitable for use with the current invention.

Each of the above-mentioned methods of preparing oxygen-depleted gas can be used in conjunction with the present invention. Additionally, the above methods can produce gas mixtures that simulate the oxygen concentration of air at various altitudes, such as below:

| Height | Oxygen content (%) |
|---|---|
| Sea level | 21.00% |
| 5000 ft | 17.28% |
| 10,000 ft | 14.08% |
| 15,000 ft | 11.38% |
| 20,000 ft | 9.09% |
| 25,000 ft | 7.11% |
| 30,000 ft | 5.43% |
| 34,000 ft | 4.38% |

In FIG. 22A, the hypoxia training system 500 begins with the concentration of oxygen in the gas 501 entering the system, which is adjustable to simulate an altitude between sea level and 35,000 ft following the table above. Moreover, the oxygen content of the gas entering 501 can be adjusted up or down in "real time" to simulate changes in atmospheric oxygen content experienced when transitioning to a higher altitude or transitioning to a lower altitude. Although other pressures may be used, a suitable gas pressure for oxygen depleted gas entering at 501 is 30 psi. A gas pressure range for use with the present invention is from about 10-40 psi. Gas 501 is directed into an accumulator/gas container 503. The system pressure is maintained at the appropriate upper level by a back-pressure regulator (BPR) 502 in fluid communication with an gas accumulator/container 503. Once the desired pressure is reached, the BPR 502 has the capacity to vent excess gas to the ambient surrounding atmosphere 504 external to the accumulator 503. The BPR 502 setting determines the upper limit of the system pressure.

The accumulator 503 with an exact volume is used to store the gas at a predetermined pressure. The accumulator 503 can be constructed from a number of polymer(s), e.g., polypropylene, metals, ceramics, composites, fiberglass, plastics, etc. Materials for construction of the accumulator 503 can include other polymers, composites or metals such as stainless steel or aluminum.

The larger the internal gas volume of the accumulator 503 the smaller the pressure fluctuation. In one non-limiting example, the size the volume of accumulator 503 and associated system conduits are sized to maintain the gas pressure in the accumulator 503, to minimize the flow requirement for oxygen depleted gas 501 flow entering the system at accumulator 503, but also provide the needed gas flow to the mask 506 according to a breathing pattern of the person or user wearing the mask 506. Maintaining a flow according to the breathing pattern is achieved in conjunction with operation of a forward pressure regulator 505. The forward pressure regulator 505 is operated by an appropriately adjusted PID controller.

The internal gas volume of the accumulator 503 is determined based on the allowable fluctuation of system pressure, a pressure drop through balance of components, and the inlet pressure required by the forward pressure regulator 505.

A forward pressure regulator 505 is required to control delivery of the oxygen depleted gas to the mask 506. The mask 506 used can be the kind typically used in aviation by aircraft pilots and crew. Typically the mask 506 will be a "demand type" also known as a "pressure demand mask". The preferred mask 506 is full face (covers nose and mouth). The mask 506 is typically of plastic, rubber and/or silicone. The mask 506 incorporates a face seal. Typical masks 506 are available commercially from, e.g., GENTEX®, however, other equivalent mask types are available from other manufacturers.

Gas is delivered to the mask 506 through a hose conduit 507. A forward pressure regulator 505 always tries to maintain downstream pressure in conduit 507 at a set point or set points by regulating and making adjusting to allow more or less flow in response to the breathing inhalation/exhalation patterns of the person using the mask 506. The gas pressure in the conduit 507 between the forward pressure regulator 505 and the mask 506 is usually only slightly above (or below) the pressure of the surrounding atmosphere outside the mask 506. The mask 506 also prevents the delivered gas from leaking to the ambient environment by sealing against the users face.

The hypoxia training system in FIG. 22B may be used in conjunction with a flow meter or flow measuring device 512, which is mounted in the conduit 513 between accumulator 503 and FPR 505. The training system may also employ an oxygen sensor mounted in the conduit between accumulator 503 and FPR 505.

The system prevents delivering more flow to the mask 506 via conduit 507 than actually necessary according to—and coordinated with—the inhale and exhale actions of the user at the mask 506. The present invention prevents pressure in the accumulator 503 from dropping below the predetermined threshold during operation of the mask 506 by the user, especially during rapid breathing/high breath flow.

The mask 506 uses a unidirectional valve 508 at the inlet of the mask 506 to prevent exhaled air from going back through the inlet tube to conduit 507. The unidirectional valve 508 is sometimes called the inlet valve or demand valve. The unidirectional valve 508 is generally built into the mask 506 (i.e., is built in to the mask). A pressure-on-demand mask can also has a pressure-biased unidirectional exhale valve 509. This unidirectional exhale valve 509 allows the user to exhale to the environment external to the mask 506 at a pressure only slightly higher than the inlet pressure. The unidirectional exhale valve 509 can also be built into the mask. The unidirectional valves 508, 509 may have an altitude compensation feature, whereby their action is mechanically or electronically coupled to compensate for changing altitudes during flight (e.g., changes ambient atmospheric pressure).

In the Hypoxia Training System, the forward regulator valve 505 is preferably an electronic forward pressure regulator (eFPR) type. For example, the forward regulator valve 505 may be an Alicat Electronic Forward Pressure Regulator. Alternatively, the forward regulator valve 505 may be a mechanical type regulator such as a CRU-103. The forward pressure regulator 505 is used in conjunction with a pressure sensing port 510.

The eFPR pressure sensing port 510 measures the pressure in the mask conduit 507; this is particularly important if a long conduit 507 is used to deliver the product gas due to a pressure drop through along the length of the conduit 507. The sensing port 510 may be made from a plastic tube (internal diameter 3-5 millimeters). The sensing port 510 is connected to hose 507 by a T-junction 512.

The position of the T-junction 511 is important and is, preferably, placed as close to unidirectional valve 508 as possible. Preferably, the distance between the T-junction 511 and the unidirectional valve 508 at the inlet of the mask 506 is 0.1-0.5 inch. Alternatively, the distance can be 0.5-6.0 inches. The pressure sensing port 510 connects to the forward pressure regulator 505. This sensing arrangement provides rapid, continuous and accurate readings of the pressure near or at the inlet valve.

Figure 23:
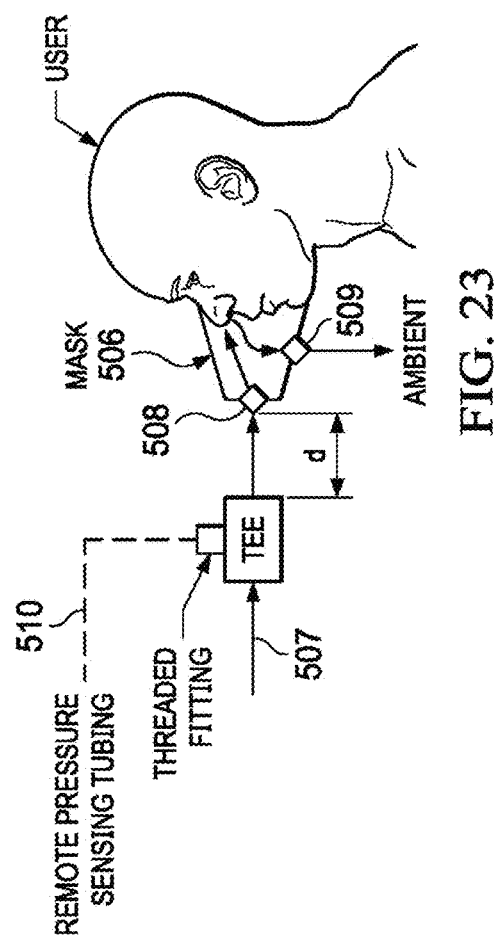
FIG. 23 shows an arrangement of the pressure sensing port.

FIG. 23 shows the arrangement of the pressure sensing port. The feedback from the pressure sensing port 510 allows the forward regulator valve 505 (e.g., an eFPR 505) to open or close to adjust the pressure by increasing or decreasing the flow to the mask 506 based on the pressure at the mask 506 (vs. the pressure at the FPR output which could be considerably higher).

Specifically the eFPR 505, in conjunction with the sensing port, senses an increase in pressure in the conduit 507 when the unidirectional valve 508 at the inlet of the mask 506 closes, during exhalation by the person wearing the mask 506. When this pressure increase is sensed, the eFPR 505 closes to maintain the gas pressure in the accumulator 503 and associated conduits 507. Note that when the accumulator 503 is at its set point upper pressure and the eFPR 505 is closed, oxygen depleted gas 502 entering accumulator 503 can vent through back pressure regulator 502 to the ambient 504. The eFPR 505 in conjunction with the pressure sensing port 510 also detects when a pressure decrease in conduit 507 occurs, that is, when the unidirectional valve 508 at the inlet of the mask 506 opens during inhalation by the person wearing the mask 506. The eFPR is activated to open, to allow reduced oxygen air to exit the accumulator via the hose 507 and enter the mask 506. Thus, the on-demand feature allows gas to leave the accumulator 503 only when it is needed by and according to the users breathing pattern. This has the advantage of allowing pressure in the accumulator 503 and associated conduits 506 to be maintained without depletion over time. The forward regulator valve 505 is useful in another sense. If it were not in a position between the accumulator 503 and the mask 506, the pressure in the accumulator 503 and associated conduits 507 may be at a level where unidirectional valve 508 at the inlet of the mask 506 could open for extended periods. The wearer of the mask 506 would experience excess gas entering the mask 506, could suffer discomfort, and experience difficulty breathing.

Conduit 507 incorporates a unidirectional check valve 511. If the user of the mask 506 breathes at an average flow rate that is much higher than what the system is designed for, the system can depressurize to below a desirable limit. This lower limit is decided based on any minimum pressure limits posed by downstream balance-of-plant components such as the forward pressure regulator 505. In the event the system depressurizes and shuts down, the user may not receive gas sufficient to breathe adequately. In order to prevent breathing discomfort or shortage, the check valve 511 will open. The check valve 511 is in fluid communication with the ambient atmosphere. The check valve 511 is designed to open when the gas pressure in conduit 507 reaches a low value versus the atmospheric gas pressure external to conduit 507. When check valve 511 opens, ambient air from the external atmosphere will be immediately enter conduit 507 and be available to support breathing by the user of the mask 506.

Example 7.

Table 3 depicts key parameters of a hypoxia training device to be used in conjunction with a depleted oxygen source and a pressure on demand pilot's mask.

TABLE 3

Hypoxia trainer: accumulator size as a function of average breath rate, breaths per minute and system pressure fluctuation at a constant inlet flow rate.

| Average Breathing Flowrate (SLPM) | Peak Flow Rate (SLPM) | Breaths per Minute | Upper Limit of System Pressure (psig) | Lower Limit of System Pressure (psig) | Accumulator Volume (L) |
|---|---|---|---|---|---|
| 6.7[+] | 21 | 11.2 | 14.7 | 10 | Not needed* |
| 16.4 | 51 | 14.6 | 14.7 | 10 | 0.5 |
| 25 | 78 | 18.5 | 14.7 | 10 | 1.75 |
| 30 | 94 | 19.1 | 14.7 | 10 | 2.5 |
| 35 | 110 | 21.4 | 14.7 | 10 | 2.75 |

[+]Hypoxia familiarization training by the reduced oxygen breathing method

The Table gives average breathing flow rates, as determined from multiple human studies. The highest ventilation rates observed in human tests is approximately 30+6 LPM. The Hypoxia Training System in Example 7 was sized for this to be the maximum consumption rate (time averaged). Specifically the inlet flow rate of 37.5 SLPM of oxygen depleted gas was used, allowing a margin. The Hypoxia Training Device in this example also accommodates a peak flow rate, calculated based on a sinusoidal breathing waveform (with clipped exhalation) that is a function of tidal volume and breaths per minute; the higher the average breathing flow rate, the higher the peak flow. These values are also from previous human studies. The peak flow rates given in the Table represent the required peak gas flow between the eFPR and the mask via the hose via 507. The Table also shows the number of breaths per minute the device would accommodate.

An electrochemical (EOS) described earlier can provide oxygen depleted air at the desired volume of 37.5 SLPM. Alternatively, a pressure swing absorption device may be used as a source of oxygen depleted air and sized to meet the 37.5 SLPM flow rate. Alternatively, oxygen depleted air may be sourced from one or more compressed gas cylinders, where there is a mechanism for dilution, of oxygen or air with an inert gas such as nitrogen. A compressed gas cylinder source can be sized sufficient to produce 37.5 SLPM of oxygen depleted gas. In this example, the oxygen concentration of oxygen in the gas entering the system at 501 can be adjusted to simulate the concentration of oxygen at altitudes between sea level and 35,000 ft. Moreover, the oxygen content can be adjusted up or down in "real time" to simulate changes in atmospheric oxygen content experienced when ascending and descending.

In this example, oxygen depleted air is added to the accumulator. The gas is supplied under pressure from a pump mechanism connection to inlet 501. The backpressure regulator is set at 14.7 psig, which sets the upper limit of the system pressure. The forward pressure regulator requires a minimum of 10 psig of inlet pressure to allow maximum flow through the regulators. This determines the low limit system pressure. The forward pressure regulator has been selected to allow a peak flow rate of 100 (SLPM) between the accumulator and mask at pressures of 10 psig or greater. An Alicat Electronic Forward Pressure Regulator is used.

Example 7 gives consideration to accumulator gas volume requirement, which is important. In the Table, accumulator size has been assessed according to parameters of average breathing flow rate and breaths per minute of the person using the mask. The assessment shows that the volume requirement of the accumulator needs to be scaled to match the highest values of flow rate and breaths per minute. The assessment indicates an accumulator gas volume of 2.75 L is needed. If a smaller accumulator is used, e.g., 1.75 L, and if the user has an average breathing flow rate of greater than 25 SLPM (as is often the case), the average pressure of in the accumulator and associated conduits could not be maintained close to an average and there would be a fluctuation in pressure wide excursions in pressure. Because of the fluctuations, the pressure for periods of time, will drop to low enough levels that delivery of oxygen depleted gas to the mask would cease to occur. In other words, the pressure would periodically reach the lower limit system pressure of 10 psig. At this point the eFPR would be unable to accommodate the required peak gas flow of 110 SLPM to the mask. The mask's user would experience discomfort when attempting to inhale, due to insufficient volume of gas flowing to the mask. To summarize, Example 1 of a Hypoxia Training System uses approximately 2.75 L (3.0 L with margin) of accumulated volume to store oxygen depleted air at 14.7 psig since this allows the system to undergo a pressure fluctuation of only 4.7 psi with an inlet flow rate of approximately 37.5 SLPM.

Example 8.

Table 4 depicts key parameters of an hypoxia training device to be used in conjunction with a source of oxygen depleted air and a pressure-on-demand pilot's mask. Table 4 gives average breathing flow rates, as determined from multiple human studies as in Table 3. In this example, the Hypoxia Training System is scaled for the maximum consumption rate (time averaged) by the person wearing the mask, allowing for maximum breathing flow rates, which again is 37.5 SLPM of oxygen depleted gas, allowing a margin. In this example, the training system also accommodates a peak flow rate, calculated based on a sinusoidal breathing waveform (with clipped exhalation) that is a function of tidal volume and breaths per minute; the higher the average breathing flow rate, the higher the peak flow. The values given are from previous human studies. The peak flow rates given in the Table represent the required peak gas flow between the eFPR 505 and the mask 506 via the conduit 507. The Table also shows the number of breaths per minute the device would have to accommodate.

TABLE 4

Hypoxia trainer: accumulator size as a function of average breath rate, breaths per minute and system pressure fluctuation at a constant inlet flow rate.

| Average Breathing Flowrate (SLPM) | Peak Flow Rate (SLPM) | Breaths per Minute | Upper Limit of System Pressure (psig) | Lower Limit of System Pressure (psig) | Accumulator Volume (L) |
|---|---|---|---|---|---|
| 6.7 | 21 | 11.2 | 11.7 | 10 | Not needed* |
| 16.4 | 51 | 14.6 | 11.7 | 10 | 1.5 |
| 25 | 78 | 18.5 | 11.7 | 10 | 4.5 |
| 30 | 94 | 19.1 | 11.7 | 10 | 6.5 |
| 35 | 110 | 21.4 | 11.7 | 10 | 7 |

A electrochemical (EOS) described hereinabove can provide oxygen depleted air at the desired volume of 37.5 SLPM. Alternatively, a pressure swing absorption device may be used as a source of oxygen depleted air and sized to meet the 37.5 SLPM flow rate. Alternatively, oxygen depleted air may be sourced from one or more compressed gas cylinders, where there is a mechanism for dilution, of oxygen or air with an inert gas such as nitrogen. A compressed gas cylinder source can be sized sufficient to produce 37.5 SLPM of oxygen-depleted gas. In this example, the oxygen concentration of oxygen in the gas 501 entering the system at can be adjusted to simulate the concentration of oxygen at altitudes between sea level and 35,000 ft. Moreover, the oxygen content can be adjusted up or down in "real time" to simulate changes in atmospheric oxygen content experienced when ascending and descending. Oxygen depleted air is added to the accumulator 503, supplied under pressure from a pump mechanism in fluid connection with the inlet of accumulator 503 to deliver gas 501.

The backpressure regulator 502 is set at 11.7 psig, which sets the upper limit of the system pressure. The forward pressure regulator 505 requires a minimum of 10 psig of inlet pressure to allow maximum flow through the regulators. This determines the low limit system pressure. The forward pressure regulator 505 is generally selected to allow a peak flow rate of 100 (SLPM) between the accumulator 503 and mask 506 at pressures of 10 psig or greater. An Alicat Electronic Forward Pressure Regulator may be used.

Example 8 gives consideration to accumulator gas volume requirement. In the Table, accumulator size has been assessed according to parameters of average breathing flow rate and breaths per minute of the person using the mask. The volume requirement of the accumulator needs to be scaled to match the highest values of flow rate and breaths per minute. This example uses an accumulator gas volume of 7.0 L.

Note that, when the breathing consumption is very small (6.7 SLPM), there is no need for an accumulator since the inlet flow rate is large enough (37.5 SLPM) to provide the peak flow consumed and maintain constant system pressure. This pattern of breathing is not representative however of a person's respiratory physiology. An accumulator is required for higher average breathing flow rates. Accumulator size is a consideration. As the user consumes the gas within the system, the pressure will fluctuate and experience wide excursions in pressure. Because of the fluctuations, the pressure, for periods of time, will drop to low enough levels that delivery of oxygen depleted gas to the mask would cease to occur. In other words, the pressure would periodically reach the lower limit system pressure of 10 psig. At this point the eFPR would be unable to accommodate the required peak gas flow of 110 SLPM to the mask. The person wearing the mask would experience difficulty and discomfort when attempting to inhale, due to insufficient volume of gas flowing to the mask. The average system pressure drop over time, for a given flow rate, is also a function of accumulator volume; a small accumulated volume in the system will cause the pressure to drop rapidly whereas an infinitely large accumulated volume will be able to maintain system pressure. An accumulator of 7 L allows the system to operate at the highest breath flow rates while maintaining system pressure within a desired range.

To summarize, Example 8 of a Hypoxia Training System uses approximately 7.0 L of accumulator volume to store oxygen depleted air at 11.7 psig since this allows the system to undergo a pressure fluctuation of only 4.7 psi with an inlet flow rate of approximately 37.5 SLPM. The data in the table in Table 4 (below) differs from Table 3 (below) that system pressure is lower, therefore pumping equipment for delivering oxygen depleted gas to the accumulator can be scaled back, reducing pump size and or power requirements. This comes at the expense of needing a larger space envelope in the training system to accommodate a larger accumulator.

The present invention may be used in conjunction with full-motion flight simulators to increase training quality and efficiency. The present invention is compact in size, light in weight, and has relatively modest power requirements, so it may therefore be fully integrated onboard typical full-motion flight simulators. Since the present invention may be used with both military and commercial breathing masks, it may be used with typical military and commercial flight simulators.

The present invention enables hypoxia training that includes recognition of incipient and actual hypoxia and switching to one or more oxygen recovery modes to provide a user of the hypoxia training device with an increased oxygen supply to recover from the incipient or actual hypoxia state. The present invention also enables training for a variety of oxygen malfunctions in aircraft flight that includes recognition of the malfunction and switching to one or more oxygen recovery modes to provide a user of the training device with an increased oxygen supply to recover from the malfunction. References herein to the hypoxia training device include any training device encompassed by the present invention that enable training for such oxygen malfunctions. Embodiments of the present invention provide a number of sources for an increased oxygen supply in one or more oxygen recovery modes.

Figure 24:
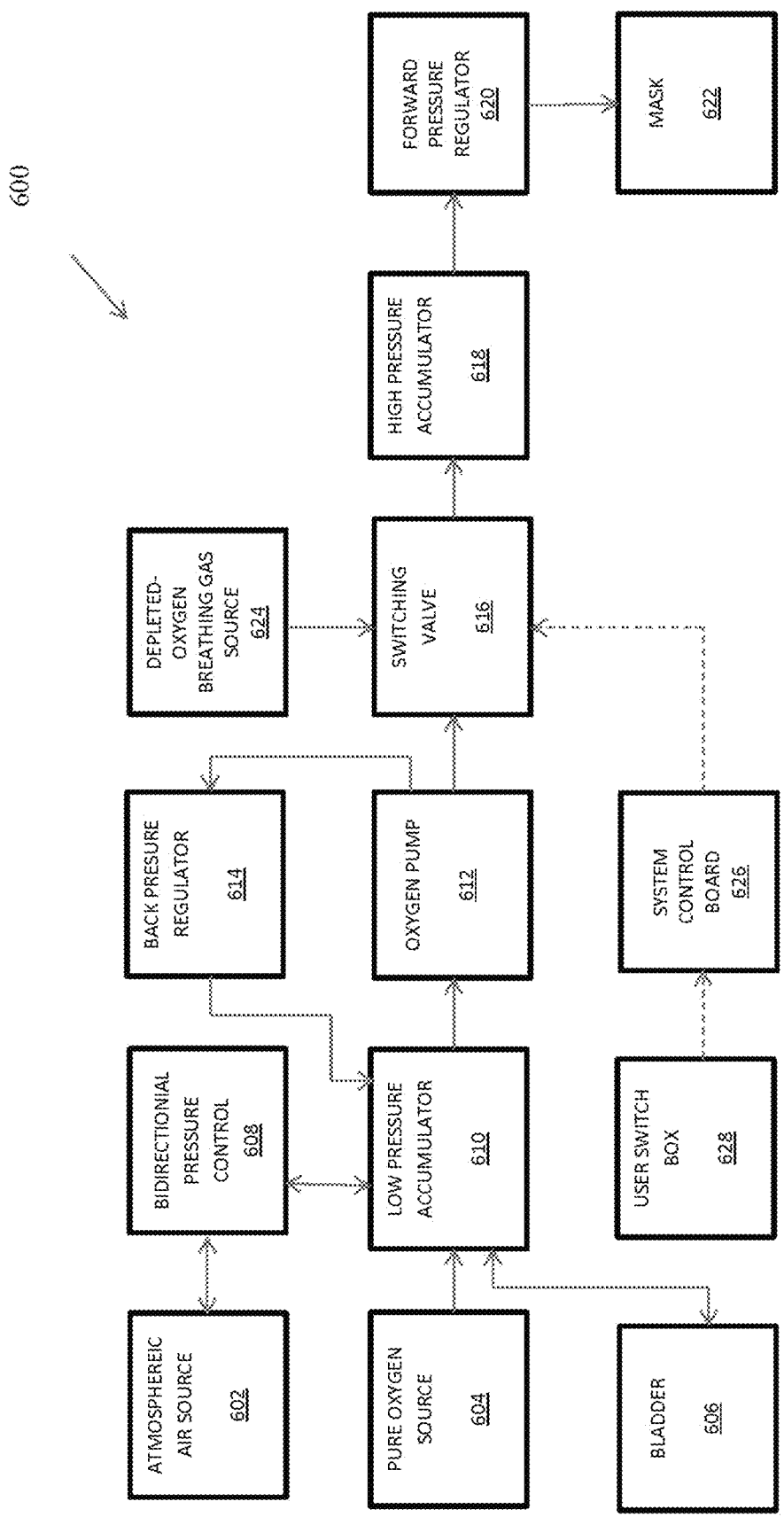
FIG. 24 is a flowchart that shows a hypoxia training device that is disposed to provide oxygen recovery modes.

FIG. 24 shows hypoxia training device 600. The physical components associated with oxygen recovery modes in the hypoxia training device 600 are sources of breathable gas, including, e.g., reduced-oxygen air and enriched-oxygen air: an atmospheric air source 602, a pure oxygen source 604, and an optional bladder containing oxygen 606, e.g., a Douglas bag used for supplemental oxygen storage. The atmospheric air source 602 is coupled to a bidirectional pressure control 608, which is coupled to another supplemental oxygen reservoir, low-pressure accumulator 610. The pure oxygen source 604 and the optional bladder 606 are also coupled to the low-pressure accumulator 610. These components are configured to allow breathable gas to flow from the sources of breathable gas through the low pressure accumulator 610, an oxygen pump 612 (with a back pressure regulator 614 coupled to the oxygen pump 612 to vent excess gas into the low-pressure accumulator 610), a switching valve 616, a high pressure accumulator 618, a forward pressure regulator 620, and to a mask 622 coupled to the hypoxia training device 600. The switching valve 616 is coupled to a depleted-oxygen breathing gas source 624 such as an EOS device and may be controlled from a system control board 626, to which a user switch box 628 may be coupled.

The pure oxygen source 604 may be the alternate outlet of an EOS device, which produces oxygen during its operation, or it may be some other source of oxygen. The atmospheric air source 602 may be used to dilute the oxygen from the pure oxygen source 604 to a mixture with higher oxygen content than atmospheric air or to supplement the pure oxygen source and the optional bladder 606 if they cannot meet the demand for oxygen required by a user. The bidirectional valve 608 may be set to allow atmospheric air to enter the system or to vent excess pressure in the system, which may build up during a period of low breathing by a user. The optional bladder 606 may be used to store oxygen during operation of an EOS, or it may be used to store oxygen from another source or sources. Oxygen from the optional bladder 606 may be used to supplement oxygen from the pure oxygen source 604 to allow for 100% oxygen recovery. Low pressure accumulator 610 is required when the optional bladder 606 is not connected to the system. Low pressure accumulator 610 is smaller (on the order of 0.5 liters) and accumulates oxygen generated by the pure oxygen source 604 only in between breaths by the user, thus it need not be very large and may be packaged within the system. Without low pressure accumulator 610, oxygen from pure oxygen source 604, which is generated continuously, would be vented to atmosphere and lost during exhale. The optional bladder 606, is larger (on the order of 60 liters) and stores large amounts of concentrated oxygen making a continuous flow to the user possible for several minutes. Due to the large size of the optional bladder, it is better suited to be mounted external to the device as an accessory.

Additionally, the effective delivery of concentrated oxygen above 35% requires the use of a supplementary oxygen reservoir, optional bladder 606 This optional bladder 606 would need to be filled before use of the hypoxia training device 600 to ensure delivery of concentrated oxygen gas to the user, so that the oxygen recovery modes would be available when needed. To provide breathable gas with the desired oxygen concentration in an oxygen recovery mode, the amount of gas in optional bladder 606, the concentration of oxygen in optional bladder 606, and the amount of breathable gas consumed by the user must be known. A low pressure transducer may be used to detect the amount of gas in optional bladder 606, and an oxygen sensor may be used to measure the average concentration of oxygen in optional bladder 606. (The relatively poor response time of oxygen sensors prevents the reliable use of closed-loop feedback for controlling concentration.)

Before filling the oxygen reservoir, it should be fully evacuated to ensure no dilution by gases already present. This evacuation may be accomplished by operation of an oxygen delivery pump (e.g., PDP-105, FIG. 2D), which would vent present gases through the forward pressure regulator 620 (e.g., FPR-101, FIG. 2E).

If pure oxygen is desired for optional bladder 606, it may be obtained from the EOS device or some other source of pure oxygen and optional bladder 606 may be filled from the selected source. If a lower concentration of oxygen is desired, optional bladder 606 may be simultaneously filled from a pure oxygen source such as the pure oxygen source 604 and from a source of atmospheric air such as the atmospheric air source 602. An exemplary pure oxygen flow rate, along with exemplary desired oxygen concentrations, required air flows, optional bladder 606 volumes, and optional bladder 606 fill times are given in Table 5 below.

TABLE 5 exemplary pure oxygen flow rate, desired oxygen concentrations, required air flows, optional bladder volumes, and optional bladder fill times:

| Pure oxygen production rate (SLPM) | Desired oxygen concentration | Require air flow (SLPM) | Optional bladder volume (L) | Optional bladder fill time (min) |
| --- | --- | --- | --- | --- |
| 5 | 40% | 15.7 | 60 | 2.9 |
| 5 | 50% | 8.6 | 60 | 4.4 |
| 5 | 60% | 5.1 | 60 | 5.9 |
| 5 | 70% | 3.0 | 60 | 7.5 |
| 5 | 80% | 1.7 | 60 | 9.0 |
| 5 | 90% | 0.7 | 60 | 10.5 |
| 5 | 100% | 0.0 | 60 | 12.0 |

The required air flow may be calculated with Equation 3:

Air flow=(oxygen rate)(1−oxygen concentration)/(oxygen concentration−21%)

If an EOS device is used to fill optional bladder 606, the oxygen produced by the EOS device must be vented during provision of oxygen-depleted breathable gas without affecting the oxygen concentration in optional bladder 606. This may be accomplished with a controllable exhaust valve placed before SV-106. During provision of oxygen-depleted breathable gas, closing SV-106 isolates optional bladder 606 from the EOS's oxygen stream, while opening the exhaust valve vents the oxygen from the EOS.

The low-pressure accumulator 610 includes one or more flexible-walled containers that provide low-pressure storage of oxygen so that the hypoxia training device 600 can tolerate the peak flow of each breath. The oxygen pump 612 maintains the output pressure required by the hypoxia training device 600. The oxygen pump 612 may be controlled to reduce power consumption. The back-pressure regulator 614 may be used to prevent over-pressurizing the outlet while reducing oxygen waste. When the oxygen pump 612 is enabled and the oxygen it supplies exceeds that which is breathed by the user, the excess oxygen may be fed back to the low-pressure accumulator 610, preventing drawing of oxygen from the pure oxygen source 604 or the bladder 604 and venting it out of the hypoxia training device 600.

The switching valve 616 enables a user or an operator such as a trainer to switch between the depleted-oxygen breathing gas source 624 and the oxygen pump 612 that supplies oxygen to the user in oxygen recovery mode. The user switch box 628 or the system control board 626 may be used to switch the switching valve 616.

The high-pressure accumulator 618, along with the low-pressure accumulator 610, may serve to sustain the user's breathing at the mask 622 by supporting peak flow rates. Because the high-pressure accumulator 618 serves both the reduced-oxygen breathable gas pathway and the oxygen recovery pathway, it creates a delay when the breathing gas sources are switched at the switching valve 616. Breathing gas supplied after a switch will take time to dilute through the high-pressure accumulator 618 before the user is breathing the breathable gas to which the hypoxia training device 600 has been switched.

The high-pressure accumulator 618 supplies breathable gas to the forward pressure regulator 620. The forward pressure regulator 620, which may be an electronic forward pressure regulator, operates in the oxygen recovery mode as it does in the supply of oxygen depleted breathable gas to the user.

There are two types of pressure reducing regulator, dual stage and single stage regulators. Either type may be used with the present invention. A dual stage regulator reduces inlet pressure in two stages, whereas a single stage regulator reduces it in one stage. Dual stage regulators are able to deliver a near-constant pressure at the outlet, even with decreasing pressure, whereas single stage regulators increase outlet pressure with decreasing pressure. Both types of regulator may be adapted to the present invention by using an appropriately sized accumulator and gas compressor; the larger the accumulator, the smaller the pressure fluctuations in the system and out of the regulator, and the higher the flow rate produced by the gas compressor, the smaller the pressure fluctuation.

The mask 622 may be a mask designed to military specifications or one designed to commercial specifications, such as a mask from GENTEX®, Rockwell-Collins's SWEEP-ON® 2000 mask, or some other commercial mask.

Typically, military masks operate to provide breathable gas to the user at about 1.5 inches H2O at a positive pressure, so that the breathable gas flows into the mask without the user inhaling. Typically, commercial masks operate to provide breathable gas to the user at about 3.0 inches H2O but at negative pressure, requiring the user to inhale to draw breathable gas into the mask.

Further, commercial masks typically operate in three modes: (1) "normal"; (2) "100%"; and (3) "emergency." The present invention cannot be used with a commercial mask in normal mode because in normal mode, the breathable gas supplied to the mask is diluted with air. However, the present invention may be used with a commercial mask in "100%" mode or in emergency mode. Both modes are oxygen recovery modes. In the 100% mode, pure oxygen is supplied to the mask at a negative pressure. In the emergency mode, pure oxygen is delivered to the mask at a positive pressure. Embodiments of the present invention fulfill the requirements of the "100%" mode and the emergency mode. The hypoxia training device 600 may be configured to deliver either oxygen-depleted air or concentrated oxygen to a commercial mask when set to either 100% or emergency mode while maintaining the predefined pressure given by the mask in either mode.

A commercial mask such as the SWEEP-ON® 2000 mask requires the hypoxia training device 600 to operate at 60-90 psi. FIG. 26C illustrates how the hypoxia training device 600 may be configured to supply a commercial mask such as the SWEEP-ON® 2000. To achieve this pressure range, the hypoxia training device 600 may include a booster pump 630, a high-pressure accumulator 618, and a water knock out (WKO) 631 (a fluidic device or volume that allows condensed water to drop out of humidified gases; the exiting gas will be at a lower humidity ratio and, therefore, carry less water vapor) in addition to the components already described. In FIG. 26C, mask 622 is a commercial mask. Gas compressor 630 may be a booster pump. Further, to use the hypoxia training device 600 with a typical commercial mask, the forward pressure regulator 620 may be bypassed with a hose connection just upstream of the forward pressure regulator 620, with a hose coupled to the hose connection and the mask. The commercial mask may provide the pressure control that is otherwise provided by the forward pressure regulator 620.

A commercial mask may also be simulated with a military mask or a simpler mask with low pressure intake and exhaust check valves. The negative pressure required by a commercial mask in "100%" mode may be provided by a forward pressure regulator 620 set to a negative pressure bias. Such a selection of negative pressure bias may be made via software and an electronic selector switch for the user or another person such as a trainer to switch the forward pressure regulator 620 to simulated commercial "100%" mode, requiring a negative pressure at the mask, or a simulated commercial emergency mode, requiring a positive pressure at the mask.

The present invention may generally be used with continuous flow masks, pressure-on-demand masks, and diluter demand masks. A continuous flow mask includes inhalation and exhalation check valves, an orifice, a tube connection to the breathable gas delivery system, and a gas bag. The flow rates through a continuous flow mask are a function of the orifice flow area and upstream pressure. To use such a continuous flow mask with the present invention, the mask's inhalation check valve may be removed to prevent ambient air from mixing with breathable gas coming into the system. Because the pressure to the inlet of the orifice will need to be approximately 60-70 psig, a forward pressure regulator is not required; however, a larger pump or compressor compared to the pump or compressor used for lower system pressures would be required. Further, the accumulator must be sized appropriately to ensure that pressure to the inlet of the orifice is maintained, since the pressure proportionately affects the flow rate to the mask. The orifice flow area must also be sized appropriately to ensure that enough flow goes to the mask to prevent air starvation of the user.

The present invention may also be used with a diluter demand mask. A diluter demand mask functions like a pressure on demand mask except that the diluter demand mask has a diluter valve assembly that connects the mask interior to the ambient atmosphere. To use such a diluter demand mask with the present invention, the diluter demand valve may be manually shut off by a user so that it behaves like a pressure on demand mask.

The present invention may be used with types of oxygen separation devices besides electrochemical oxygen separation (EOS) devices to serve as, e.g., the pure oxygen source 604. This feature of the present invention offers a large degree of flexibility in integrating the invention with various flight simulators and other training environments, because the oxygen separation device may be selected to suit various circumstances and limitations. The present invention may be used with a number of oxygen separation devices besides EOS devices, including a pressure swing adsorption device, a vacuum pressure swing adsorption device, oxygen separation polymer membranes, a solid inorganic oxide ceramic membrane, an ion transport membrane, a cryogenic device that produces oxygen, or a MOLTOX™ chemical oxygen separator.

Figure 25:
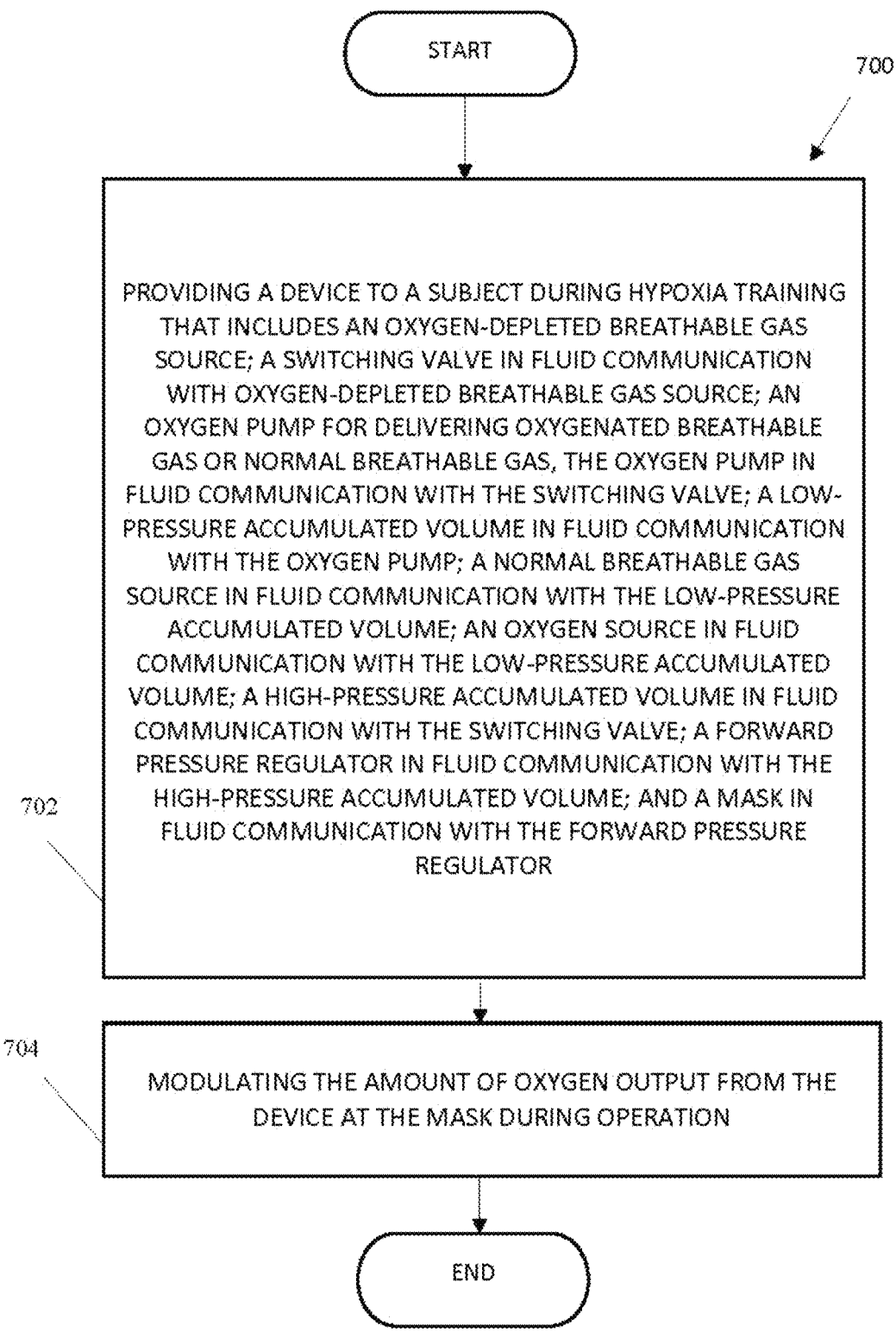
FIG. 25 depicts a flowchart of a method of controlling the level of oxygen in a breathable gas stream during hypoxia training.

FIG. 25 illustrates a method embodiment of the present invention. Method 700, a method of controlling the level of oxygen in a breathable gas stream during hypoxia training includes, in block 705, the step of providing a device to a subject during hypoxia training that includes an oxygen-depleted breathable gas source; a switching valve in fluid communication with oxygen-depleted breathable gas source; an oxygen pump for delivering oxygenated breathable gas or normal breathable gas, the oxygen pump in fluid communication with the switching valve; a low-pressure accumulated volume in fluid communication with the oxygen pump; a normal breathable gas source in fluid communication with the low-pressure accumulated volume; a bladder in fluid communication with the low-pressure accumulated volume; a high-pressure accumulated volume in fluid communication with the switching valve; a forward pressure regulator in fluid communication with the high-pressure accumulated volume; and a mask in fluid communication with the forward pressure regulator; and modulating the amount of oxygen output from the device at the mask during operation. Method 700 also includes modulating the amount of oxygen output from the device at the mask during operation in block 705.

Figure 26A:
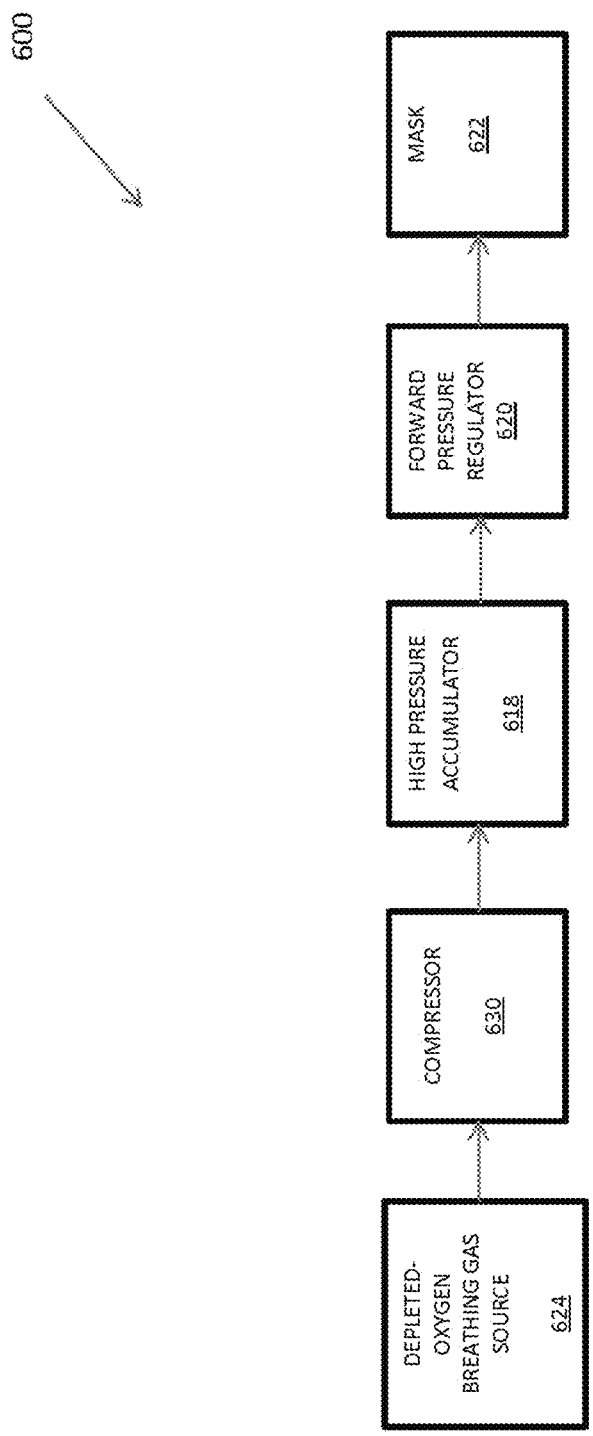
FIGS. 26A, 26B, and 26C are flowcharts that show a hypoxia training device that is disposed to provide pressure on demand.
Figure 26B:
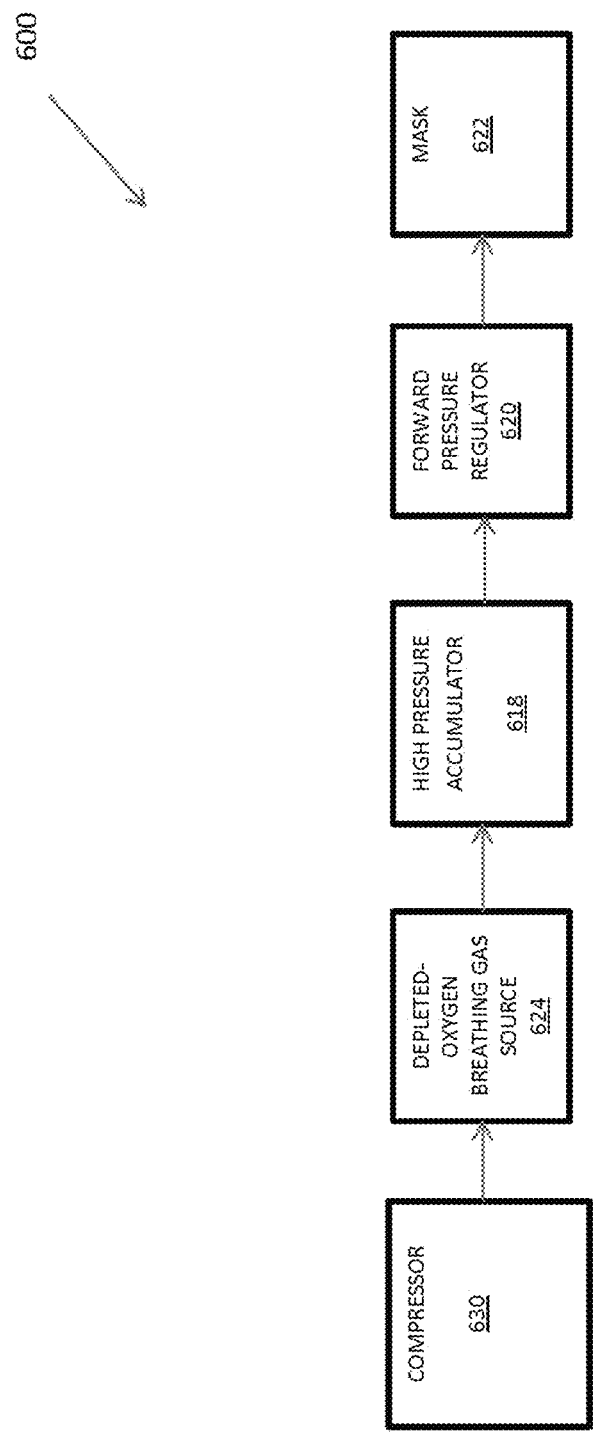
Figure 26C:
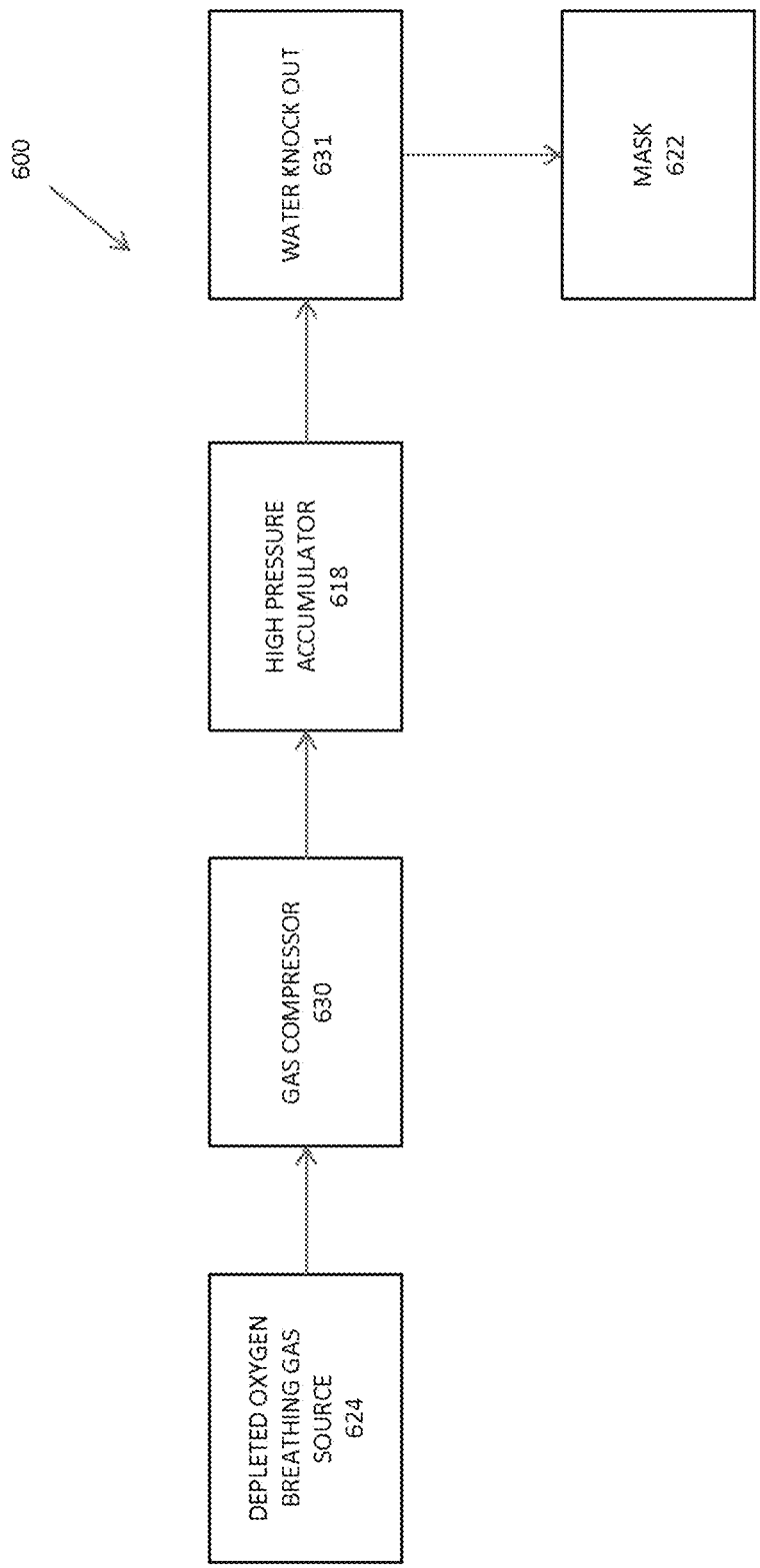

As shown in FIGS. 26A and 26B, to provide pressure on demand, the hypoxia training device 600 requires a gas compressor 630, a high pressure accumulator 618, and a forward pressure regulator 620. The gas compressor 630 is required to provide and maintain sufficient inlet pressure to allow the forward pressure regulator 620 to open. As the forward pressure regulator 620 opens to permit flow, the system pressure starts to fall. An accumulator 618 is required to maintain the upstream pressure above the minimum pressure required by the forward pressure regulator 620 to open. There is an inverse relationship between the accumulator size and the pressure maintained in the system, and the hypoxia training device 600 may be operated over a wide variety of pressures and accumulator volumes.

If the average flow rate provided by the gas compressor 630 is lower than the average flow rate of gas consumed at the outlet, the system pressure drops over subsequent venting periods. Eventually, the pressure would drop below the minimum pressure required to operate the forward pressure regulator 620. The maximum operable pressures would be limited by the rated pressure of the components of the system, while the accumulator size would be limited by the space available. Metallic tubing, fittings, and components would allow higher pressure but would increase cost and weight. Hence, any air separation system that removes oxygen from air can be used with the present invention to provide pressure on demand as long as a system design including a gas compressor 630, an accumulator 618, and a forward pressure regulator 620 have been sized appropriately.

The components within hypoxia training device 600 required for use with an oxygen separation system may be configured so that the gas compressor 620 provides breathable gas to the oxygen separation system, or so that the oxygen separation system provides oxygen deprived breathable gas to the gas compressor 630. Either of those two configurations may then provide breathable gas to the accumulator 618, from which it flows to the forward pressure regulator 620 and then the mask 622 coupled to the hypoxia training device 600, as shown in FIGS. 26A and 26B, respectively.

FIG. 26C illustrates an exemplary configuration similar to the configurations shown in FIGS. 26A and 26B, to be used with a commercial mask. FIG. 26C illustrates how the hypoxia training device 600 may be configured to supply a commercial mask such as the SWEEP-ON® 2000. To achieve this pressure range, the hypoxia training device 600 may include a booster pump 630, a high-pressure accumulator 618, and a water knock out (WKO) 631 (a fluidic device or volume that allows condensed water to drop out of humidified gases; the exiting gas will be at a lower humidity ratio and, therefore, carry less water vapor) in addition to the components already described. Here, mask 622 is a commercial mask. Gas compressor 630 may be a booster pump.

In some embodiments of the present invention, the configuration shown in FIGS. 26A, 26B, and 26C would be coupled to switching valve 616 and placed where high pressure accumulator 618, forward pressure regulator 620, and mask 622 appear in FIG. 24.

Figure 27A:
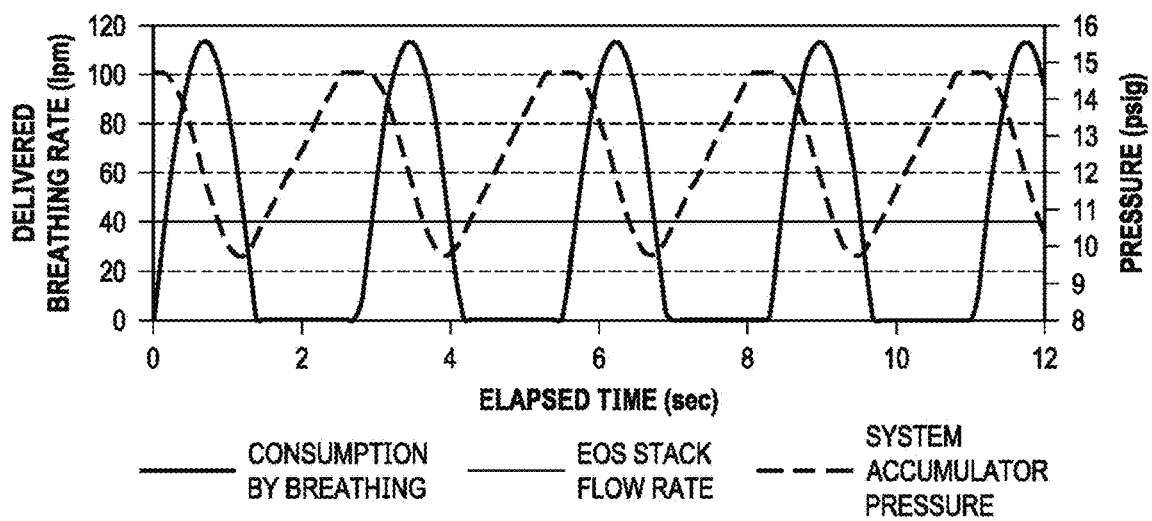
FIGS. 27A, 27B, and 27C shows graphs that depict exemplary data for delivered rate for consumption by a user's breathing, EOS stack flow and pressure, and system accumulator pressure.
Figure 27B:
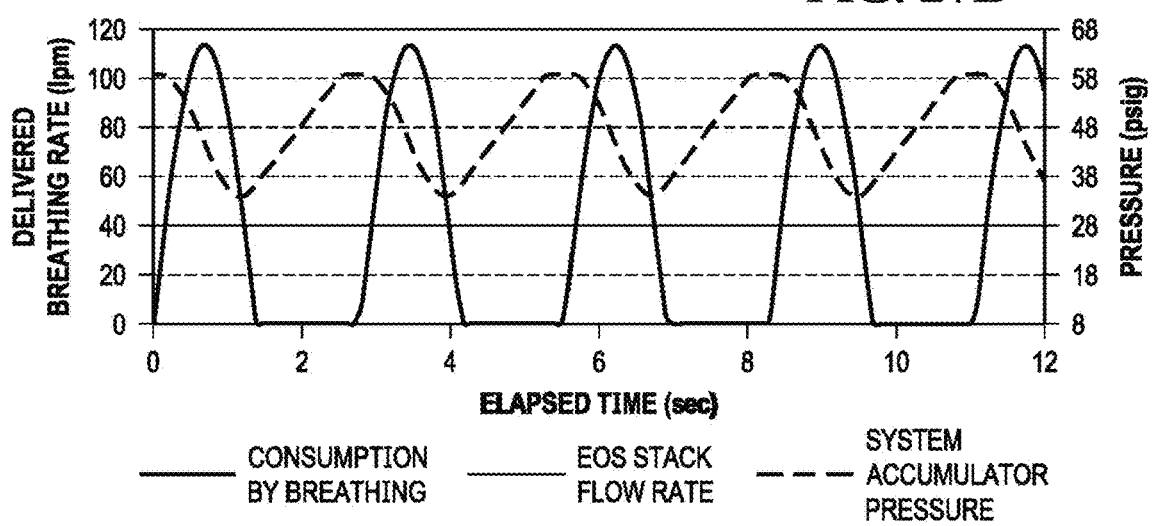
Figure 27C:
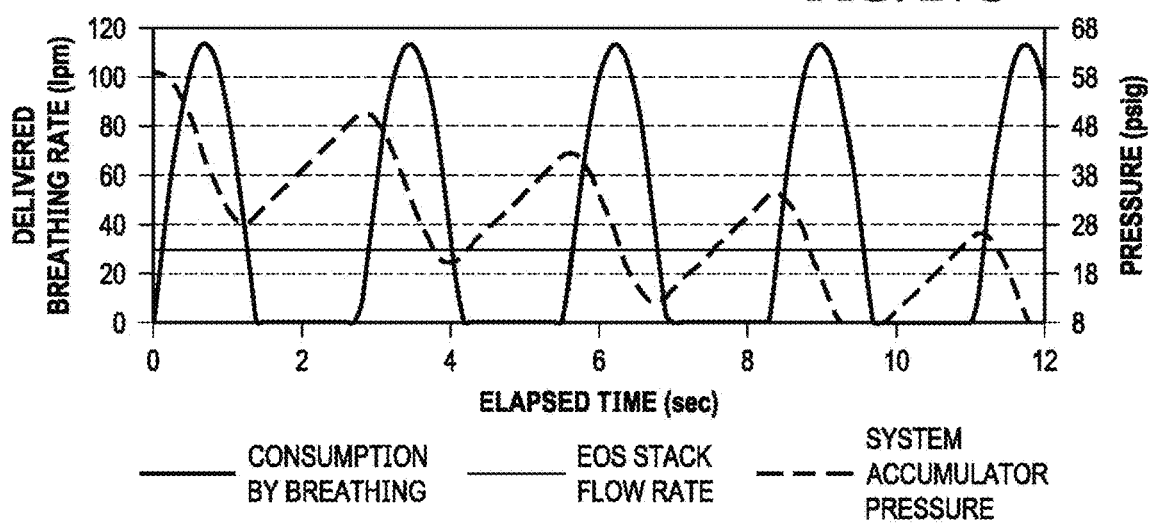

FIGS. 27A, 27B, and 27C depict exemplary data for delivered rate (lpm) for consumption by a user's breathing and EOS stack flow and pressure (psig) and for system accumulator pressure (psig). FIG. 27A depicts those quantities for a 2.5 L accumulator, for 36 splm consumption at the outlet and 40 slpm produced by the pump, and a maximum system pressure of 2 atm. FIG. 27B depicts those quantities for a 0.5 L accumulator, for 36 splm consumption at the outlet and 40 slpm produced by the pump, and a maximum system pressure of 5 atm. FIG. 27C depicts those quantities for a 2.5 L accumulator, for 36 splm consumption at the outlet and 30 slpm produced by the pump, and a maximum system pressure of 5 atm.

Figure 28A:
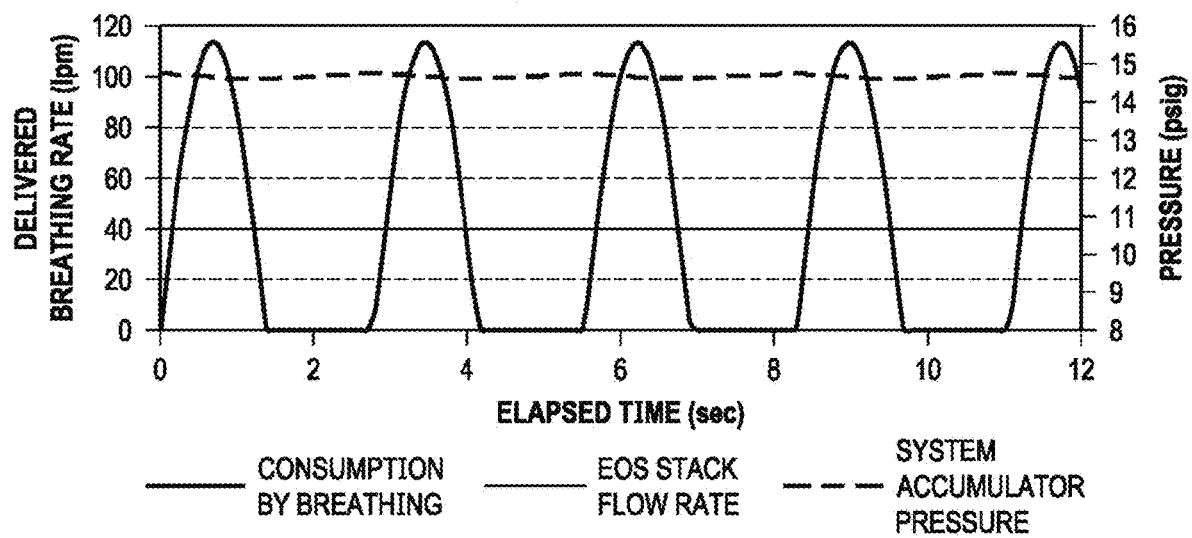
FIGS. 28A and 28B show graphs of exemplary data for breathable gas consumption by breathing, reduced-oxygen breathing gas source flow rate, and a system accumulator pressure.
Figure 28B:
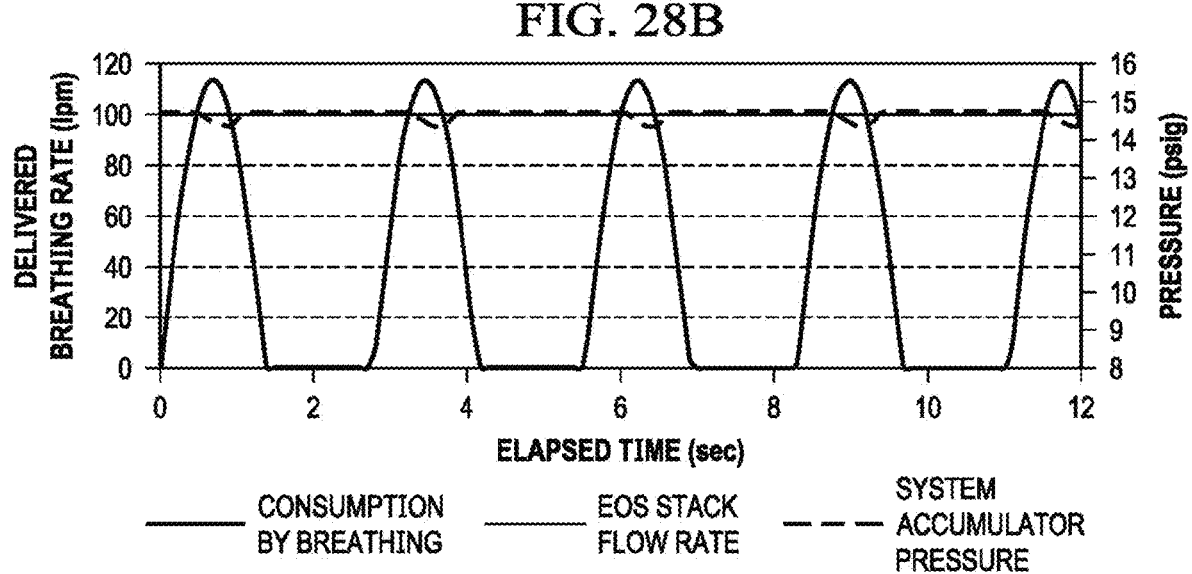

FIGS. 28A and 28B show graphs of exemplary data for breathable gas consumption by breathing, reduced-oxygen breathing gas source flow rate (here an EOS stack flow rate), and a system accumulator pressure over a period of several breaths. FIG. 28A shows those values with a 100 L accumulator and a compressor producing 40 slpm. FIG. 28B shows those values with a 2.5 L accumulator and a compressor producing 100 slpm.

Figure 29:
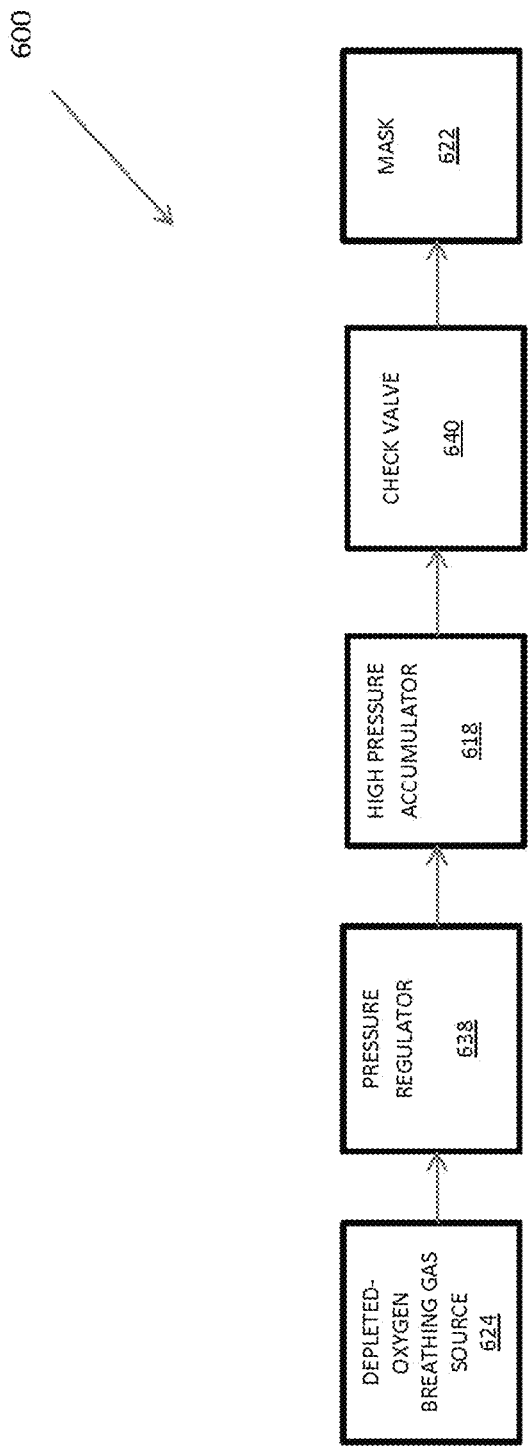
FIG. 29 shows a flowchart of an alternative configuration of a hypoxia training device.

FIG. 29 shows an alternative configuration of hypoxia training device 600. Reduced-oxygen breathing gas source 624 supplies breathable gas to a pressure regulator 638, which reduces the gas pressure and supplies the gas to an appropriately-sized high-volume accumulator 618. A check valve 640 may be used between the high-volume accumulator 618 and the mask 622. The cracking pressure of the check valve must be small enough that it opens when a user breathes through the mask 622 but large enough to keep the gas from venting constantly. Because the pressure at which the gas is stored is relatively small, the high-volume accumulator 618 needs to be large enough to provide the required flow rate to the user.

An embodiment of the present invention incorporates mask-state detection: the detection of whether a user of the present invention is using the mask 622 coupled to the hypoxia training device 600. Mask-state detection is used to set the breathable gas pressure supplied by the system appropriately for various use scenarios and for non-use while the system is operating. The mask-state detection capability of the present invention can distinguish between shallow breaths or slow breathing and removal of the mask 622. Mask-state detection in the present invention may use the monitoring of various parameters of the user's breathing to inform detection of the mask state, including breathable gas flow rate, change in breathable gas flow rate, breathable gas outlet pressure, and change in breathable gas outlet pressure. Mask-state detection may be used with both military and commercial masks. Commercial masks would require the inclusion of a pressure transducer to measure the pressure at the mask. The exact system placement of the transducer would have to be tested before being finally determined. The set points of the various criteria would also have to be calibrated for the different setup. However, the overall approach for military and commercial masks is the same.

In an embodiment of the invention, the mask 622 coupled to the hypoxia training device 600 is presumed to be in a mask-off state, i.e., not worn by a user. The forward pressure regulator is set to maintain a low, non-zero pressure, e.g., approximately 0.075 inches $H_2O$, which provides a small constant flow of breathable gas, e.g., approximately 5-12 slpm to the mask 622. The hypoxia training device 600 monitors a set of criteria to determine if a user has donned the mask 622. The criteria are checked periodically, e.g., several times per second. If the criteria for the mask-on state are met, the hypoxia training device 600 switches to monitoring criteria to determine if the user has taken the mask off. Otherwise, the hypoxia training device 600 continues to monitor for the mask-off state.

If a mask-on state has been determined, after a short period of time of preselected length, the forward pressure regulator 620 is set to deliver to the mask 622 a breathing gas pressure for use during training, e.g., approximately 1.5 $H_2O$. The short period of time prevents an unintentional switch to the mask-on pressure. While in the mask-on state, the hypoxia training device 600 monitors one or more of the relevant parameters to determine if the user has taken off the mask 622. The criteria must be sufficient to distinguish between a mask removal and a long, deep inhalation. If a mask removal is determined, the forward pressure regulator 620 is set to deliver breathable gas to the mask 622 at the low mask-off pressure, e.g., 0.075 inches $H_2O$. Again, a short period of time between the determination of a mask-off state and the switch to mask-of pressure prevents an inadvertent switch. Otherwise, when the forward pressure regulator 620 is set to the lower pressure, a sudden short increase in outlet pressure would be interpreted as the user putting the mask 622 on again. After switching to the mask-off state, the hypoxia training device 600 now begins to monitor for a mask-on state.

Figure 30:
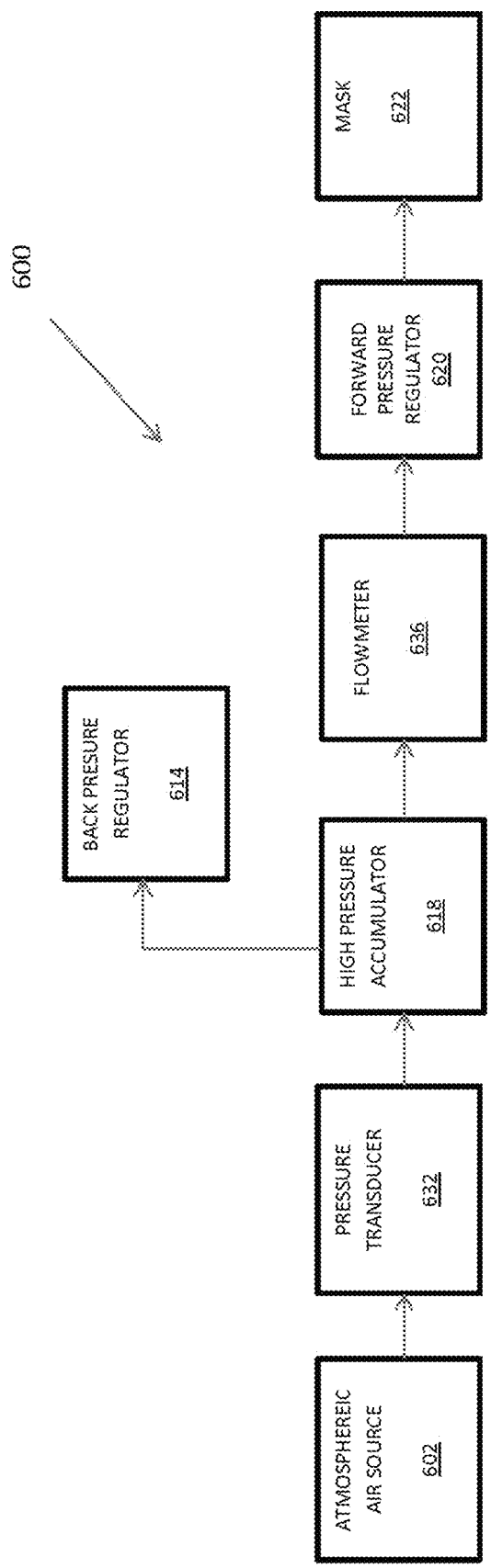
FIG. 30 shows a flowchart of the components associated with the mask-state determination within a hypoxia training device.

As shown in FIG. 30, the components associated with the mask-state determination within hypoxia training device 600 include an breathable gas source, e.g., either atmospheric air source 602 or pure oxygen source 604, a pressure transducer 632, a high-pressure accumulator 618, a back-pressure regulator 634, a flowmeter 636, a forward pressure regulator 620, and a mask 622 coupled to the hypoxia training device 600, all of which are in fluid communication with each other. These components are typically coupled so that breathable gas flows from the breathable gas source through the pressure transducer 632, the high-volume accumulator 618 (with the back-pressure regulator 634 coupled to the high-volume accumulator 618 so that breathable gas can be vented from the high-volume accumulator 618 through the back-pressure regulator 634), the flowmeter 636, and the forward pressure regulator 620 to the mask 622.

The breathable gas source may be a source of oxygen-enriched breathable gas, e.g., pure oxygen source 604, or oxygen-reduced breathable gas, e.g., oxygen-reduced breathable gas source 624. Further, the breathable gas source may be an EOS device or some other source of breathable gas, as long as it is capable of providing sufficient pressure, e.g., at least approximately 15 psi, as measured at the pressure transducer 632. Variations in this pressure could affect the ability of the hypoxia training device 600 to determine the mask state.

The high-pressure accumulator 618 includes one or more hard-wall containers that store air to compensate for high demand at the mask, such as a deep breath by the user. The sizes of these containers affect the rate of change in the outward flow when the mask is removed or when the user takes a deep breath. Similarly, the connections and tubing of the hypoxia training device 600 act as breathable gas storage as well, and the amount of breathable gas present in them further affects the rate of change of outward flow and the period of time during which the user may inhale maximum flow.

The back pressure regulator 634, which is in fluid communication with the high-pressure accumulator 618, regulates and maintains the maximum pressure in the hypoxia training device 600 by venting breathable gas once a preselected maximum pressure, e.g., at least approximately 15 psi, is reached. It does not vent breathable gas when the breathable gas pressure is below the preselected maximum pressure.

The flowmeter 636 measures the flow of breathable gas from the high-pressure accumulator to the forward pressure regulator 620 and then to the mask 622. The flowmeter 636 does not measure flow out of the back-pressure regulator 634. Thus, the flowmeter 636 allows the hypoxia training device 600 to track the user's breathing waveform, measuring a flow toward the mask 622 when the user inhales and no flow when the user exhales or stops breathing.

The forward pressure regulator 620, which may be an electronic forward pressure regulator, controls and monitors the breathable gas pressure experienced at the mask 622. The forward pressure regulator 620 monitors the parameters that enable the hypoxia training device 600 to detect the mask state, and the pressure supplied to the mask 622 is changed at the forward pressure regulator 620 in response to the determination of the mask state.

The mask 622 is coupled to the hypoxia training device 600 at the forward pressure regulator 620, e.g., by a length of flexible tubing that can be pinched or stretched to alter slightly flow conditions to the mask 622.

Mask-state determination relies on the monitoring of one or more parameters, including the breathable gas flow rate, the change in breathable gas flow rate, the outlet pressure, and the change in outlet pressure. Each parameter monitored is sampled periodically, e.g., several times a second. If the parameters meet their respective preselected criteria a preselected number of times, the hypoxia training device 600 makes the appropriate determination of the mask state. The number of times that the criteria must be met is preselected in part to reduce or eliminate the effect of false positives on the determination of the mask state. Typical criteria for the values include, e.g., for the breathable gas flow rate, less than approximately 70 slpm for mask-off; for change in breathable gas flow rate, less than approximately 0.4 inches $H_2O$ for mask-off; for outlet pressure, less than approximately 1.5 inches $H_2O$; and for change in outlet pressure, less than 2 slpm.

Figure 31:
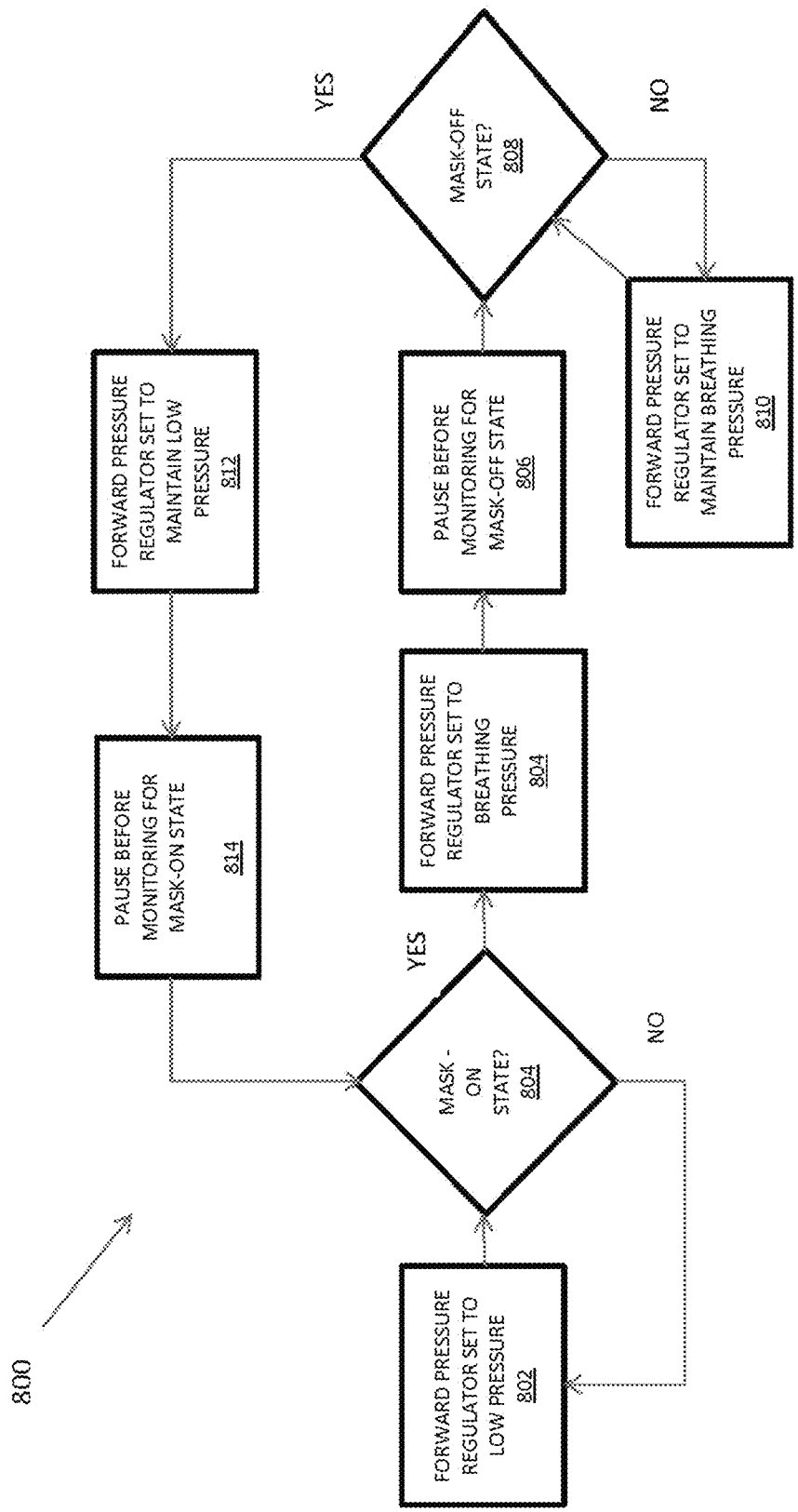
FIG. 31 shows a flowchart of a method of mask-state determination.

FIG. 31 shows a flowchart of a method of mask-state determination 800. In block 802, the forward pressure regulator 620 is set to maintain low pressure. The hypoxia training system 600 monitors the relevant criteria for a mask-on state in block 804. If a mask-on state is not detected, forward pressure regulator 620 continues to be set to maintain low pressure, as in block 802. If a mask-off state is detected forward pressure regulator 620 is set to maintain a pressure suitable for the user's breathing in block 804. In block 806, a pause is performed before monitoring for a mask-off state starts. In block 808, the hypoxia training system 600 monitors the relevant criteria for a mask-on state. If no-mask-off state is detected, the forward pressure regulator 620 continues to be set in block 810 to maintain breathing pressure and monitoring for a mask-off state continues as in block 808. If a mask-off state is detected, the forward pressure regulator 620 is set to maintain low pressure in block 812. In block 814, a pause is performed before monitoring for a mask-on state starts, as in block 804.

Figure 32:
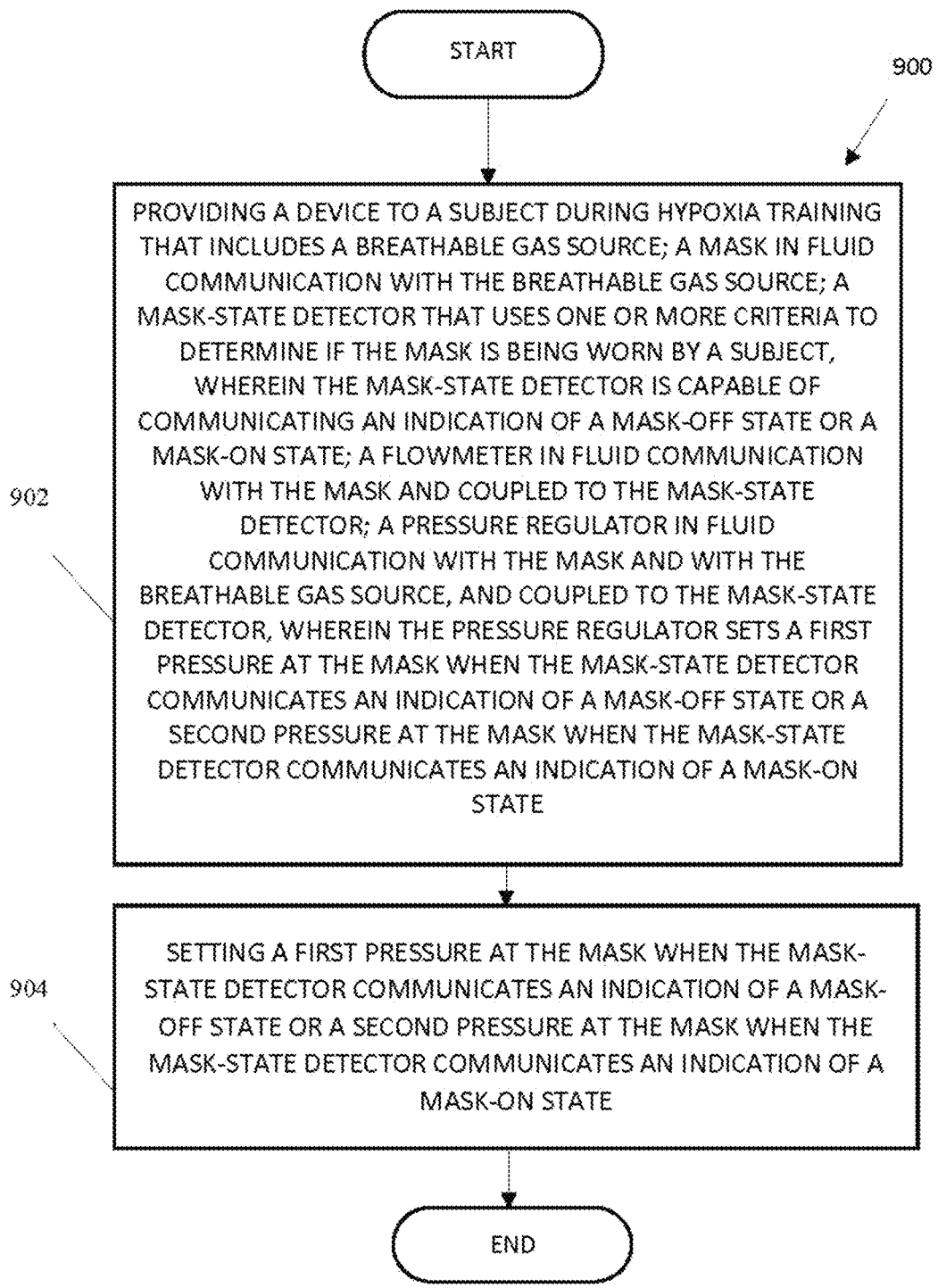
FIG. 32 shows a flowchart of a method of regulating pressure in a hypoxia training system.

FIG. 32 depicts a method embodiment of the present invention. Method 900, a method of regulating pressure in a hypoxia training system, includes in block 902 providing a device to a subject during hypoxia training that includes a breathable gas source; a mask in fluid communication with the breathable gas source; a mask-state detector that uses one or more criteria to determine if the mask is being worn by a subject, wherein the mask-state detector is capable of communicating an indication of a mask-off state or a mask-on state; a flowmeter in fluid communication with the mask and coupled to the mask-state detector; and a pressure regulator in fluid communication with the mask and with the breathable gas source, and coupled to the mask-state detector, wherein the pressure regulator sets a first pressure at the mask when the mask-state detector communicates an indication of a mask-off state or a second pressure at the mask when the mask-state detector communicates an indication of a mask-on state. Block 904 of method 900 includes setting a first pressure at the mask when the mask-state detector communicates an indication of a mask-off state or a second pressure at the mask when the mask-state detector communicates an indication of a mask-on state.

Figure 33A:
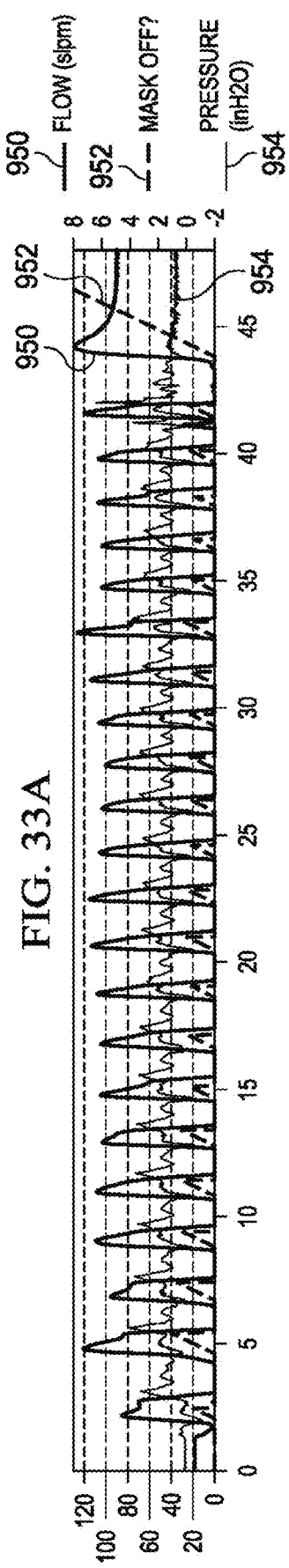
FIGS. 33A, 33B, 33C, 33D, and 33E illustrate graphs for using flow rate, change in flow rate, outlet pressure, and change in outlet pressure as the sole criteria for determining a mask state and the use of all four quantities for determining a mask state, respectively.
Figure 33B:
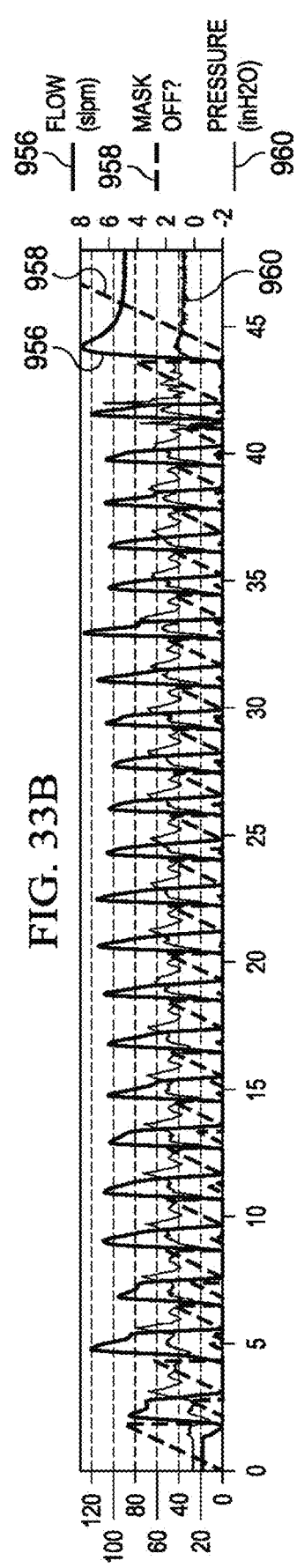
Figure 33C:
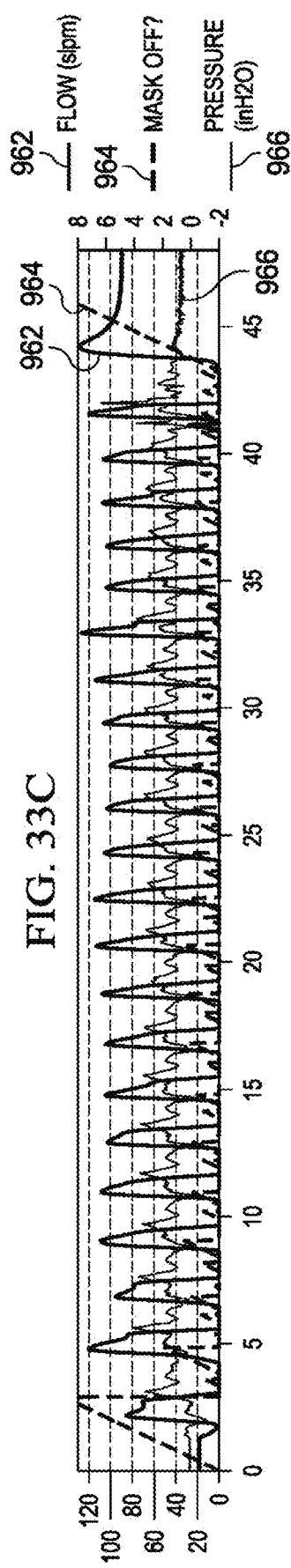
Figure 33D:
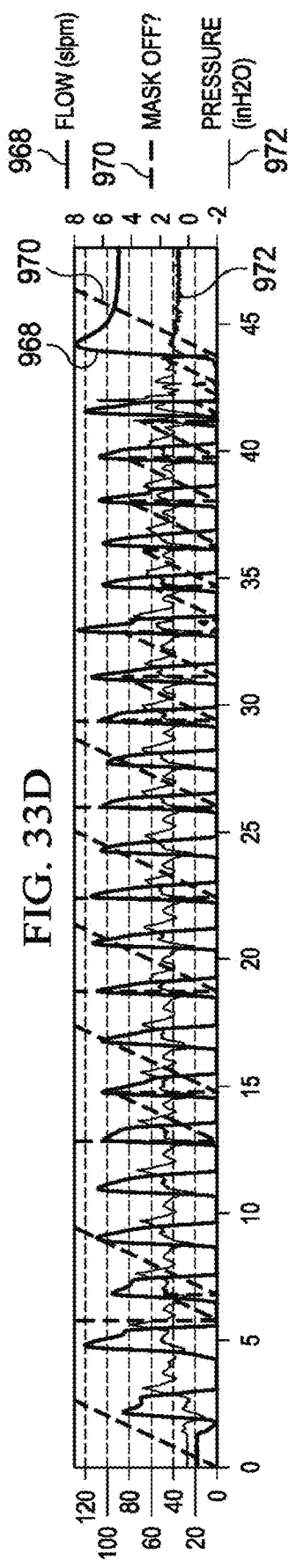
Figure 33E:
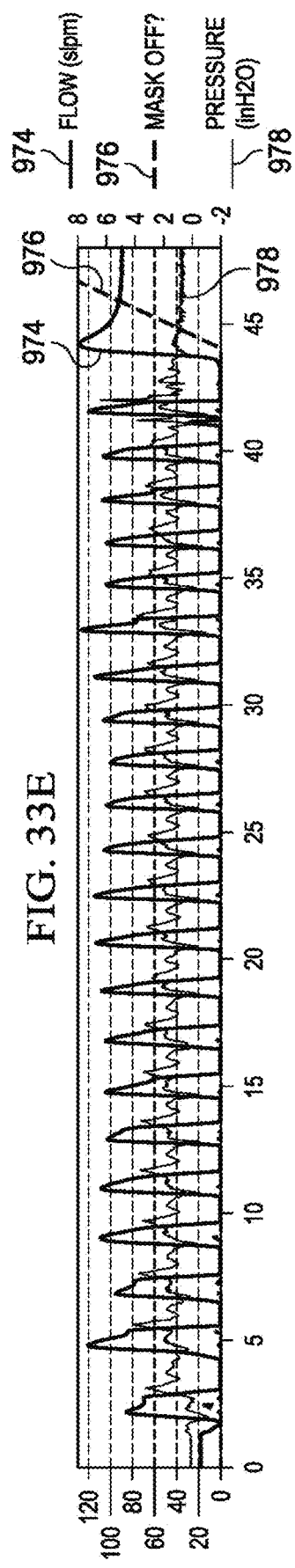

FIG. 33A shows a graph for using the flow rate as the only criterion for determining the mask state, and using a flow rate of less than 70 slpm as the criterion for the mask-off state. In the graph of FIG. 33A, trace 950 is the flow rate (slpm) (left-hand scale), trace 952 is the indication of a mask-off state, and trace 954 is the pressure (inches $H_2O$) (right-hand scale). FIG. 33B shows a graph for using the change in flow rate as the only criterion for determining the mask state, and using a change in flow rate of less than 2 slpm as the criterion for the mask-off state. In the graph of FIG. 33B, trace 956 is the flow rate (slpm) (left-hand scale), trace 958 is the indication of a mask-off state, and trace 960 is the pressure (inches $H_2O$) (right-hand scale). FIG. 33C shows a graph for using the outlet pressure as the only criterion for determining the mask state, and using an outlet pressure of less than 1.5 inches of $H_2O$ as the criterion for the mask-off state. In the graph of FIG. 33C, trace 962 is the flow rate (slpm) (left-hand scale), trace 964 is the indication of a mask-off state, and trace 966 is the pressure (inches $H_2O$) (right-hand scale). FIG. 33D shows a graph for using the change in outlet pressure as the only criterion for determining the mask state, and using a change in outlet pressure of less than 0.4 inches of $H_2O$ as the criterion for the mask-off state. In the graph of FIG. 33D, trace 968 is the flow rate (slpm) (left-hand scale), trace 970 is the indication of a mask-off state, and trace 972 is the pressure (inches $H_2O$) (right-hand scale). FIG. 33E shows a graph for using all of the criteria illustrated in FIGS. 33A-33D combined. In the graph of FIG. 33E, trace 974 is the flow rate (slpm) (left-hand scale), trace 976 is the indication of a mask-off state, and trace 978 is the pressure (inches $H_2O$) (right-hand scale). In each of the graphs, the horizontal axis represents time in seconds.

Table 6 shows exemplary experimental data for mask-off determinations for each of the foregoing criteria and for the combination of all four criteria and various numbers of samples.

TABLE 6

False positive mask-off experimental results.

| Criteria | False positives after 5 samples | False positives after 10 samples | False positives after 15 samples | False positives after 20 samples |
|---|---|---|---|---|
| Flow rate >70 slpm | 22 | 22 | 22 | 19 |
| Change in flow rate <2 slpm | 51 | 34 | 26 | 26 |
| Outlet pressure, 1.5 in. $H_2O$ | 47 | 46 | 32 | 19 |
| Change in pressure <0.4 in. $H_2O$ | 21 | 19 | 19 | 18 |
| Combined | 4 | 1 | 1 | 0 |

Figure 34:
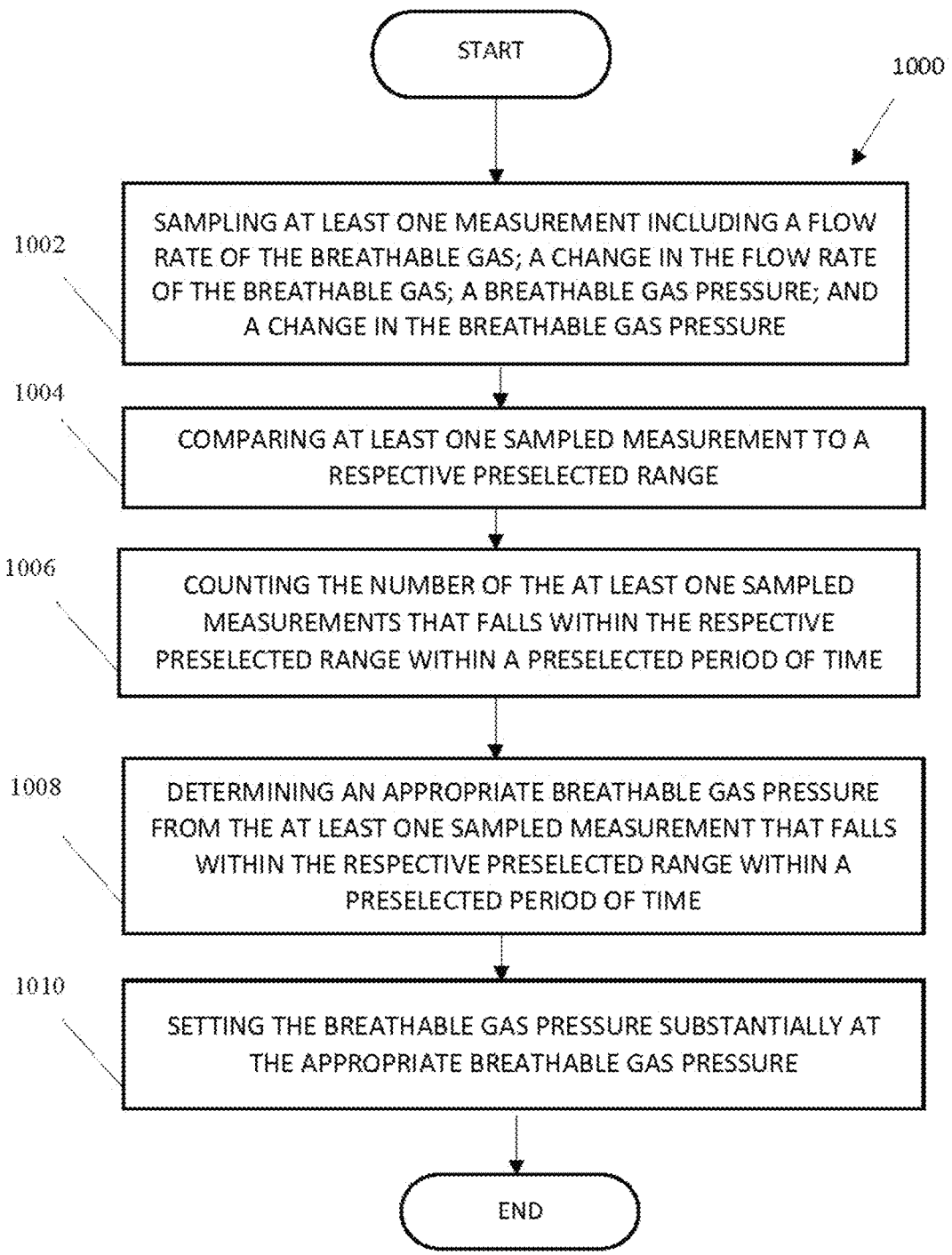
FIG. 34 shows a flowchart for a method of regulating a breathable gas pressure in a device for supplying breathable gas to a user through a mask.

FIG. 34 illustrates a method embodiment of the present invention. Method 1000, a method of regulating a breathable gas pressure in a device for supplying breathable gas to a user through a mask, includes in block 1002 sampling at least one measurement including a flow rate of the breathable gas; a change in the flow rate of the breathable gas; a breathable gas pressure; and a change in the breathable gas pressure. Method 1000 also includes comparing at least one sampled measurement to a respective preselected range in block 1004. Further, block 1006 of method 1000 includes counting the number of the at least one sampled measurements that falls within the respective preselected range within a preselected period of time. Determining an appropriate breathable gas pressure from the at least one sampled measurement that falls within the respective preselected range within a preselected period of time is included in block 1008. The breathable gas pressure is set substantially at the appropriate breathable gas pressure is included in block 1010.

The physiological effects of hypoxia are still not fully understood. As such, measuring how hypoxia affects breathing patterns is of clinical significance. Specifically, it is theorized that hypoxia affects the average breathing rate, peak inhalation rate, breaths per minute as well as the overall breathing waveform. Any data comparing breathing patterns of individuals before and after the introduction of oxygen-depleted air would be useful in better understanding these physiological effects. The present invention may monitor and store information in the user's breathing rate. An embodiment of the present invention incudes an algorithm that notes when the breathing gas flow rate rises above a small non-zero threshold number, e.g., 10 slpm, as the beginning of a breath. The algorithm notes the breathing gas flow rate for the next occurring peak value, stores the sum of the flow rate multiplied by the change in time since the last sample, and notes the next rise above the small non-zero threshold number. That next rise is considered to be the beginning of the next breath, and the time difference between successive rises above the threshold values is used to calculate breathing frequency. The length of breathing, the flow rate, and the total sum of the flow rate multiplied by time (essentially the integration of flow rate over time) are stored in an array of breathing information. The average breathing frequency for a period of a preselected number of latest breaths is also stored in the array and displayed. Breaths less than approximately one second long are dismissed, especially if they stand alone.

Figure 35:
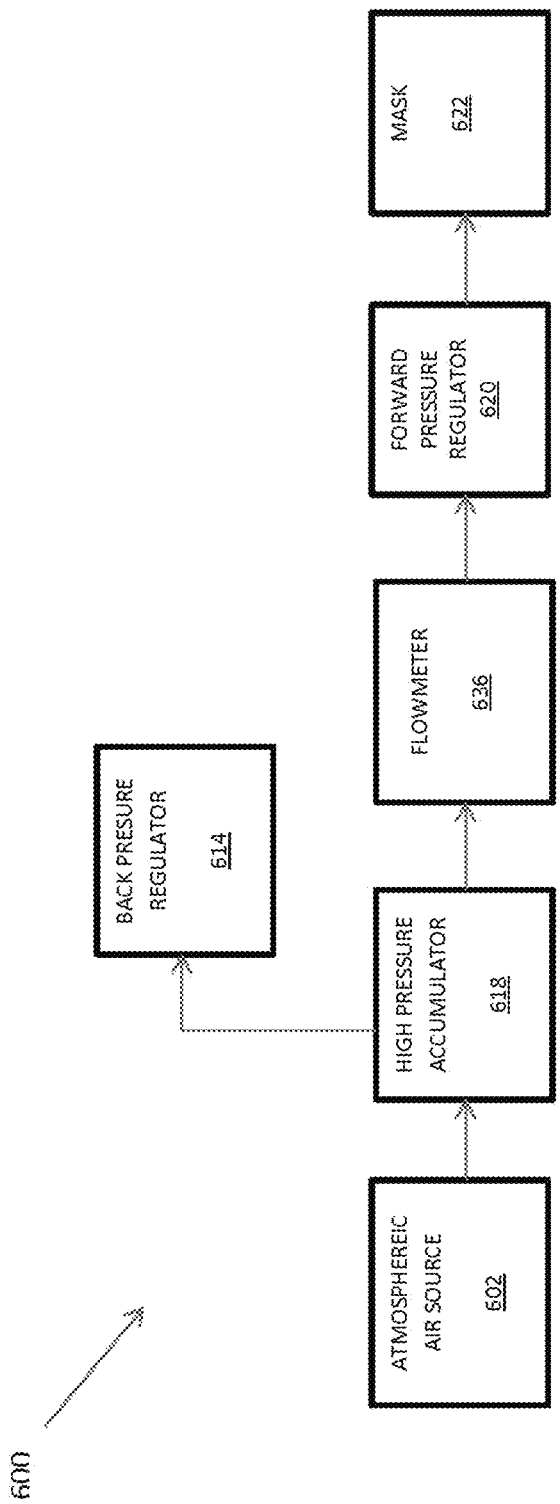
FIG. 35 shows a flowchart of the components associated with the analysis of breathing rate within a hypoxia training device.

As shown in FIG. 35, the components associated with the analysis of breathing rate within hypoxia training device 600 include the breathable gas source, e.g., either atmospheric air source 602 or pure oxygen source 604, the high-pressure accumulator 618, the back-pressure regulator 634, the flowmeter 636, the forward pressure regulator 620, and the mask 622 that is coupled to the hypoxia training device 600, all of which are in fluid communication with each other. These components are typically coupled to allow breathable gas to flow from the breathable gas source through the high-pressure accumulator 618 (with the back-pressure regulator 634 coupled to the high-volume accumulator 618 so that breathable gas can be vented from the high-volume accumulator 618 through the back-pressure regulator 634), the flowmeter 636, and the forward pressure regulator 620 to the mask 622.

The breathable gas source may be a source of oxygen-enriched breathable gas or oxygen reduced-breathable gas. Further, the breathable gas source may be an EOS device or some other source of breathable gas. The breathable gas source must be able to match the peak flow rate of a human user or to supply sufficient pressure to the high-pressure accumulator 618 to permit the high-pressure accumulator 618 to match that peak flow rate.

The back pressure regulator 634, which is in fluid communication with the high-pressure accumulator 618, regulates and maintains the maximum pressure in the hypoxia training device 600 by venting breathable gas once a preselected maximum pressure, e.g., at least approximately 15 psi, is reached. It does not vent breathable gas when the breathable gas pressure is below the preselected maximum pressure.

The flowmeter 636 is required to monitor the breathable gas flow exiting through the mask 622. Proper placement of the flowmeter 636 is essential for accurate measurements. The tubing volume and flow restrictions between the flowmeter 636 and the mask 622 can severely impact the accuracy of the analysis algorithms. If too much volume exists in the space between the mask 622 and the flowmeter 636, the dampening effect of the dead volume can alter the highest and lowest flow rates measured.

The forward pressure regulator 620, which may be an electronic forward pressure regulator, is required to control the pressure experienced by the user of the hypoxia training device 600. Further, the forward pressure regulator 620 limits flow out of the hypoxia training device 600 to enable pressure on demand delivery of breathable gas. Pressure on demand delivery of the breathable gas helps clarify the breathing waveform, emphasizing the important features of each breath.

Figure 36:
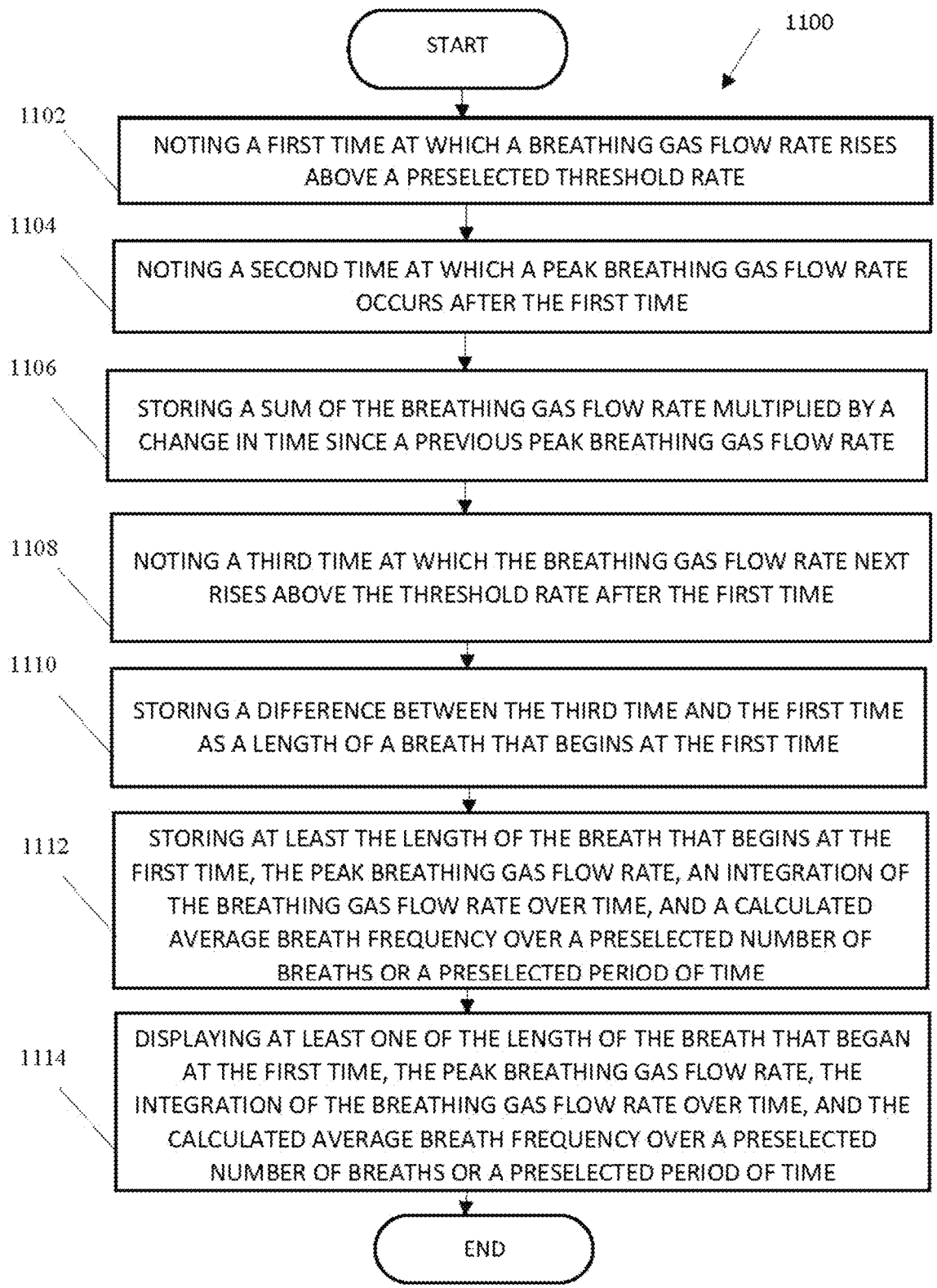
FIG. 36 shows a flowchart for a method of collecting and storing breathing information.

FIG. 36 shows a method embodiment of the present invention. Method 1100, a method of collecting and storing breathing information, includes noting a first time at which a breathing gas flow rate rises above a preselected threshold rate in block 1102. Block 1104 of method 1100 includes noting a second time at which a peak breathing gas flow rate occurs after the first time. Additionally, in block 1106, a sum of the breathing gas flow rate multiplied by a change in time since a previous peak breathing gas flow rate is stored. Further, noting a third time at which the breathing gas flow rate next rises above the threshold rate after the first time is included in block 1108. Block 1110 includes storing a difference between the third time and the first time as a length of a breath that begins at the first time. Further, block 1112 includes storing at least the length of the breath that begins at the first time, the peak breathing gas flow rate, an integration of the breathing gas flow rate over time, and a calculated average breath frequency over a preselected number of breaths or a preselected period of time. Displaying at least one of the length of the breath that began at the first time, the peak breathing gas flow rate, the integration of the breathing gas flow rate over time, and the calculated average breath frequency over a preselected number of breaths or a preselected period of time is included in block 1114.

Training using the present invention may include using the device to deliver one or more hypoxia profiles to a user while teaching the user to monitor and react to one or more symptoms of incipient or actual hypoxia and to switch to an oxygen recovery mode when she detects one or more of the symptoms. The symptoms to be monitored may include a decrease in oxygen saturation of hemoglobin, an increase in heart rate, an increase in blood pressure, an increase in breathing rate, and a decrease in body temperature. Other symptoms may be observable and used in detecting hypoxia.

Figure 37:
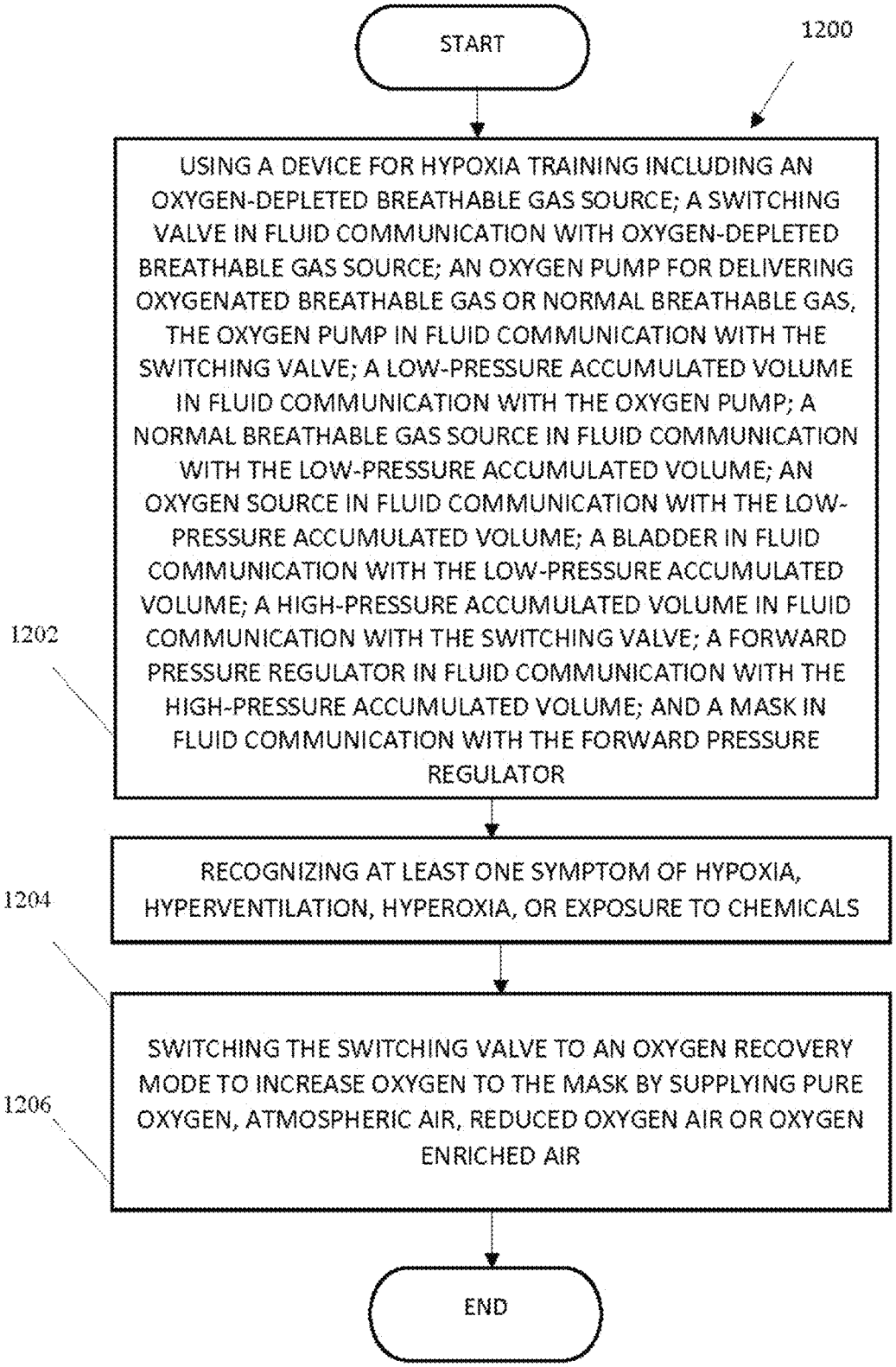
FIG. 37 shows a flowchart for a method of recovering from or avoiding hypoxia.

FIG. 37 shows a method embodiment of the present invention. Method 1200 is a method of recovering from or avoiding hypoxia. Method 1200 includes block 1202, which includes using a device for hypoxia training including an oxygen-depleted breathable gas source; a switching valve in fluid communication with oxygen-depleted breathable gas source; an oxygen pump for delivering oxygenated breathable gas or normal breathable gas, the oxygen pump in fluid communication with the switching valve; a low-pressure accumulated volume in fluid communication with the oxygen pump; a normal breathable gas source in fluid communication with the low-pressure accumulated volume; an oxygen source in fluid communication with the low-pressure accumulated volume; a bladder in fluid communication with the low-pressure accumulated volume; a high-pressure accumulated volume in fluid communication with the switching valve; a forward pressure regulator in fluid communication with the high-pressure accumulated volume; and a mask in fluid communication with the forward pressure regulator. Block 1202 includes recognizing at least one symptom of hypoxia, hyperventilation, hyperoxia, or exposure to chemicals. In addition, method 1200 includes switching the switching valve to an oxygen recovery mode to increase oxygen to the mask by supplying pure oxygen, atmospheric air, reduced oxygen air or oxygen enriched air in block 1204.

The present invention may also be used to treat coronary disease and arterial hypertension. It may also be used to prepare for a coronary intervention. Further, the present invention may be used in altitude acclimatization and in training for improved lower altitude athletic performance, e.g., for practitioners of the concept of Living Low-Training High.

The present invention can be used for simulating a variety of equipment malfunctions that may occur during flight leading to insufficient breathing gas flow to the mask or insufficient oxygen in the breathing gas. Excessive breathing resistance may occur when experiencing these malfunctions. Reduced oxygen conditions have adverse effects on the health and diminish the ability of a pilot or crew member to carry out expected functions (e.g., aviation, navigation and communication). If an adverse oxygen condition is not corrected, further impairment of the pilot can occur, leading to loss of ability to fly safely and pilot or crew member unconsciousness.

Examples of adverse conditions and malfunctions that lead to low or insufficient oxygen in the body include but are not limited to: hypoxia, hyperventilation, hyperoxia, and exposure to chemicals. These conditions may be associated with a variety of mechanical problems with the oxygen supply systems, including but not limited to: pressurized tank failures, faulty valves/solenoids, leaks, seal failures, switching mechanism failures, and mask irregularities). Further, oxygen supply problems could be due to mechanical or structural failures that cause loss of cabin or cockpit pressure.

It is preferred that a variety of emergency situations be experienced in a safe, controlled and flight simulated environment, so that pilots and crew members may be trained in awareness of physical sensations (e.g., physiological changes) that he or she may experience when exposed to low oxygen. It is preferred that a pilot or crew member be able to differentiate between different types of situations that lead to low oxygen. It is preferred that the pilot or crew member learns to take appropriate corrective actions when they experience one or more low oxygen adverse conditions, according to the identified cause. It is preferred that a pilot or crew member has a means to practice returning to a safe flight condition once they are exposed to the low oxygen adverse condition. The latter is an essential step in training as it will save lives.

The present invention may be used to combine awareness, diagnosis and corrective actions in an integrated training regime. Moreover, the present invention offers a means to combine the experience of insufficient oxygen with flight training, so it is carried out in a combined way to achieve a high degree of realism (i.e., training fidelity) further benefiting air crew safety.

The present invention involves the previously described equipment for generating gases with varying oxygen concentration, referred to as the hypoxia training device or system (including hypoxia training device 600), including one or more operational linkages to: (1) an aircraft flight simulator, (2) physiological monitoring equipment (3) cognitive assessment tools and (4) a means to implement recovery to establish safe flying conditions.

Figure 38:
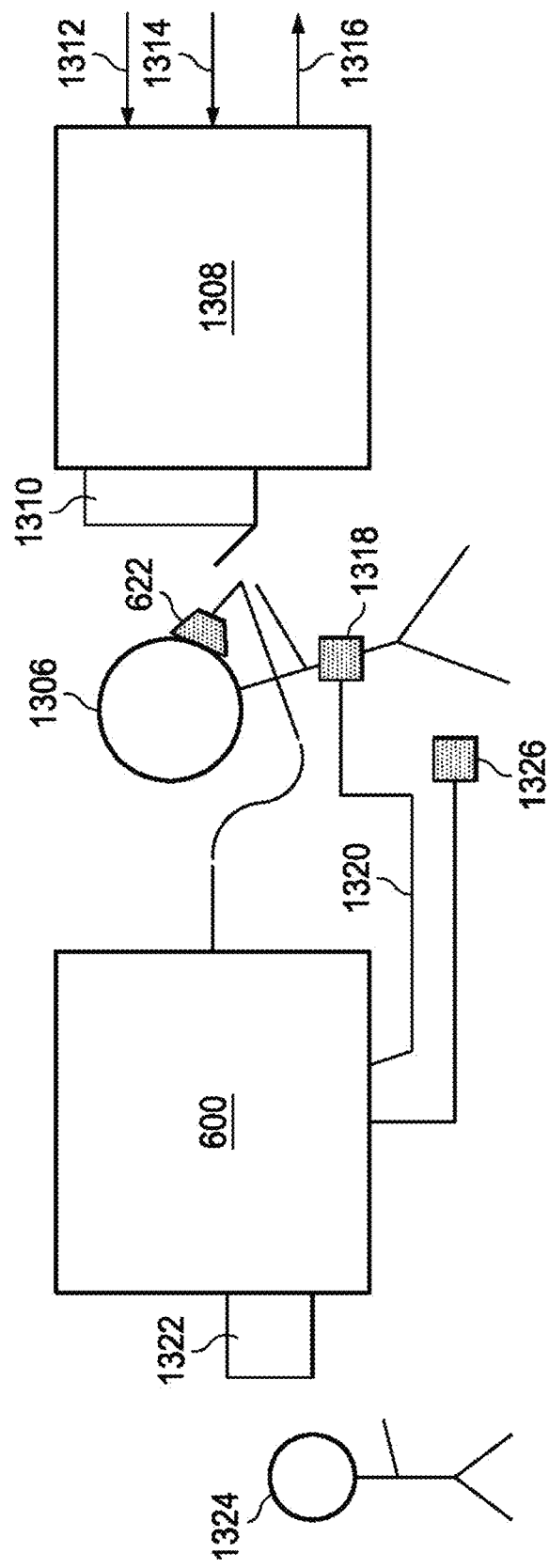
FIG. 38 shows a hypoxia training device coupled to a flight simulator, physiological monitors, and a switch to supply oxygen to a test subject.

FIG. 38 shows an embodiment of the present invention, depicting how the hypoxia training device equipment will be used, and showing examples of operational linkages needed to achieve integrated and realistic training in oxygen supply malfunctions. Such a system may be used to assess the extent that the test subject (e.g., a pilot or a crew member) has had sufficient training to recognize hypoxia effects and to take mitigating actions according to procedures in a timely way to prevent further danger to the aircraft and personnel. The term operational link is defined as two or more systems having an ability to send and/or receive signals between each other. Signals can be in the form of computer generated digital signals, visual indicators, audio signals and voice communication.

Figure 39:
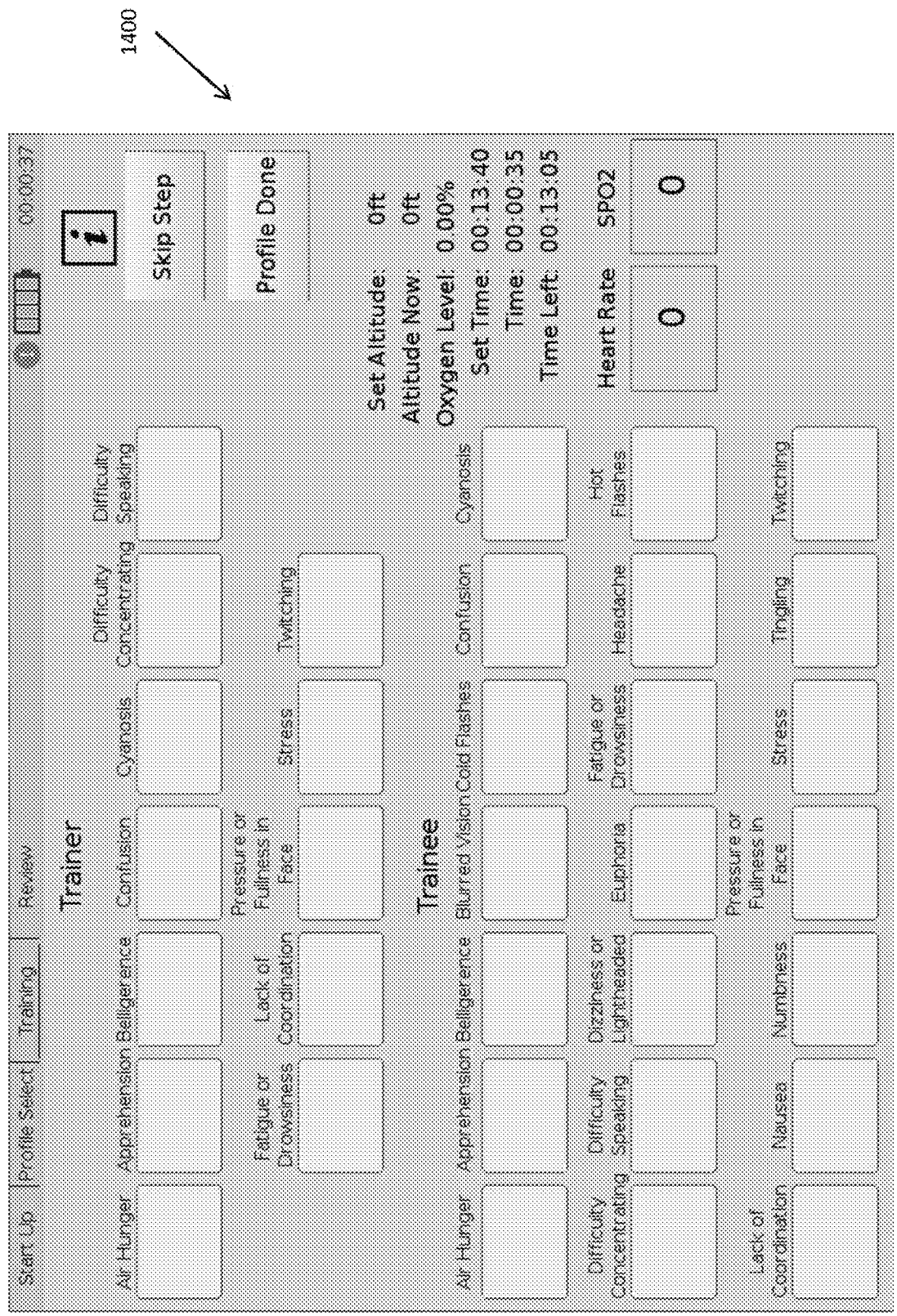
FIG. 39 illustrates an exemplary touch screen display associated with a hypoxia training device.

FIG. 38 illustrates an embodiment of the present invention, a hypoxia training device coupled to a flight simulator, physiological monitors, and a switch to supply oxygen to a test subject. Hypoxia training device 600 is shown coupled to a mask 622 being worn by a test subject 1306. The test subject 1306 is positioned to operate a flight simulator 1308 via the flight simulator display and controls 1310, and the flight simulator 1308 is equipped with voice input 1312, flight instruction input 1314, and flight data recording output 1316. The test subject is also wearing one or more physiological monitors 1318, which are coupled to a biometry port 1320, which in turn is coupled to the hypoxia training device 600. The hypoxia training device 600 is equipped with a touch screen 1322 for use by an attendant 1324 who is operating the hypoxia training device 600. An exemplary emergency oxygen activation switch 1326 is also shown in FIG. 39.

Flight simulators such as flight simulator 1308 operate by artificially recreating aircraft flight and/or cockpit situations. Flight simulators are often used for pilot and crew member training. There are many kinds of flight simulators with which the hypoxia training equipment could be used. Aircraft flight simulators used by commercial airlines and the military have large, complicated and complex configurations and equipment, with multiple computers, large controls, multiple script file interfaces, and large racks of equipment. Often separate simulators are required for each aircraft type being modeled. This configuration results in large initial costs in purchasing each simulator, increased space requirements, operation expenses (including cooling the racks of equipment), and maintaining the large amount of equipment required. Operation of these simulators require skilled technicians and medical practitioners who add to the overall complexity. Also, certain flight simulators may support movements of the cockpit through hydraulic rams offering multiple degrees of freedom, and may be used to disorientate the pilot or crew member or cause physical exertion. Alternatively, there are less complicated designs where the cockpit simulation is interfaced through a computer program and storage media to a personal computer, desktop monitor and keyboard. These may be operated via a game-type console. These types of flight simulators are available at the consumer level (e.g., from Microsoft Corp.). The present invention for pilot or crew member training in oxygen emergencies can be potentially used in conjunction with any existing or future flight simulation systems.

The illustrated flight simulator 1308 incorporates a flight simulator display and controls 1310, indicative of a flight situation. The display and controls allow the test subject 1306 to carry out one or more functions typically involved in flying an aircraft (e.g., tasks involving aviation, navigation, or communication). Controls allow the test subject 1306 to perform maneuvers such as change in direction, climb, descend or carry out cockpit procedures. The flight simulator 1308 is shown with voice input 1312 to the test subject 1306 from attending personnel such as attendant 1324, allowing the test subject 1306 to receive voice instructions or to communicate to attending personnel. The test subject 1306 may receive flight instructions via flight instruction input 1314. The example indicates a capability to record audio or digital signals resulting from operation of the simulator 1308 via flight data recording output 1316. The test subject 1306 is located in proximity to the flight simulator 1308 and in proximity to the hypoxia training device 600 and is in a position to operate either or both equipment items. The test subject 1306 wears the mask 622 configured as described in previous examples, which includes an on demand breathing capability. The mask is operably coupled to the hypoxia training device 600.

When the test subject 1306 is placed into a flight simulation environment, it is preferable to include a means to monitor physiological parameters of the test subject 1306. Physiological measurements can include but are not limited to: ventilation rate, breath volume, heart rate, arterial oxygen, electrocardiogram (ECG), or blood pressure. The hypoxia training device 600 provides an exact means for operational linkage to these monitoring devices. One example of physiological measurement is the breath monitor as previously described in this application which uses a pressure sensing algorithm. Other wearable physiological monitors are available. For example, saturation of peripheral oxygen (SpO2) can be monitored by a pulse oximeter such as the one made by Datex Ohmeda Corp. or a Bedside SpO2 Patient Monitoring System (e.g, from Covidien), with placement on the index finger. The pulse oximeter can be functionally connected to the hypoxia training device. Near Infrared Spectroscopy sensors such as PocketNIRS (from Dynasense), can also be worn on the forehead together with a previously validated NIRS sensor (from, e.g., INVOS Cerebral Oximeter, Somanetics). Pulse rate monitoring is also typically performed by the same pulse oximeters that measure the SpO2 levels. Example of such a pulse oximeter is the one made by Nonin (Onyx finger pulse oximeters, various models). Pulse measurements in typical pulse oximeters are achieved by monitoring the change in volume between successive heartbeats. This change in volume affects the amount of light, such as the amount of red or infrared light, that will transmit through the tissue. This fluctuation can be measured by a pulse oximeter using a transmissive or reflectance oximetry setup internal to the oximeter. Several other means of pulse rate monitoring as well as several other types of pulse oximeters can also be utilized for our training device to facilitate the operational linkage for training. ECG permits measurement of heart rate variability (HVR) including frequency domain indicators of stress and underload. Galvanic skin response can be used to assess the sympathetic nervous system/fight or flight response. One or more physiological monitors 1318 are depicted in FIG. 38. Physiological measurements are operationally linked to the hypoxia training device via a biometry port 1320. Physiological data is displayed for use by technicians and attending staff, e.g., attendant 1324, or is displayed directly to the test subject 1306. Physiological data can additionally be recorded on electronic storage media.

The one or more physiological monitors 1318 are operably coupled to the hypoxia training device 600 via the biometric port 1320. The biometric port 1320 may be varied in design (e.g., USB, serial, CDL). Digital electrical information is sent from the one or more physiological monitor 1318 to an interface computer board (not shown), provided by the manufacturer or manufacturers of the one or more physiological monitor 1318. The interface board is housed within the hypoxia training device 600. The sensor interface board is in electrical communication with the master control board of the hypoxia training device 600. Information from the monitor 1318 is captured by the internal software of the hypoxia training devices 1302, from which it is sent to a display or is transferred to electronic storage media.

FIG. 39 shows an exemplary touch screen display 1400 that may be displayed on the touch screen 1322 in an embodiment of the present invention. The touch screen display 1400 can be configured to display information about the status of the hypoxia training device 600 and the physiology of the test subject 1306 as received from the one or more physiological monitors 1318. The touch screen display 1400 can be viewed and activated by an attendant. The touch screen display 1400 is designed to allow the attendant 1324 to input commands via touch and is the primary means by which the attendant 1324 controls and receives feedback/status for the hypoxia training device 600. The touch screen display 1400 is programmed to display a number of screen views which can be selected by the attendant 1324 via a selection menu. The touch screen display 1400 can be used to enter information about the training, such as personal information of the test subject 1306 (e.g., age, weight, height, date, start time, end time). Screens views can provide test protocol instructions to the attendant 1324 such as to secure the mask on the test subject and to secure and activate the one or more physiological monitors 1318.

A different screen view allows the attendant 1324 to select oxygen concentration and time profiles for the gas being provided to the test subject 1306 via the mask 622. Profiles can be selected by touching points on the touch screen display 1400. When the profile is running, a different screen allows the attendant 1324 to use the touch screen display 1400 to log the specific physiological symptoms the test subject 1306 is experiencing, cognitive responses from the test subject 1306 as well as physiological information that is being displayed. The different scenarios that lead to a symptom being logged include but are not limited to communication between the test subject 1306 and the attendant 1324, visual observation of the test subject 1306 cognitive behavior by the attendant 1324, and physiological parameters displayed on the touch screen display 1400. Every time a symptom or status button is pressed, a timestamp is logged. The touch screen display 1400 may display physiological data from the test subject 1306 such as breaths per minute (BPM) & SpO2. These parameters can be graphed on a single graph on a training review screen view. The touch screen display 1400 allows any logged physiological symptoms or cognitive responses to be overlaid on top of the training review screen graph. Additional screens allow the attendant 1324 to customize the views. The touch screen display 1400 may also display maintenance information with a screen view such as run time or last calibration.

For the purposes described herein, a suitable touch screen for the touch screen display 1400 is a 10.4" Advantech IDS-3110 with a native resolution of 1024×768. The touch screen 1322 may use a 5-wire resistive touch screen solution. There are many types of touch screens, with different sizes and screen resolutions available from commercial sources which may serve this purpose. Preferably the touch screen is mounted on the hypoxia training device 600. Mounting may include a means to tilt or adjust the vertical or horizontal viewing angle. The touch screen display 1400 provides buttons enabling the user to adjust the typical screen parameters such as, e.g., brightness, contrast, or color. The touch screen display 1400 receives video display information from the internal processing subsystem of the hypoxia training device 600 via a DVI cable. The touch screen 1322 provides the x, y coordinates of the touch via a serial cable to the internal processing subsystem of the hypoxia training device 600. It may be preferred for the touch screen to receive power from an internal power converter (not shown) of the hypoxia training device 600. An external HDMI port is incorporated into the hypoxia training device 600 to support displaying the touch screen content on a larger external monitor (such as a flight simulator screen). In certain trainings, the touch screen 1322 is to be viewed and activated by the test subject 1306, or alternatively by an attendant 1324. The touch screen 1322 can also be connected to the device externally via different communication ports including but not limited to HDMI, USB, or serial ports.

Figure 40:
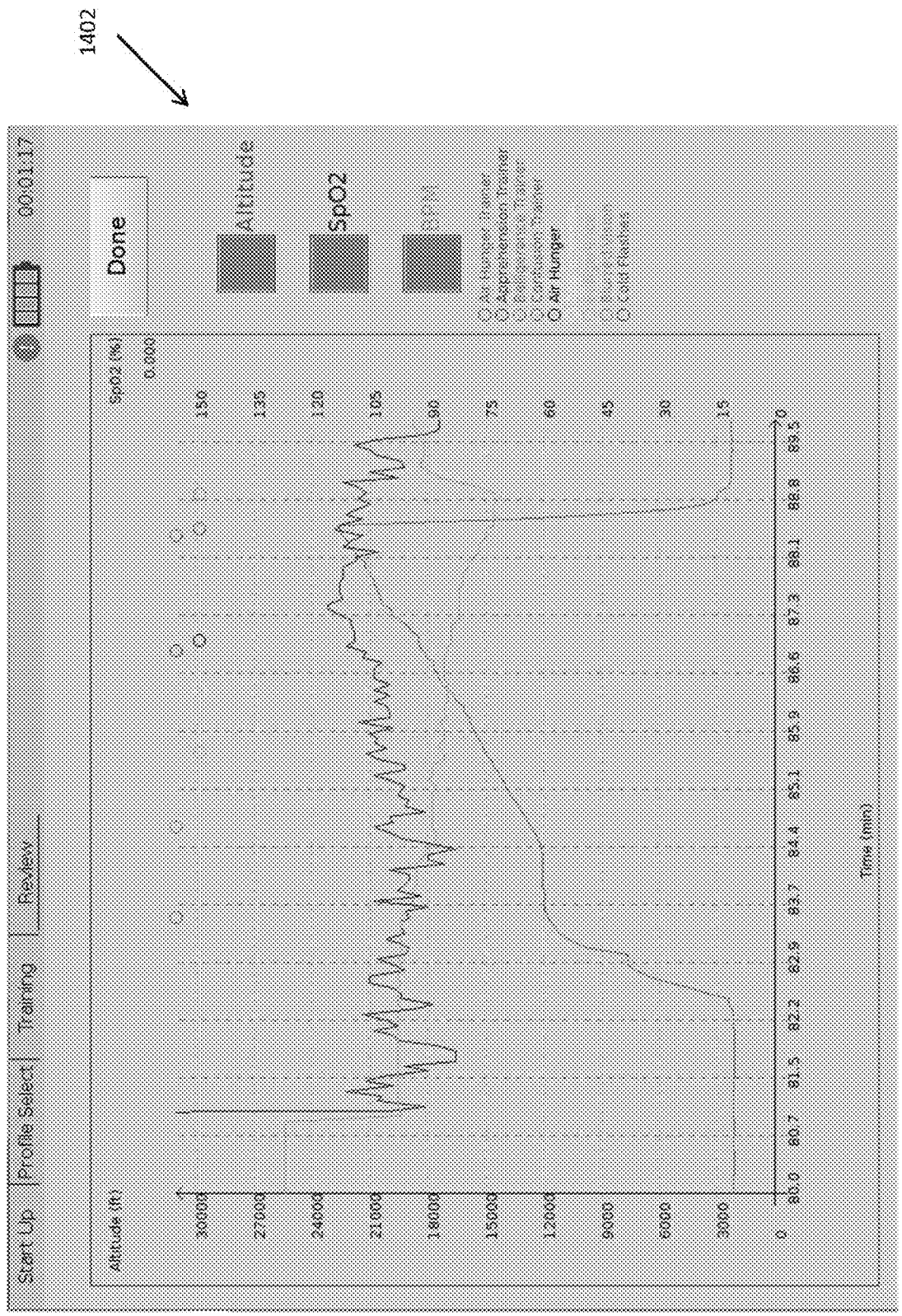
FIG. 40 shows another exemplary touch screen display associated with a hypoxia training device.

The touch screen 1322 is configured to receive and record cognitive responses of the test subject 1306 via touch screen display 1400, allowing cognitive responses to be recorded and assessed during training. The attendant 1324 may be in voice communication with the test subject 1306, allowing the attendant 1324 to ask questions to the test subject 1306 and to receive responses from the test subject 1306. The attendant 1324 may record responses on the touch screen 1322, where responses are time stamped and recorded on electronic media. Examples of test subject 1306 responses can include: headache, narrowing of visual field, dizziness, drowsiness, difficulty making voluntary movement, tingling in extremities, a feeling of unconcern, slow reaction times, and numbness. These sensations and responses are typical but are non-limiting examples. The exemplary touch screen display 1400 shown in FIG. 39 includes a selection menu whereby physiological symptoms and test subject responses can be recorded. Both test subject 1306 and attendant 1324 may record responses. Physiological data is also displayed. FIG. 40 shows touch screen display 1402, an example of a touch screen display showing flight training information; also shown are time stamped events corresponding to test subject symptoms and responses.

The cognitive responses shown on the touch screen display 1402 in FIG. 40 are non-limiting. Cognitive function tests can also include, e.g., simple computation, serial subtraction, eye-hand coordination, semantic memory, visual-motor coordination, short-term memory, graphic memory, and coordination. Tests are available that indicate impact of hypoxia on visual attention, working memory, verbal-sequencing processing, visual-perceptual speed, visual-motor speed, divided attention, capacity for multitasking, visual scanning, speed of information processing, number and letter sequencing skills, ability to systematically apply an organizing principle, immediate memory, motor coordination, and ability to shift mental set (for example, Kay G. 1995 CogScreen Aeromedical Edition Professional Manual Washington DC: Cogscreen LLC). Another example would be the King-Devick Test (Stepanek et al 2013, Aviation, Space and Environmental Medicine vol 84 No 10, 1107-1022). The present invention for pilot and crew member training is to be potentially used in conjunction with any existing or future methods to monitor cognitive response.

A useful aspect of the invention is that, through operational linkage to the touch screen 1322 and the touch screen display 1400, the attendant 1324 determines the level of impaired function due to hypoxia, in a way that is independent of physiological measurements. It is established that oxygen saturation can be a deceptive indicator of impaired function. Persons experiencing peripheral blood saturation (SpO2) levels of 80% may experience very little if any cognitive or motor impairment, while other persons may experience serious effects of hypoxia at this reduced level of oxygen saturation. Likewise, some persons may experience symptoms of hypoxia at 95% SpO2 levels where another person's function may not be affected. The present invention allows the attendant 1324 to adjust oxygen profiles to allow the test subject 1306 to experience the symptoms of hypoxia, based on the level of observed motor and cognitive impairment. Moreover, the invention may be used to assess the individual's conditions needed for impairment, on a test-subject-to-test-subject basis. It is preferred that cognitive responses are monitored and recorded on a continuous basis during the test, so the oxygen profiles can be adjusted as needed, either to induce or maintain impairment. Oxygen profiles also may be adjusted to achieve recovery from impaired function, based on observed and recorded cognitive responses.

Embodiments include a means to activate a source of emergency or supplementary oxygen for recovery; in FIG. 38, an exemplary oxygen activation switch 1326 is shown. The hypoxia training device 600 is a source of supplemental oxygen through a switching mechanism such as switch 1326 positioned in proximity to the test subject 1306, which can be activated by the test subject 1306 or the attendant 1324 as needed. The hypoxic training as described herein includes the physical components for one or more oxygen recovery modes as represented by FIGS. 24-31. Sources for oxygen recovery can be pure oxygen, atmospheric air, reduced oxygen air, or oxygen enriched air. During training in a flight simulator, when a test subject 1306 senses a hypoxic event, the test subject 1306 has the means for electromechanical activation of an oxygen recovery source via the oxygen activation switch 1326, where selection of the oxygen activation switch 1326 is part of the flight simulation training. Oxygen activation switch 1326 is operably coupled with the hypoxia training device 1306, and where oxygen recovery to be provided via the mask 622 in fluid communication with the hypoxia training device 600. In some instances, the recovery gas is generated in situ from air, which reduces the need for oxygen gas storage. Typically, oxygen is stored in pressurized tanks in facilities governed by fire and safety regulations. It is difficult to commission these types of facilities. The hypoxia training device 600 minimizes the difficulties and expense of oxygen storage.

Here we give examples of the use of the invention for test subject training. In training examples 1-3, the test subject 1306 is functionally linked to a flight simulator such the flight simulator 1308 and wearing a mask 622 connected to the hypoxia training device 1306. The flight performance of the test subject 1306 (e.g., altitude precision, air speed control, heading control) is continuously monitored. During the test, reduced oxygen gas is delivered. The hypoxia training device 600 is operated to allow adequate ventilation volumes, adequate ventilation rates and adequate respiration frequency (bpm) according to the activity of the test subject 1306. In other words, the gas volume and flow available to the test subject 1306 is unrestricted and only the oxygen concentration of the gas is restricted. The examples involve the use of the hypoxia training device 600 to create a situation of early onset of hypoxia (in which the symptoms are mild), because early recognition is beneficial for recovery from an oxygen malfunction. The test subject 1306 also is trained to recognize that low oxygen symptoms occur when flying at altitudes where atmospheric oxygen partial pressures are sufficient for normal physiology (typically at or below 10,000 ft). The examples also include periods of repeated exposure to reduced oxygen gas, giving the test subject 1306 an improved ability to differentiate the experience of hypoxia from pre-hypoxia and post hypoxia conditions.

In training examples 4-5, the test subject 1306 is operationally linked to a flight simulator such as flight simulator 1308, and wearing a mask 622 connected to the hypoxia training device 600. The flight performance of the test subject 1306 (e.g., altitude precision, air speed control, heading control) is continuously monitored. During the test, the test subject 1306 experiences an oxygen malfunction that causes a restriction of gas flow to the mask 622. This restricts the test subject 1306 in terms of ventilation volumes, ventilation rates and respiration frequency (bpm), which are contrary to the physiological requirement of the test subject 1306. In other words, the breathing gas volume available via the mask 622 is restricted, so the test subject 1306 has a reduced intake of air flow, and the oxygen content in the air flow. The test subject 1306 is to be trained to recognize the symptoms associated with this type of malfunction. Also, this type of malfunction is not directly altitude related and may occur at altitudes where atmospheric oxygen partial pressures are sufficient for normal physiology (below 10,000 ft). The examples also include periods of repeated exposure to restricted flow. Through multiple experiences, the test subject 1306 gains an ability to differentiate between normal gas flow to the mask 622 and symptoms experienced with restricted gas flow to the mask 622. Malfunctions may be introduced in the training in a way that is unanticipated by the test subject 1306. Malfunctions may be introduced when the test subject 1306 has a heavy cockpit workload.

In training example 6, the test subject 1306 is trained to experience and recognize early stage symptoms of hypoxia through a sequence of low oxygen events. The test subject 1306 is given the opportunity to take corrective action through activation of supplemental oxygen provided via the hypoxia training device 600. The test subject 1306 also experiences a second type of malfunction where breathing gas supply to the mask 622 is restricted. The test subject 1306 is again given the opportunity to take corrective actions. By experiencing two malfunctions over short space of time, the test subject 1306 can make a direct compare-and-contrast assessment, making it possible to determine the type of malfunction according to body sensations and physiological changes, and select the right corrective procedures under flight conditions. Again, the test subject 1306 is functionally linked to a flight simulator such as flight simulator 1308, and wearing a mask 622 connected to the hypoxia training device 600. The flight performance of the test subject 1306 (e.g., altitude precision, air speed control, heading control) is continuously monitored.

Training examples 1-6 are non-limiting, with many variations possible, such as duration of the malfunction, the frequency at which the malfunction repeats itself during the test. Flying maneuvers being undertaken by the test subject 1306 can be varied. Oxygen content of the gas can be varied, and may be adjusted during the test, according to the responses of the test subject 1306. The period of incipient hypoxia can be varied, to maximize a familiarity of the test subject 1306 with these signs and symptoms. The recovery source can be varied to include pure oxygen, oxygen enriched air, oxygen depleted air and atmospheric air. The duration of the post hypoxia recovery period can be short (e.g., 1 minute) or lengthy (e.g., 10 minutes) allowing the test subject 1306 to recognize that recovery from hypoxia is occurring, and allowing a compare-and-contrast assessment of symptoms and signs of recovery, versus hypoxic and pre-hypoxic periods experienced during the training. Oxygen malfunction and recovery events can be implemented in the training in a way that cannot be anticipated by the test subject 1306.

In training examples 1-6, reference is made to "pilot" as a non-limiting example. The training examples are applicable or adaptable to test subjects such as test subject 1306 generally.

| Training Example 1: Low oxygen content malfunction | |
|---|---|
| Time (minutes) | Actions |
| 0-25 | Pilot flies and maneuvers according to instructions. Pilot reaches an altitude of 25,000 ft. Attendant monitors physiology and cognitive responses. Flight performance is monitored. Oxygen content is 21% |
| 25-26 | Attendant incrementally adjusts profile to simulate effects of high altitude cabin pressure failure. Oxygen content reduced from 21% to 12%. |
| 27 | Pilot recognizes symptoms. Activates secondary oxygen. Pure oxygen used for recovery. |
| 28-42 | Pilot established safe flight pattern and altitude. Attendant monitors physiology and cognitive responses during pilot recovery. Pilot recognizes post hypoxia changes in symptoms and physiology. |
| 43 | Test complete |
| Follow up | Pilot is provided with test results and given performance feedback. |

| Training Example 2. Low oxygen content malfunction | |
|---|---|
| Time (minutes) | Actions |
| 0-20 | Pilot flies and maneuvers according to instructions. Pilot reaches a max altitude of 5,000 ft. Attendants monitor physiology and cognitive responses. Flight performance is monitored. The oxygen content is 21%. |
| 20-30 | Attendant progressively adjusts oxygen concentration profile based on cognitive responses from 21% to 17% to establish early symptoms of mild hypoxia in the pilot. |
| 30-38 | Pilot is instructed to perform maneuvers and tasks at 5,000 ft. Attendant monitors cognitive responses. Flight performance is monitored. |

Training Example 2. Low oxygen content malfunction

| Time (minutes) | Actions |
|---|---|
| 39 | Pilot recognizes symptom of low oxygen. |
| 39-40 | Pilot takes corrective actions by activation of supplementary oxygen and implements emergency procedures. Oxygen enriched air is used for recovery. Oxygen content is 40%. |
| 40-47 | Attendant monitors physiology and cognitive responses during pilot recovery. Flight performance is monitored. Pilot recognizes post hypoxia changes in symptoms and physiology. |
| 48 | Test complete. |
| Follow up | Pilot is provided with test results and given performance feedback. |

Training Example 3. Low oxygen content malfunction

| Time (minutes) | Action |
|---|---|
| 0-12 | Pilot flies and maneuvers according to instructions and achieves max altitude of 6,000 ft. Oxygen content is 21%. Attendants initiate continuous monitoring of physiology and cognitive responses |
| 12-15 | Attendant selects profile to limit oxygen to the pilot test subject by incremental adjustment of oxygen concentration profile based on cognitive responses. |
| 15-20 | Attendant adjusts oxygen concentration profile to correspond to incipient hypoxia. Oxygen content is 14.5%. |
| 20-25 | Pilot is instructed to perform maneuvers and tasks maintaining 6,000 ft. Attendant continues to monitor cognitive responses. Oxygen content maintained at 14.5% |
| 25-26 | Pilot recognizes low oxygen symptoms. |
| 26-27 | Pilot takes corrective actions by following a check list including: strong breath inhale and exhale, checks for mask function, performs mechanical adjustments, checks switches, pilot correctly selects on altitude related malfunctions. Pilot correctly identifies a misaligned valve position and bypasses valve. |
| 27-30 | Prompted by corrective actions of pilot, attendant adjust breathing gas supply to effect recovery. Atmospheric air is used for recovery. Pilot recognizes post hypoxia changes in symptoms and physiology during recovery. |
| 30-40 | Pilot maneuvers as instructed. Attendant monitors physiology and cognitive response during recovery |
| 40 | Test complete. |
| Follow up | Pilot is provided with test results and given performance feedback. |

Training Example 4. Breathing gas is restricted

| Time (minutes) | Action |
|---|---|
| 0-18 | Pilot flies and maneuvers according to instructions and achieves max altitude of 6,000 ft. Oxygen content is 20%. Attendants initiate continuous monitoring of physiology and cognitive responses |
| 19 | Attendant selects to stop gas flow to the mask. After 10 seconds full gas flow is resumed. |
| 19-20 | Pilot recognizes malfunction and performs corrective equipment checks. |
| 20-24 | Pilot flies and maneuvers according to instructions maintaining altitude of 6,000 ft. Oxygen content is 20%. Attendants continue monitoring of physiology and cognitive responses |
| 25 | Attendant selects to stop gas flow to the mask. After 10 seconds full gas flow is resumed. |
| 26 | Pilot recognizes malfunction and performs corrective equipment checks. |
| 27-74 | Pilot flies and maneuvers according to instructions maintaining altitude of 6,000 ft. Oxygen content is 20% at normal flow. Attendants continue monitoring of physiology and cognitive responses |
| 75 | Attendant selects to stop gas flow to the mask. After 10 seconds full gas flow is resumed. |
| 75 | Pilot recognizes malfunction and performs corrective equipment checks |
| 75-90 | Pilot flies and maneuvers according to instructions maintaining altitude of 6,000 ft. Oxygen content is 20% at normal flow. Attendants continue monitoring of physiology and cognitive responses |

| Training Example 4. Breathing gas is restricted | |
|---|---|
| Time (minutes) | Action |
| 90 | Test complete |
| Follow up | Pilot is provided with test results and given performance feedback. |

| Training Example 5. Breathing gas is restricted | |
|---|---|
| Time (minutes) | Action |
| 0-18 | Pilot flies and maneuvers according to instructions and achieves max altitude of 12,000 ft. Oxygen content is 20%. Attendants initiate continuous monitoring of physiology and cognitive responses |
| 19 | Attendant selects to restrict gas flow equivalent to a maximum value of 6 lpm. After 30 seconds full gas flow is resumed at 20% content (up to a maximum value equivalent to 36 lpm. |
| 19-20 | Pilot recognizes symptoms and performs corrective equipment checks. |
| 20-21 | Pilot flies and maneuvers according to instructions, changes altitude to 10,000 ft and changes heading. Oxygen content is 20%. Attendants continue monitoring of physiology and cognitive responses. |
| 22 | Attendant selects to restrict gas flow allowing only a maximum value of 3.5 lpm. After 30 seconds full gas flow is resumed (up to 35 lpm). |
| 23 | Pilot recognizes symptoms and performs corrective equipment checks. |
| 27-74 | Pilot flies and maneuvers according to instructions maintaining altitude of 10,000 ft. Oxygen content is 21% at normal flow. Attendants continue monitoring of physiology and cognitive responses. |
| 75 | Attendant selects to stop gas flow to the mask. After 10 seconds full gas flow is resumed. |
| 75 | Pilot recognizes malfunction and performs corrective equipment checks |
| 75-90 | Pilot flies and maneuvers according to instructions maintaining altitude of 6,000 ft. Oxygen content is 20% at normal flow rates. Attendants continue monitoring of physiology and cognitive responses. Pilot recognizes post hypoxia changes in symptoms and physiology during recovery. |
| 90 | Test complete |
| Follow up | Pilot is provided with test results and given performance feedback. |

| Training Example 6. Multiple | |
|---|---|
| Time (minutes) | Action |
| 0-10 | Pilot flies and maneuvers according to instructions and achieves altitude of 20,000 ft. Oxygen content is 20%. Attendants initiate continuous monitoring of physiology and cognitive responses |
| 10-12 | Attendant selects profile to limit oxygen to the pilot test subject by incremental adjustment of oxygen concentration profile based on cognitive responses, oxygen content adjusted to correspond to onset of hypoxia. Oxygen content is15.0%. |
| 13-15 | Attendant adjust oxygen supply content to 20%. Attendants continue monitoring of physiology and cognitive responses. |
| 15-17 | Attendant selects profile to limit oxygen to the pilot test subject by incremental adjustment of oxygen concentration profile based on cognitive responses, oxygen content adjusted to correspond to onset of hypoxia. Oxygen content is 13.0%. |
| 17-19 | Attendant adjusts oxygen supply content to 20%. Attendants continue monitoring of physiology and cognitive responses. |
| 19-21 | Attendant selects profile to limit oxygen to the pilot test subject by incremental adjustment of oxygen concentration profile based on cognitive responses, oxygen content adjusted to correspond to onset of hypoxia. Oxygen content is 13.0%. |
| 22 | Pilot recognizes early hypoxia symptoms. Takes corrective action, activates supplemental oxygen. Pure oxygen is selected for recovery. Pilot executes safe flying pattern, descends to 5,000 ft. |
| 23-25 | Pilot flies and maneuvers according to instructions maintaining altitude of 5,000 ft. Oxygen content to the mask is 20% at normal flow rates. Pilot recognizes post hypoxia changes in symptoms and physiology. Attendants continue monitoring of physiology and cognitive responses |
| 26 | Attendant selects to restrict gas flow equivalent to a maximum value of value 5.0 lpm. |

| Training Example 6. Multiple | |
|---|---|
| Time (minutes) | Action |
| 26 | Pilot recognizes symptoms and performs corrective equipment checks and adjusts a loose fitting. |
| 27-35 | Pilot flies and maneuvers according to instructions maintaining altitude of 6,000 ft. Oxygen content readjusts to 20% at normal flow rates. Pilot recognizes post hypoxia changes in symptoms and physiology during recovery. Attendants continue monitoring of physiology and cognitive responses. |
| 36 | Test complete |
| Follow up | Pilot is provided with test results and given performance feedback. |

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. In embodiments of any of the compositions and methods provided herein, "comprising" may be replaced with "consisting essentially of" or "consisting of". As used herein, the phrase "consisting essentially of" requires the specified integer(s) or steps as well as those that do not materially affect the character or function of the claimed invention. As used herein, the term "consisting" is used to indicate the presence of the recited integer (e.g., a feature, an element, a characteristic, a property, a method/process step or a limitation) or group of integers (e.g., feature(s), element(s), characteristic(s), propertie(s), method/process steps or limitation(s)) only.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AB, BBC, AAABCCCC, CBBAAA, CABABB, and so forth. The skilled artisan will understand that typically there is no limit on the number of items or terms in any combination, unless otherwise apparent from the context.

As used herein, words of approximation such as, without limitation, "about", "substantial" or "substantially" refers to a condition that when so modified is understood to not necessarily be absolute or perfect but would be considered close enough to those of ordinary skill in the art to warrant designating the condition as being present. The extent to which the description may vary will depend on how great a change can be instituted and still have one of ordinary skilled in the art recognize the modified feature as still having the required characteristics and capabilities of the unmodified feature. In general, but subject to the preceding discussion, a numerical value herein that is modified by a word of approximation such as "about" may vary from the stated value by at least #1, 2, 3, 4, 5, 6, 7, 10, 12 or 15%.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

REFERENCES

Rainford D J, Gradwell D P, eds. Ernsting's aviation medicine, 4th ed. New York: Oxford University Press; 2006.

D. S. Files, James T. Webb, and A. A. Pilmanis, Depressurization in Military Aircrafts: Rates, Rapidity, and Health Effects for 1055 incidents, Aviation, Space, and Environmetal Medicine, 76 (6), 2005, 523-529.

Sausen K P, Bower E A, Stiney M E, et al. A closed-loop reduced oxygen breathing device for inducing hypoxia in humans. Aviation Space and Environmental Medicine 2003; 74:1190-7.

Artino A R, Folga R V, Swan B D. Mask-on hypoxia training for tactical jet aviators: evaluation of an alternate instructional paradigm. Aviation Space and Environmental Medicine 2006; 77:857 63.

Artino A R, Folga R V. Normobaric Hypoxia Training: The Effects of Breathing-Gas Flow Rate on Symptoms. Aviation Space and Environmental Medicine 2009; 80:547-552.

Westerman, Roderick A. Hypoxia familiarisation training by the reduced oxygen breathing method. ADF Health April 2004; 5:11-15.

Voorhees, V.; Adams, R., The use of the oxides of platinum for the catalytic reduction of organic compounds I. Journal of the American Chemical Society 1922, 44, 1397-1405.

Adams, R.; Shriner, R. L., Platinum oxide as a catalyst in the reduction of organic compounds III Preparation and properties of the oxide of platinum obtained by the fusion of ceiloroplatinic acid with sodium nitrate. Journal of the American Chemical Society 1923, 45, 2171-2179.

Carothers, W. H.; Adams, R., Platinum oxide as a catalyst in the reduction of organic compounds II Reduction of aldehydes activation of the catalyst by the salts of certain metals. Journal of the American Chemical Society 1923, 45, 1071-1086.

Kay G. 1995 CogScreen Aeromedical Edition Professional Manual Washington DC: Cogscreen LLC.

Stepanek et al 2013, Aviation, Space and Environmental Medicine vol 84 No 10, 1107-1022

What is claimed is:

1. A training device that simulates one or more oxygen malfunctions in aircraft flight, comprising:
  a training device configured to be operably coupled to a flight simulator, the training device comprising:
  an oxygen-depleted breathable gas source;
  a switching valve in fluid communication with the oxygen-depleted breathable gas source;
  an oxygen pump for delivering oxygenated breathable gas or normal-oxygen-content breathable gas, the oxygen pump in fluid communication with the switching valve;
  a low-pressure accumulator in fluid communication with the oxygen pump;
  a normal-oxygen-content breathable gas source in fluid communication with the low-pressure accumulator;
  an oxygen source in fluid communication with the low-pressure accumulator;
  a high-pressure accumulator in fluid communication with the switching valve;
  a forward pressure regulator in fluid communication with the high-pressure accumulator; and
  a mask in fluid communication with the forward pressure regulator;
  wherein the training device is configured to disrupt a supply of breathable gas to the mask by providing reduced oxygen breathable gas to the mask or by modifying a breathable gas flow rate to the mask;
  wherein the training device is configured to monitor one or more physiological or cognitive responses of a subject wearing the mask or to allow one or more physiological or cognitive responses of a subject wearing the mask to be monitored; and
  wherein the training device is configured to permit the subject wearing the mask or an attendant or an operator of the training device to correct an oxygen malfunction in simulated aircraft flight.

* * * * *